United States Patent [19]
Cramer, III et al.

[11] Patent Number: 5,307,287
[45] Date of Patent: * Apr. 26, 1994

[54] COMPARATIVE MOLECULAR FIELD ANALYSIS (COMFA)

[75] Inventors: Richard D. Cramer, III, St. Louis, Mo.; Svante B. Wold, Winchester, Mass.

[73] Assignee: Tripos Associates, Inc., St. Louis, Mo.

[*] Notice: The portion of the term of this patent subsequent to Jun. 18, 2008 has been disclaimed.

[21] Appl. No.: 716,824

[22] Filed: Jun. 17, 1991

Related U.S. Application Data

[63] Continuation of Ser. No. 237,491, Aug. 27, 1988, Pat. No. 5,025,388.

[51] Int. Cl.$^5$ ............................................. G06F 15/46
[52] U.S. Cl. ..................................... 364/496; 364/578
[58] Field of Search ............... 364/578, 497, 496, 499, 364/577; 436/86, 89

[56] References Cited

U.S. PATENT DOCUMENTS 4,835,708  5/1989  Frans ..................... 364/497
5,025,388  6/1991  Cramer, III et al. ............. 364/578

Primary Examiner—Jack B. Harvey
Assistant Examiner—Ellis B. Ramirez
Attorney, Agent, or Firm—Robert S. Lipton

[57] ABSTRACT

Comparative Molecular Field Analysis (CoMFA) is an effective computer implemented methodology of 3D-QSAR employing both interactive graphics and statistical techniques for correlating shapes of molecules with their observed biological properties. For each molecule of a series of known substrates the steric and electrostatic interaction energies with a test probe atom are calculated at spatial coordinates around the molecule. Subsequent analysis of the data table by a partial least squares (PLS) cross-validation technique yields a set of coefficients which reflect the relative contribution of the shape elements of the molecular series to differences in biological activities. Display in three dimensions in an interactive graphics environment of the spatial volumes highly associated with biological activity, and comparison with molecular structures yields an understanding of intermolecular associations. CoMFA will also predict the biological activity of new molecular species.

90 Claims, 9 Drawing Sheets

| SEQUENTIAL FUNCTIONAL TASKS | SOFTWARE SOURCE |
|---|---|
| BUILD MODELS IN LATTICE SPACE OF CONFORMERS OF ALL TESTED MOLECULES | ⊕ ANY OF HALF DOZEN COMMERCIAL MOLECULAR MODELING PACKAGES |
| ALIGN EACH CONFORMER IN LATTICE SPACE | ⊕ ALL NECESSARY CODE IN CoMFA FFIT.C |
| CoMFA SPECIFIC INPUT OPTIONS, INCLUDES LATTICE SPACING, PROBE ATOM PROPERTIES, BIODATA, ETC. | ⊕ DESCRIPTION OF NEEDED RUNTIME DATA IN CoMFA Q3DEF.C |
| BUILD 3D-QSAR TABLE | ⊕ ALL NECESSARY CODE IN CoMFA EVAL.C<br>⊕ DESCRIPTION OF NEEDED RUNTIME DATA IN CoMFA DABDEF.C |
| PERFORM PLS ANALYSIS WITH CROSS-VALIDATION | ⊕ ALL NECESSARY CODE IN CoMFA PLS.FOR |
| CONSTRUCT CoMFA GRAPHICAL OUTPUT | ⊕ ALL NECESSARY CODE IN CoMFA MAP.C |
| DISPLAY CoMFA OUTPUT | ⊕ STANDARD MOLECULAR GRAPHICS SOFTWARE |

▭ A SPECIFICALLY CoMFA-RELATED TASK REQUIRING CoMFA SOFTWARE CODE

FIG. 5

COMPARATIVE MOLECULAR FIELD ANALYSIS (COMFA)

This application is a continuation of co-pending allowed application Ser. No. 07/237,491 filed on Aug 26, 1988, and now assigned U.S. Pat. No. 5,025,388.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to the method of comparing in three dimensions the steric and electrostatic fields exerted by molecules with similar binding affinities for a common molecule, and extracting by cross correlation of the fields, the most important common topological features related to the observed differences in binding affinities among those molecules. This method is particularly useful in understanding structure/function relationships in biological chemistry.

2. Description of Related Art

During the past three decades modern biology has come to recognize the importance of the three-dimensional conformation/shape of biological molecules in relation to the observed function and activity of these molecules. Beginning with the first identification of alpha helical structures in proteins through the solution to the structure of DNA as a hydrogen bonded intertwined double helix to current studies by X-ray crystallography of enzyme-substrate complexes, appreciation of the role of shape as a determining factor has continually increased. In fact, it is now understood that a proper description and understanding of the functioning of most biological macromolecules is dependent on an understanding of the three-dimensional shape of the molecules. The situation is often analogized to that of a three-dimensional jigsaw puzzle, where the parts which must fit together interlock in specific patterns in three dimensions. It is now realized that the binding of a molecular substrate to an enzyme is determined by the ability of the substrate to fit a notch/groove/cavity within the enzyme in such a manner that the substrate is both mechanically and chemically stabilized in the correct three-dimensional and thermodynamic orientation to promote the catalytic reaction. Similarly, it has long been recognized that the highly specific binding of antibodies to antigens is accomplished by the recognition by the antibody of the surface shape specific features of the antigen molecule.

Not only is the understanding of these three-dimensional puzzles important to a fundamental understanding of enzymology, immunology, and biochemistry, but such studies are of major interest to therapeutic drug researchers. Most drug effects are accomplished by the binding of a drug to a target receptor molecule. To the extent that the nature of the binding is more fully understood, it should be possible to design drugs which bind to their target molecules with greater precision and effect than even naturally occurring compounds. This therapeutic quest is especially important in cancer research where the generalized side effects of many therapeutic drugs are undesirable and more specific drug interactions are desired.

Along with the recognition of the importance of the three-dimensional stereo conformation of biomolecules has come an appreciation of just how difficult it is to understand how the conformation of the molecules is related to their activity. At the present time, the only known method for determining exactly the three-dimensional shape of any biomolecule is by means of X-ray crystallography. While the number of biomolecules which have had their structure successfully determined by crystallography is growing rapidly, the total number remains relatively small, and an even fewer number have been studied in crystal form in conjunction with their bound substrates or ligands. Of the few ligand-biomolecule combinations which have been successfully analyzed by X-ray crystallography, there is still the open question as to whether the complex exists in a different conformational combination in solution than it does in the crystallized form used for the study, although the evidence suggests that there is no major difference.

The study of the three-dimensional conformation/shape of molecules is thus seen to be one of the core questions in modern molecular biology and biophysics. With the possible exception of the introduction in the not too far distant future of coherent X-ray lasers which may make the three-dimensional imaging of biological macromolecules considerably easier, there have been no fundamental advances in the instrumental techniques available during the last several years. Nor have recent advances in protein sequence determination, either by direct sequencing of the proteins or by sequencing of the precursor DNA molecules, been of much help in elucidating the three-dimensional structures since it was discovered early on that, due to the highly folded protein structure, amino acid side chains from vastly different sections of a protein are involved in the conformation of the receptor or binding site. Similar considerations are true with respect to antibody formation. Only recently has a proposal been made towards understanding the initiation of alpha helixes, perhaps the simplest tertiary protein structure, based on a knowledge of the amino acid sequence in a protein. See Presta, L. G.; Rose, G. D. Science 1988, 240, 1632.

Recognizing the difficult and lengthy time involved in obtaining X-ray crystallographic structures of biomolecules, researchers have pursued alternate, though less exact, paths towards obtaining information on the stereochemical binding of molecules. One such approach, taken by experimental chemists, has been to apply an understanding of basic chemical principles to analyze the likely binding sites of substrates. By examining the chemical structures of various ligands known to bind to a given protein, and relying on an understanding of generalized chemical and stereochemical principles, chemists have made educated guesses concerning which parts of the substrate/ligand would most likely be involved in binding to the protein. Based on these educated guesses, new compounds have been synthesized incorporating predicted reactive sites. The binding affinities of the new substrates for the desired protein have been measured. Some reasonable measure of success in understanding stereochemical binding has been achieved by this empirical method, but failure has been much more frequent than success. This scheme, though rational, is basically one of trial and error and does not lead to a coherent approach to finding or designing new molecules with the desired binding affinities.

Attempts have been made over the years to place the understanding of stereochemical interactions of biomolecules and the development of new substrate molecules on a more quantitative footing. These approaches attempt to systematically relate differences in structures of similar substrate molecules to differences in their observed biological activities. Thus, a "structure activity relationship" (acronymed SAR) is sought for a given class of substrates/ligands. To the extent that these approaches have now been quantified, they are now referred to as "quantitative structure activity relationships" (acronymed QSAR). Generally, the relationship sought in formulating a QSAR is cast in the simplest possible format, that of a linear combination of elements. Thus the measured biological value, V, is sought to be explained by a series of terms, A, B, C, etc. as the linear combination: $V = A + B + C + \ldots$. The QSAR approach can be used to relate many measures/properties of molecules which are somehow reflective of their structure, such as partition coefficients and molar refractivity. In the past these indirect measures of shape have been used in QSAR studies since using direct measures of shape proved conceptually and computationally difficult. As the art has progressed, and as the structural differences used in QSAR studies have become primarily molecular shape differences, the field of "three-dimensional quantitative structure activity relationships" (acronymed 3D-QSAR) has evolved.

The 3D-QSAR approach quantifies chosen shape parameters and tests to see if a correlation can be found between those parameters and a biological variable, typically binding affinity. It has turned out to be a very complex problem to model the interaction between a ligand and its receptor. The principal difficulty has been finding a quantitative way in which to express the simple concept of shape. As is often the case, what is visually obvious to the human eye and brain is complex to describe quantitatively or mathematically. While describing shape is difficult enough, searching for similarities in shape using shape descriptors which are, at best, inadequate turns out to be exceedingly difficult.

The general approach used in the QSAR methodology relies on the fact that, for most proteins, there are a number of chemical compounds or substrates having known structural differences which bind with differing affinities to the protein. The rationale behind the 3D-QSAR approach is that it should be possible to derive shape descriptors which, when applied to the various substrates, will reflect the different binding affinities. In 3D-QSAR a similar underlying assumption is made as in other QSAR approaches, i.e., that the relevant biological parameter, usually a binding affinity, can be represented as a linear combination of weighted contributions of the various shape descriptors for the substrate molecules. Once a whole series of substrates are described with the same shape descriptors, it should be possible to compare or correlate the shape descriptors and extract the critical shape determinants found to be associated with the differences in biological activity amongst the substrates.

From a knowledge of the most significant structural shape elements of the substrate or ligand, one could then infer the important elements of the receptor site on the protein. Ideally, in this process one would have at least as many substrates to compare as one had variables among the shape descriptors. Thus, a system of equations with the number of equations equaling the number of shape descriptors with unknown weighting coefficients would exist and could be solved exactly. However, in practice, it quickly became evident that, even with simplifying assumptions, using available shape descriptors to describe the properties of an unknown shape, the number of descriptor variables far exceeds the number of available substrates for which binding data is known. Thus, rather than getting an exact solution, it was found that approximating statistical methods had to be used to extract from the numerical shape descriptors the shape elements which best correlated with observed biological activity. However, until very recently statistical methods were not available which could extract information from a system of equations containing many more variables than equations.

During the past decade work has progressed in this field. From chemical analysis of substrate-protein complexes, it is known that the molecular interactions that produce an observed biological effect are usually noncovalent. Thus, the forces important for intermolecular association are believed to arise from hydrophobic, van der Waals (steric), hydrogen bonding, and electrostatic interactions. Attempts have been made to build shape descriptors based on these properties, but, unfortunately, the immense number of degrees of freedom and large labile protein-substrate complexes make the mathematical modeling of the shape of the complexes extremely difficult. Further simplifying criteria and assumptions were found to be necessary.

One such approach, entitled the Molecular Shape Approach developed independently by Simon, et al. (see Simon, Z; Badilenscu, I.; Racovitan, T. J. Theor. Biol. 1977, 66, 485 and Simon, Z.; Dragomir, N.; Planchithin, M. G.; Holban, S.; Glatt, H.; Kerek, F. Eur. J. Med. Chem. 1980, 15, 521) and Hopfinger, (see Hopfinger, A. J. J. Am. Chem. Soc. 1980, 102, 7196) compares net rather than location-dependent differences between molecules. That is, a shape characteristic of the total molecule is calculated in which the details of specific surface characteristics are merged into an overall molecular measure. The most active molecule in a series (in the sense of biological affinity) is considered to be a template molecule which has an optimal fit to the receptor site in the protein. Differences in activity amongst the series of substrate molecules are, therefore, potentially correlated by a multiple regression analysis with three structure (or shape) parameters definable for each member of the series. The shape parameters initially considered were either: 1) the common volume, 2) the volume possessed by the most active molecule, but not by the less active molecule, and 3) the volume possessed by the less active but not by the most active molecule in the series. Hopfinger describes these parameters as Common Overlap Steric Volumes and interprets them as quantitative measures of relative shape similarity.

More recently Hopfinger (see Hopfinger, A. J. J. Med. Chem. 1983, 26, 990) has constructed a new set of molecular shape descriptors derived from the potential energy field of a molecule. In this approach, Hopfinger uses molecular mechanics potentials as a means of estimating the molecular potential energy fields:

$$P_u(R, \theta, \phi) = \sum_{i=1}^{n} \left[ \frac{a(T)_i}{r_i^6} + \frac{b(T)_i}{r_i^{12}} + \frac{Q_i Q(T)}{\epsilon(r_i)(r_i)} \right]$$

In this equation the molecular potential energy field $P_u(R, \theta, \phi)$ at any given point $(R, \theta, \phi)$ for molecule u is defined; $a(T)_i$ and $b(T)_i$ are the attractive and repulsive potential energy coefficients, respectively, of atom i of molecule u interacting with the test probe T which is treated as a single force center; $Q_i$ and $Q(T)$ are, respectively, the charge densities of the ith atom and the test probe; $\epsilon_{(ri)}$ is the dielectric term; n is the number of atoms in u, and $(r_i)$ is the distance between atom i and the test probe. Hopfinger suggests that pairwise field-difference $[\Delta P_u]$ descriptors may correlate with biological parameters in a 3D-QSAR. Note, however, that this is a net molecular shape descriptor rather than a specific location-dependent shape descriptor.

A second approach is the Distance Geometry Method of Crippen. See for example Ghose, A.; Crippen, G. J. Med. Chem. 1985, 28, 333. In this approach the user must provide a "pharmacophore" or a list of potential receptor-binding atoms on each of the substrates/ligands having specified physicochemical properties. Knowledge of the pharmacophore comes from chemical studies of the binding properties of the given series of substrate molecules. The user must also provide a "binding site", a set of points in Cartesian space which are capable of interacting with a nearby pharmacophore atom, the magnitude of the attraction or repulsion depending on the nature of the atom. The geometrically allowed interactions between the ligand atoms and the binding site are determined. Each ligand is free to move or experience torsional deformations, in any fashion that minimizes the sum of its site points' energies of interaction with the "binding site". Thus, following Crippen, who again assumes a linear function for the interaction, the binding energy of a particular binding mode will be given by:

$$E_{CALCD} = -CE_c + \sum_{i=1}^{n_s} \sum_{j=1}^{n_p} \left[ C_{i'j} \sum_{k=1}^{n_o} P_j(t_k) \right]$$

where $E_c$ is the energy of the conformation; C's are the coefficients to be determined by quadratic programming; i' is the type of site i; $n_s$ represents the number of site pockets; $n_p$ represents the number of parameters to correlate with that site pocket interaction; $n_o$ represents the number of atoms occupying that site pocket; $p_j$ represents the jth physiochemical parameter of the atom of type $t_k$.

A successful 3D-QSAR is found when the sum of the energies of interaction obtained is suitably close to the binding affinities observed experimentally. The result provides both a receptor map (the position and nature of the "binding site" points) and, for each member of the series, an active conformation of that molecule. In both the Hopfinger and Crippen approach, it will be noted that an initial educated guess must be made for the choice of the active conformation of the molecule before the analysis can be done, and Crippen must further hypothesize an actual receptor site map in three dimensions.

Another major problem in any quantitative approach to shape analysis is the fact that, in solution, most compounds exist as a mixture of rapidly interequilibrating shapes or conformers. Generally, it is not even known which of the multiple conformations of a molecule is responsible for its measured biological affinity. Once again, educated guesses must be made to decide which of the many molecular conformations will be used in a 3D-QSAR analysis. The existence of multiple conformations further complicates the task of choosing the correct molecular orientation in which to make the comparison between the substrate molecules. Obviously, the ability of any shape measure to compare molecular shapes relies upon the correct relative orientation of the molecules when the shape measure is first determined. The same molecule when compared to itself rotated by 90° would not likely show any common structural features. Therefore, several of the 3D-QSAR methods rely upon alignment rules to guarantee that only the variable or differing parts of the molecules make the greatest contribution to the shape comparison. It is obvious that the existence of multiple conformations for a given molecule complicates this task.

Typically then, a 3D-QSAR analysis starts out with many shape dependent parameters for a relatively few molecules whose biological activity, such as binding affinity, is known. This results in a series of linear relationships/ equations relating the shape parameters to the biological measures having many more unknowns (columns) than relationships (rows). Except in the limiting cases of shape descriptors where oversimplifying assumptions are made, no statistical regression or correlation methods were available until recently which could give any possible hope of solving such a set of equations.

BRIEF SUMMARY OF THE INVENTION

The present invention is an effective computer methodology employing both interactive graphics and statistical techniques for correlating shapes of molecules with their biological properties. The method of the present invention utilizes a new approach to 3D-QSAR which provides an objective and quantitative measure of the three-dimensional shape characteristics of all areas of a molecule and, at the same time, requires very few limiting assumptions. The quantitative description of the shape of the molecule is derived from an analysis of the steric and electrostatic interactions of the atoms comprising the molecule with a test probe. The resulting interaction energies calculated at all intersections in a three-dimensional grid or lattice surrounding the molecule form the quantitative shape descriptors entered along with the molecule's measured biological activity as a row in a data table.

Each molecular conformation may be similarly described as a row of lattice point energies associated with the same measured biological activity. Selection of the conformers of choice can be made on either an empirical basis or by a weighted average, typically a Boltzman distribution of the various conformations. A row of interaction energies representative of the conformations of a given molecule is then used. The resulting 3D-QSAR table typically has several thousand columns of lattice point energies and a number of rows corresponding to the number of molecules in the series being investigated.

Theoretically, a complete description of the shape differences between the molecules under study is contained in this table, but previously no statistical methodology was available to extract useful information from the table. Unless either limiting assumptions about binding sites are made which reduce the number of columns, or knowledge exists about the specific binding sites of a specific conformation, an infinite number of sets of coefficients can be calculated which would yield the same biological parameter values. Early in the 1980's a statistical methodology was derived which explicitly solves this type of multivariate problem. This methodology is called Partial Least Squares Analysis (PLS).

The software of the present invention permits four different alternative procedures to be used to align the molecules in the three-dimensional lattice. They are: 1) a user specified alignment based on other data; 2) the Fit routine; 3) the Orient routine; and, finally, 4) the Field Fit procedure which minimizes the differences in the calculated fields of the atoms between the various molecules. Preferably the alignment will be done by Field Fit. A 3D-QSAR table is generated and then analyzed according to the PLS method as modified for CoMFA. Resulting solution of the 3D-QSAR table yields coefficients of the column terms which represent the relative contributions of the various lattice positions to the biological activity. Since the solution is re-expressed in terms of interaction energy values similar to those that were calculated in creating the 3D-QSAR table, it is possible to reverse the process and display on a video terminal a plot of the interaction energies to reveal those areas of molecular shape associated with differences in biological activity. In an interactive graphics display environment, the invention allows the user to vary the analytical options and, in a reasonable time frame, see the areas of molecular shape most important to biological activity highlighted on the screen in front of him. By a study of the changing display as the parameters are varied, the user may obtain an understanding of how particular shape characteristics of the molecule are important to its biological activity.

It is a purpose of the present invention to compare the shapes of molecules with shape descriptors highly sensitive to local surface area differences. In addition, it is a purpose of the present invention to provide a methodology for making a quantitative estimate of the importance of the various components of molecular shape to the biological activity of a molecule. A further purpose of the present invention is to provide structural, conformational, and statistical information which will allow users to suggest or identify new molecules which might be used as substrates/ligands. Finally, it is a purpose of the present invention to provide an interactive graphics environment in which the various parameters of shape can be studied in a quantitative fashion in order to obtain a more thorough knowledge of the nature of intermolecular interactions.

DESCRIPTION OF DRAWINGS

FIGS. 5-9 are schematic illustrations of the integration of the CoMFA software into a standard molecular modeling environment.

DETAILED DESCRIPTION OF THE INVENTION

The present invention overcomes the limitations of earlier 3D-QSAR approaches and allows significant insights into molecular interactions never before achieved without actual X-ray crystallographic knowledge of the receptor binding sites. In fact, to the extent X-ray results provide only a static picture, the present invention provides more detailed knowledge of the shape differences operative in dynamic interactions between molecules in solution. The Comparative Molecular Field Approach (CoMFA) is a heuristic procedure for defining, manipulating, and displaying the differences in molecular fields surrounding molecules which are responsible for observed differences in the molecules' activities. This description of CoMFA is arranged in three progressively more detailed sections: first, an overview of the entire process; second, descriptions of the individual components including a rationale for each component and the differences with the prior art; and third, annotated software source code implementing CoMFA.

CoMFA OVERVIEW

Once a series of molecules, for which the same biological interaction parameter has been measured, is chosen for analysis, the three-dimensional structure for each molecule is obtained, typically from the Cambridge Crystallographic Database or by standard molecular modeling techniques. The three-dimensional structure for the first molecule is placed within a three-dimensional lattice so that the positional relationship of each atom of the molecule to a lattice intersection (grid point) is known. A probe atom is chosen, placed successively at each lattice intersection, and the steric and electrostatic interaction energies between the probe atom and the molecule calculated for all lattice intersections. These calculated energies form a row in a conformer data table associated with that molecule.

Interaction energies for additional conformations of the first molecule may be similarly calculated. After each row of interaction energies is calculated for each conformer, the conformer is aligned by a field fit procedure which minimizes the energy differences at each lattice point between that conformer and the first conformer. The field fit interaction energy values for each conformer are then entered into the data table for the first molecule. Once the interaction energies for all conformations of the first molecule have been calculated, an averaged value of the interaction energies at each lattice point of all the conformers becomes the first row in a 3D-QSAR data table associated with the measured biological parameter for the first molecule.

Figure 1:
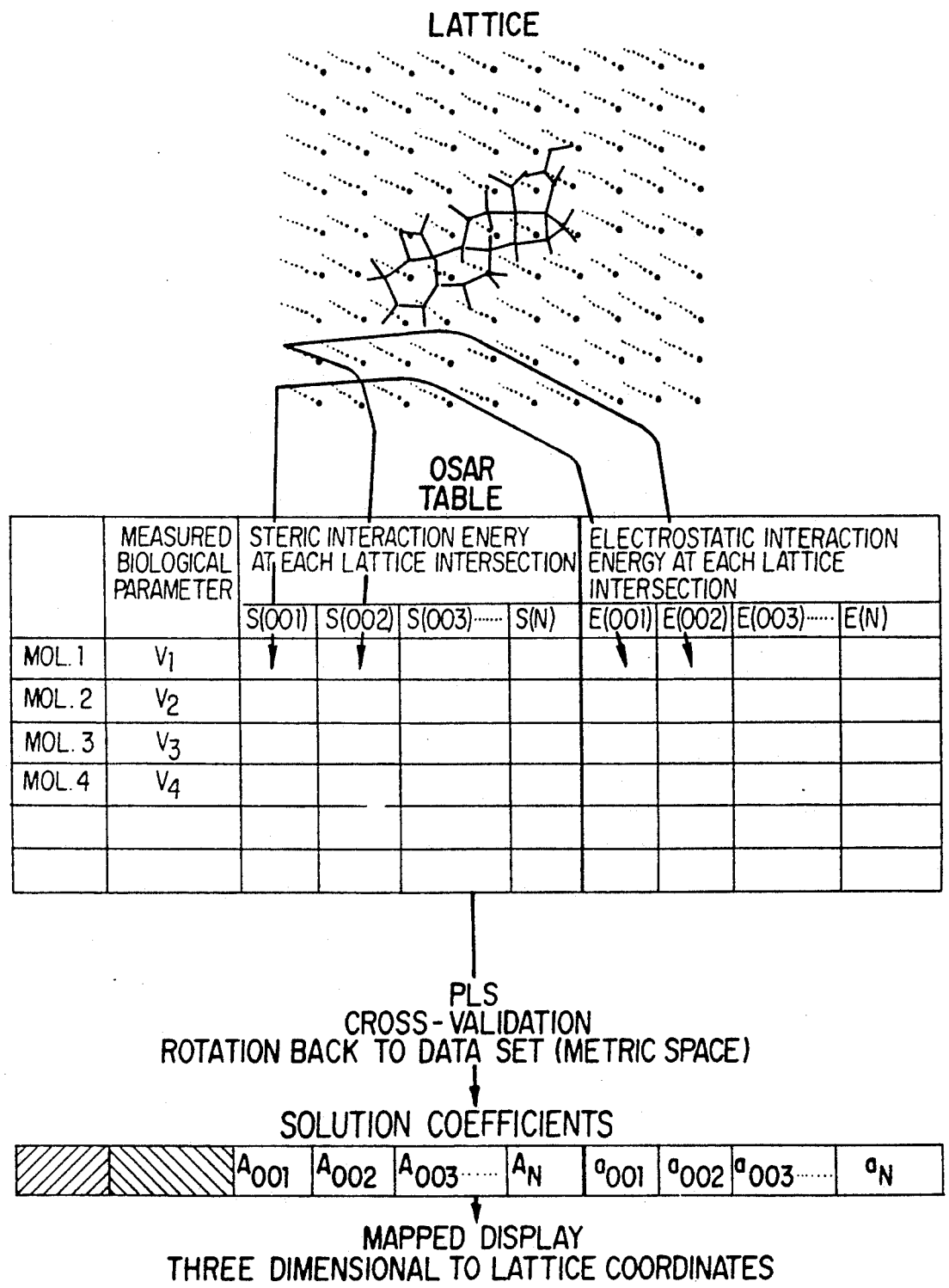
FIG. 1 is a schematic illustration and overview of the CoMFA method.

An identical procedure is followed for all the molecules in the series. After the averaged value over the conformations for a particular molecule is entered into the 3D-QSAR table, a field fit minimization of the newly added data to the first molecule aligns the newly added molecule to the others in the series. The upper portion of FIG. 1 diagrammatically shows how the 3D-QSAR table is constructed. For each lattice intersection, the steric or electrostatic interaction energy with a test probe atom placed at the lattice point is entered into the appropriate steric or electrostatic column associated with that point. The intersection points are numbered sequentially, and the corresponding column identified as steric(S) or electrostatic (E).

Once the data (interaction energies and measured biological activity) for all molecules in the series are entered into the 3D-QSAR data table, a Partial Least Squares (PLS) analysis is performed which includes a cross-validation procedure. Using the interaction energies for each lattice position and the biological values, in essence, PLS solves a series of equations with more unknowns than equations. As shown in the lower portion of FIG. 1, the resulting solution is a series of coefficients, one for each column, the value of which (in energy units) reflects the contribution of the interaction energies at that lattice position to differences in the measured biological parameters.

Figure 3A:
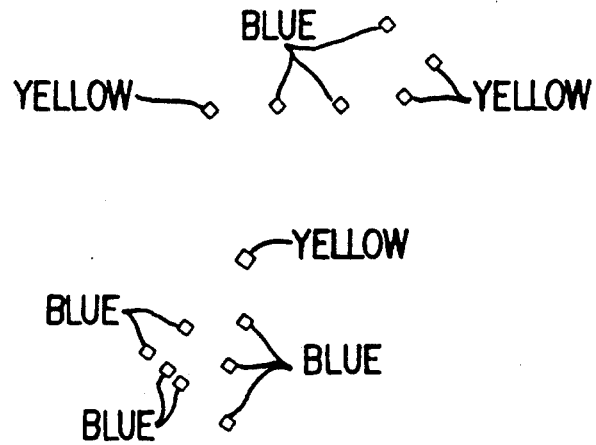
FIG. 3A shows a scatter plot in three-dimensional lattice space of a steric CoMFA solution.
Figure 3B:
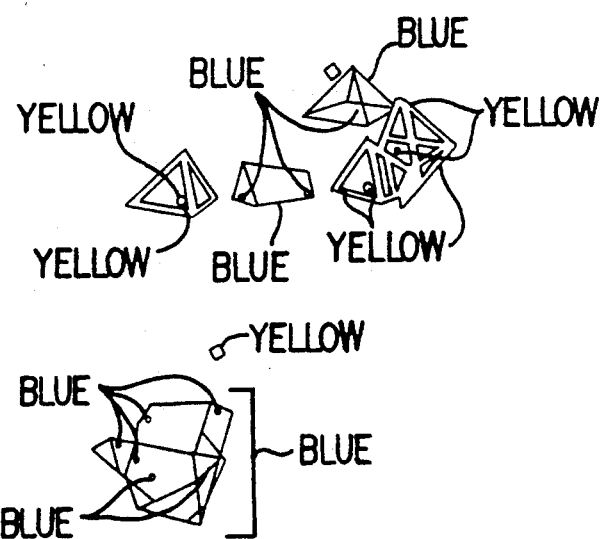
FIG. 3B shows a contour plot in three-dimensional lattice space of the same CoMFA solution shown in FIG. 3A.

While the solution has many terms, the one-to-one correspondence between a term and a lattice point allows the solution to be presented as an interactive color-coded three-dimensional image, either in the form of a graph visually similar to the top part of FIG. 1, (see FIG. 3A) the color of a point signifying the magnitude of the corresponding terms, or better, with term values summarized in contour form (see FIG. 3B). The graphic representation clearly shows the area in molecular space where the 3D-QSAR strongly associates changes in molecular field values with changes in the measured biological parameter.

MOLECULAR FORCE FIELDS

As pointed out above, biochemists and biophysicists have come to believe that intermolecular interactions are highly stereo specific, depending mainly on shape complementarity, and that biological molecules solve a three-dimensional jigsaw puzzle every time they bind. However, the prior art 3D-QSAR shape descriptors mentioned earlier give only a net measure of overall shape, totally averaging out local topological differences between molecules. These methods are actually aggregate indices, which describe a "shape" only to the same extent, for example, that the comparative "shape" of two sculptures is described by measuring their differential weight or volume. Likewise, ball and stick molecular models do not reflect either the steric interactions of extended molecular orbitals or charge associated interactions.

In order to describe molecular shape, a descriptor should be sensitive to at least three molecular parameters: first, it should account for the true steric bulk of each atom in the molecule; second, it should account for electrostatic interactions of each atom in the molecule; and, third, it should be a fine enough measure to reflect every local topological feature of the molecule. The approach used in CoMFA is that a suitable sampling of the steric and electrostatic interactions of a molecule will suffice to answer most questions about its possible shape dependent receptor interactions. The calculation of interaction energies at lattice points surrounding a molecule is not, in itself, new. Others have tried to use this approach as an estimate of molecular shape. For example, Goodford has described the use of probe-interaction "grids" similar to those calculated in the present invention. See Goodford, P. J. J. Med, Chem. 1985, 28, 849.

In theory, the row of interaction energy data generated from all lattice points contains most of the information describing how a molecule "looks" to a receptor in three dimensions. However, before this invention, no one has discovered how to compare the shapes of different molecules represented by these rows of data or to extract and visualize useful information about the shape differences which are important to molecular associations.

The fineness or resolution with which the shape of a molecule is described by this method depends on three factors: 1) the steric size of the test probe atom, 2) the charge on the test probe atom, and 3) the lattice spacing. The software of the invention allows the user to specify both the steric size and charge of the test probe. In addition, the probe parameters may be varied at different lattice locations which the user believes calls for finer or coarser measurements. The user may also select the lattice spacing. Typically probe atom size is varied from that of covalent hydrogen —H, to $sp^3$ carbon, to $sp^3$ oxygen, to divalent sulfur. The probe charges used typically are $+1.0$ and $0.0$, while lattice spacing values of 1.0 to 4.0 angstroms are frequently employed.

Van der Waals radii are generally used for the steric calculation and atomic charges can be calculated from knowledge of atomic coordinates. Thus, the steric interaction energy is calculated as:

$$\sum_{i=1}^{N_{at}} \left[ \frac{A_i}{r_i^{12}} - \frac{B_i}{r_i^6} \right]$$

where $N_{at}$ is the number of atoms in the biomolecule; $r_i$ is the distance between the probe atom and the ith atom in the biomolecule; and $A_i$ and $B_i$ are constants characteristic respectively, of the probe atom type and the type of the ith atom in the biomolecule. [Other values can be selected by the user as an option in place of the exponent 12- see Software Disclosure.] The electrostatic interaction energy is calculated as:

$$\sum_{i=1}^{N_{at}} \frac{Q \, q_i}{r_i^2}$$

where the $N_{at}$ and $r_i$ are the same as for the steric calculation; Q is the charge on the probe atom; and $q_i$ is the charge on the ith atom. The $q_i$ may be calculated by the method of Gasteiger and Marsili. See Gasteiger, J.; Marsili, M. Tetrahedron 1980, 36, 3219. [The user may omit the exponent 2 as a user option—see Software Disclosure.] Since the probe atom is placed successively at all lattice points, for those points within the molecule the steric repulsion values can become enormous. Since there is no significance to the absolute value other than to estimate how much atomic volume overlap exists, whenever the probe atom experiences a steric repulsion greater than a "cutoff" value (30 Kcal/mole typically), the steric interaction is set to the value "cutoff", and the electrostatic interactions are set to the mean of the other molecules' electrostatic interactions at the same location. These cutoff values may also be selected by the user of the programs. Obviously no topological information is lost.

It should be recognized that any property which can be calculated from a molecular model, such as interatomic distances or torsion angles, can become an additional column in the 3D-QSAR table. Columns may also contain values of other molecular parameters (such as logP or heats of formation), data defined as functions of other columns, or even data that is calculated via custom procedures provided by the user. In addition, since measured biological activity is a consequence both of a molecule's ability to get to the receptor site as well as to bind to the receptor, additional terms (columns) which reflect molecular diffusion may be incorporated. It should be appreciated that the statistical and visual correlation of data in the columns by the methods of the present invention is not limited to interaction energy shape descriptors.

In fact, a most significant and powerful feature of the present invention is that the CoMFA method will yield information not even available from X-ray crystallographic studies since X-ray results present static pictures which are not totally dispositive of the dynamic interactions in solution. By comparison, the CoMFA model of the interaction is phenomenological. The actual measured activity is expressed or predicted in terms of determinable quantities. The present invention will display the dependence of the measured biological parameter on data (shape and other relevant information) contained in all columns.

For development of the present invention, all positioning of molecules in the lattice was done with the SYBYL program of Tripos Associates, Inc. References to SYBYL data structures can be seen in the source code. However, there are several other programs available which are functionally equivalent and may be used with the present invention. Examples are:

ChemX—from Chemical Design Ltd., Oxford, UK
Insight—from BioSym Technologies, San Diego, Calif.
Quanta—from Polygen, Waltham, Mass.
ChemLab—from Molecular Design Ltd., San Leandro, Calif.
MacroModel—from Prof. Clark Still, Columbia Univ.

Such a host program must support the building and storage of molecular models (retrieval of the atomic coordinates) plus the calculation of atomic charges (for electrostatic field computation) and the tabulation of steric parameters by atomic type (for steric field computation).

A list of the data structures required by all CoMFA programs is presented as Q3DEF.C and DABDEF.C to facilitate the integration of other programs with CoMFA.

ALIGNMENT AND FIELD FIT

CoMFA works by comparing the interaction energy descriptors of shape and relating changes in shape to differences in measured biological activity. Since the shape descriptors are calculated at each lattice point, the lattice site-specific interaction energies calculated for the same molecule offset by even one lattice point will be significantly different. A CoMFA analysis of this data will show differences in shape where there are none. Therefore, the positioning of a molecular model within the fixed lattice is by far the most important input variable in CoMFA since the relative interaction energies depend strongly on relative molecular positions within the lattice.

The Field Fit feature of the present invention aligns molecules to minimize their field differences rather than atomic coordinate differences. Since the interaction energies reflect molecular shape, they can be quantitatively manipulated for shape alignment. This is a particularly suitable approach since the intermolecular comparisons are based on these same energy fields.

In Field Fit, any molecule may be used as the reference. However, if fitting conformations of the same molecule, the conformation which from other considerations is most likely to be the most active conformer would usually be used as the comparison standard. When Field Fitting the final series of test molecules, the molecule with the greatest biological activity would usually be used as the reference. In the Field Fit alignment, the root means squared (RMS) difference in the sum of steric and electrostatic interaction energies averaged across all lattice points, between the new molecule and the reference molecule or set of molecules, is minimized with respect to the six rigid-body degrees of freedom, any user-specified torsion angles, and any change in internal geometry. The user has the option before Field Fitting of weighting those lattice positions which he believes form other considerations may be particularly significant to the alignment of a given molecular series or conformation. The results of Field Fit alignments or test alignments using weighting factors may be displayed and compared visually as three-dimensional scatter or contour plots in the same manner as discussed later for all graphic output.

With reference to the 3D-QSAR table of FIG. 1, Field Fitting molecule 2 to molecule 1 would correspond to minimizing the sum of squared differences between the values in all but the first column of the first and second rows of the table, by altering the position and/or torsion angles of molecule 2. Field Fit also requires for satisfactory results a steric repulsion beyond the lattice boundary and, when torsion angles are varied, the conventional molecular mechanics internal energy calculated using the same force field. The reason for the boundary steric repulsion is as follows. The function being minimized can be visualized as being similar in shape to the cross-section of a volcano. The steric boundary repulsion is needed because the answer sought in the minimization is the crater, but if the molecules are not nearly aligned or field-fit to begin with, the down-hill (minimization) direction will be down the outside of the volcano: that is, minimization of the difference in fields will push the molecules apart. By placing steric repulsion at the edge of the lattice region, the down-hill direction along the outside of the volcano will be disfavored.

Field Fit also allows the user to address the relative weighting of the three different contributions to the function being minimized, namely; the field difference itself, the edge steric repulsion, and the differing internal energies as torsional bonds and other internal geometries are altered. The weighting choice is a user option in the program. The Field Fit ability to see in an interactive graphics environment the three-dimensional consequences of various weighting choices on molecular alignment is in itself a significant advance in 3D-QSAR. Minimization is performed by the Simplex method (a widely available algorithm), with step sizes such that individual atoms initially move no more than 0.2 Angstroms. The Simplex method is preferred because the function being minimized does not have analytical derivatives. Convergence occurs when successive function evaluations vary less than 1%. As with any minimization, Field Fit will find a best alignment if the final geometry is expected to closely resemble (be "downhill" from) the starting geometry.

The CoMFA programs allow other alignment procedures to be followed, such as the standard Fit and Orient routines. For instance, Fit utilizes least squares superposition of user specified sets of nuclei of atoms, with or without relaxation of internal geometry, while Orient takes three user specified atoms and places the first atom at the origin, the second atom along the x axis, and the third atom in the xz plane. The user may even attempt trial and error alignment based on an educated guess or other 3D-QSAR data. Field Fit is particularly useful when a CoMFA based upon some other alignment method gets too low a cross-validated $r^2$, caused in turn by one or more molecules having very large residuals (a very large difference between predicted and actual properties in the cross-validation step). A Field Fit of the compound(s) with very large residuals should produce a new alignment which will lead to improvement when the CoMFA is repeated.

The Field Fit procedure also has important applications when used to maximize rather than minimize field differences. If the differences in the interaction energies of two shape complementary molecules are maximized, Field Fit will produce the best three-dimensional alignment or "docking" between the molecules. Thus, if the structures of both the substrate and enzyme (or antigen and antibody) are known, Field Fit will find their optimal alignment.

CONFORMATION SELECTION

A major unsolved problem in prior art approaches to 3D-QSAR is the determination of the proper molecular conformation to use in an analysis. Absent any direct knowledge of the actual active conformation responsible for biological activity, previously the only approach has been to make an educated guess. CoMFA, using Field Fit, allows a quantitative approach to conformation selection. It is possible using the CoMFA Programs to enter into a separate data table the interaction energies of every conformer and fit it to a selected template conformer. Various averaging or weighting schemes can then be employed as user options to determine a most representative conformer. The interaction energies for the various conformations can be weighted based on reasonable assumptions about the likelihood of certain conformations being most active without totally excluding contributions from presumably less active forms. In the alternative, since most conformations are believed to be equilibrated in free aqueous solution at normal temperatures, the CoMFA programs permit the weighting to reflect a Boltzman distribution over the energy of the conformers. Only in the case of a highly labile molecule (one possessing multiple rotomers and tautomers) would a Boltzman distribution produce a fuzzy, averaged, and meaningless ball. CoMFA with Field Fit provides the ability to use these various weighting functions to determine a form of the molecule which the receptor site is most "likely" to see.

PLS—PARTIAL LEAST SQUARES ANALYSIS

As mentioned earlier, the inherently underdetermined nature of a 3D-QSAR table with many more columns than rows has previously posed an insolvable problem which prohibited use as a shape descriptor of the interaction energies calculated at thousands of lattice points. The values in the data table can be viewed as a system of equations with many more unknowns than equations. For instance, for three molecules the following three equations can be written:

$$\text{Value}_1 = b^1 + A_{001}S^1(001) + A_{002}S^1(002) + \ldots$$
$$A_N S^1(N) + a_{001}E^1(001) + a_{002}E^1(002) + \ldots$$
$$a_N E^1(N)$$

$$\text{Value}_2 = b^2 + A_{001}S^2(001) + A_{002}S^2(002) + \ldots$$
$$A_N S^2(N) + a_{001}E^2(001) + a_{002}E^2(002) + \ldots$$
$$a_N E^2(N)$$

$$\text{Value}_3 = b^3 + A_{001}S^3(001) + A_{002}S^3(002) + \ldots$$
$$A_N S^3(N) + a_{001}E^3(001) + a_{002}E^3(002) + \ldots$$
$$a_N E^3(N)$$

where the Values are the measured biological activities for each molecule; $b^x$ is the intercept for each equation for molecule x; $A_{--}$ and $a_{--}$ are the coefficients of the steric and electrostatic terms which reflect the relative contribution of each spatial location, the subscripts indicating both different coefficient values and the lattice positions with which the values are associated; $S^x(N)$ and $E^x(N)$ are the steric and electrostatic interaction energies calculated at lattice position N (where N ranges from 1 to the maximum number of lattice intersection points) for molecule x. The partial least squares (PLS) method of multivariate analysis "solves" this apparently underdetermined system of equations by a series of orthogonal rotations in hyperspace of both the independent and dependent variable matrices, in each rotation maximizing the commonality between the independent and dependent variable matrix. (In contrast, classical least-squares regression rotates the independent variable columns individually and independently, rather than together, thus consuming a degree of freedom for each coefficient estimated.) The solution to the equations found by PLS is the set of values of the coefficients which come closest to making each equation true. PLS is particularly attractive for CoMFA since it involves only two vector-matrix multiplications, can perform the calculation on raw data, and can solve large problems on a smaller computer.

An important improvement of PLS for use in CoMFA has been created in which the initial PLS solution is rotated back into the original data space thereby re-expressing the term coefficients obtained as the solution in terms of the original metric space (in this case, energy values). Since this solution contains a potentially non-zero coefficient for each column in the data table, (in fact two for each lattice point), it can therefore be displayed and contoured in three-dimensional space, just like any other expression associating numerical values with known locations in space.

Integral to finding a "solution" by PLS is a cyclic cross-validation procedure. Cross-validation evaluates a model not by how well it fits data, but by how well it predicts data. While useful in many situations, cross-validation is critical for validating the underdetermined CoMFA 3D-QSAR tables. A statistical measure of the reliability of the PLS solution is calculated by defining a cross-validated (or predictive) $r^2$ analogously to the definition of a conventional $r^2$ as follows:

$$\text{cross-validated } r^2 = \frac{SD - \text{Press}}{SD}$$

where SD is the sum over all molecules of squared deviations of each biological parameter from the mean and PRESS (predictive sum of squares) is the sum over all molecules of the squared differences between the actual and predicted biological parameters. A negative cross-validated $r^2$ will arise whenever PRESS is larger than SD, that is, whenever the biological parameters are better estimated by the mean of all measured values than by the solution under consideration.

Figure 2:
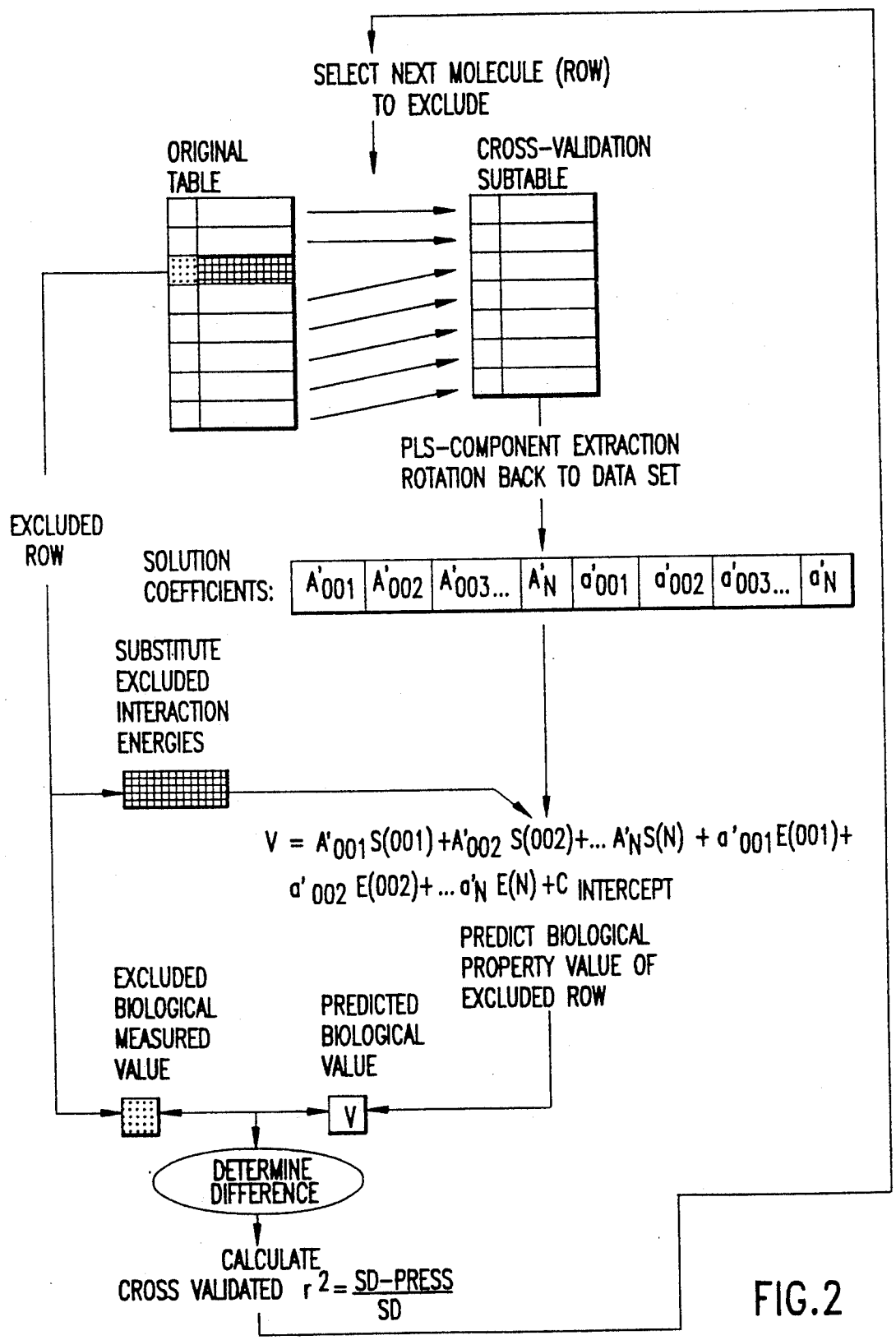
FIG. 2 is a schematic illustration of the cross-validation procedure.

The cross-validation procedure is integrated with PLS as follows. First the entire 3D-QSAR data table is analyzed by PLS and one component extracted in hyperspace. [The projection of this component onto all the orthogonal planes in hyperspace yields components on all the planes which are the equation coefficients sought.] A value of $r^2$ is calculated. The PLS analysis is then repeated (the equation coefficients rederived) with a randomly chosen molecule (row) excluded. The resulting coefficients are used to calculate (predict) the biological value for the excluded molecule (row) and a new $r^2$ is calculated. [In actual practice the program also permits the exclusion of random subsets of molecular values and calculations of the excluded biological values. This reduces the time necessary to compute a first set of coefficients. In a full detailed analysis, each molecule (row) is individually excluded.] This omission, rederivation, and prediction procedure is repeated until every biological parameter value has been predicted by a set of coefficients from whose derivation it was excluded. FIG. 2 shows a schematic outline of this cross-validation procedure. Note how the solution coefficients derived by PLS without the excluded row are used with the interaction energy values from the excluded row in the equation to predict the biological value of the excluded molecule.

Values of $r^2$ and PRESS are calculated for each cross-validation cycle. If there is no correlation amongst the data, the coefficients derived will not give meaningful predicted values and the PRESS will exceed the SD. The $r^2$ values indicate how good the components are that result from the extraction.

Next, the contribution of the first component already obtained is removed from the matrix hyperspace, a second PLS analysis performed, and an additional component extracted. Another cross-validation round is completed, again completing the omission, rederivation, and prediction cycle. The user specifies the number of times the extraction cross-validation procedure is repeated. The extracted components are added, rotated back into the data space, and the resulting coefficients generated.

The outcome of the PLS/cross-validation analysis of the data table is a set of coefficients (one for each column in the data table) which, when used in a linear equation relating column values to measured biological values, best predict the observed biological properties in terms of differences in the energy fields among the molecules in the data set, at every one of the sampled lattice points.

GRAPHIC DISPLAY

The final step in a CoMFA is the display of the analytical results in a manner meaningful to the biochemical researcher. In general, the human eye and brain is much more skillful in recognizing complex patterns within a picture than within a table of numbers. CoMFA outputs are uniquely able to utilize this inherent advantage in graphical presentations since the three-dimensionality of the input data is retained throughout. Indeed, the chemists who will use CoMFA are among the most visually oriented classes of scientists. Thus, in addition to its power, CoMFA is also much more graphically oriented than other 3D-QSAR approaches, in both its input requirements, (molecular models), and its output, (scatter plots and contour maps). Literally, the only number with which the end-user needs to be concerned is the cross-validated $r^2$, the figure-of-merit for a CoMFA analysis.

It should be evident that due to the manner in which the CoMFA 3D-QSAR methodology is structured, that is, as an attempt to relate differences in biological activity to differences in shape, the commonly shaped areas among the test molecules should not contribute strongly to the solution. Similarly, not all areas of shape difference should be reflected in larger contributions in the solution, but only those areas of shape difference related most strongly to the biological differences. A significant achievement of the present invention is that its solution to the 3D-QSAR interaction energy data table provides a quantitative comparison of molecular shape. Also, because the PLS solution was rotated back into the data set, the determined coefficients have the same units as the data values, and therefore, each term represents its contribution to functionality in the same units from which it was derived, i.e., interaction energies. In general, the larger the magnitude of a coefficient, the more strongly its associated spatial position is related to the observed biological differences. The sign of the coefficient is related to the sign of the effect of the change on the biological difference.

Further, the terms in the solution are uniquely associated with positions in three-dimensional space (lattice coordinates) since the solution preserves the column structure of the data table. Therefore, a graphic plot in three dimensions of the terms values (lattice point by lattice point) results in a display of the regions in space most responsible for predicting changes in molecular functionality.

For comparison and study, several values representative of each term may be displayed for each point:
1) the standard deviation of the column values times the 3D-QSAR coefficient;
2) the 3D-QSAR coefficient only;
3) the standard deviation of the column only;
4) the column value for one of the molecules;
5) the column value for a molecule times the 3D-QSAR coefficient; or
6) any data from an external file.

The values for steric and electrostatic terms may be displayed separately or in combination.

Figure 4A:
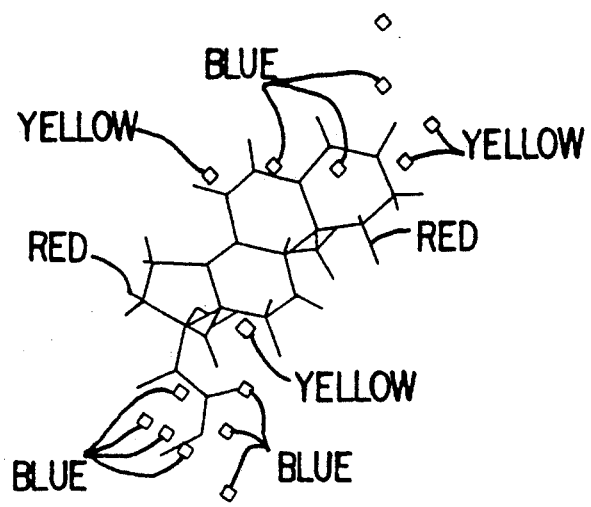
FIG. 4A is the scatter plot of FIG. 3A with a molecule superimposed so that the three-dimensional relationship of the molecule to the CoMFA solution can be seen.

Two methods of graphic presentation are utilized. First the terms can be presented as a three-dimensional scatter plot color coded to represent the magnitude and sign of the association between the energy field change and biological activity at each lattice point. Thus, in FIG. 3A, the blue dots represent solution coefficients whose values indicate that nearby increases in molecular size would increase molecular binding, while the yellow areas indicate that nearby increases in size would decrease molecular binding. The molecular modeling program used originally to place the molecules into the lattice may be used to superimpose any one of the molecules from the data set onto the three-dimensional display so that the colored areas of significance may be more easily identified with specific atomic positions as is shown in FIG. 4A.

Figure 4B:
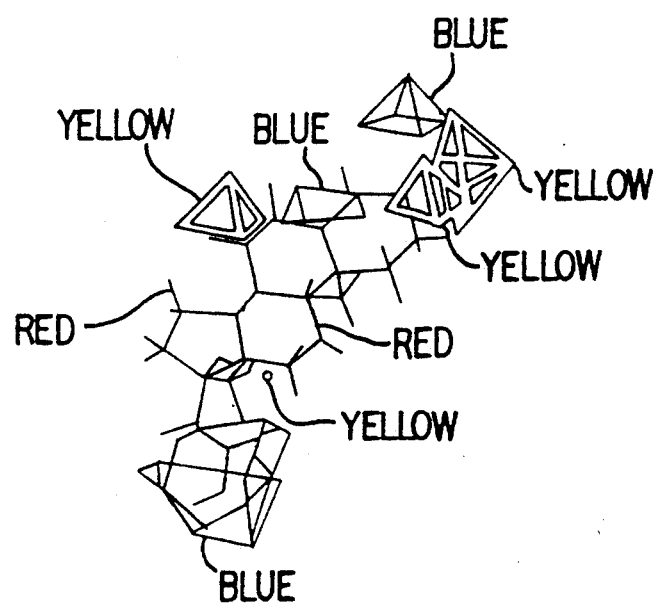
FIG. 4B is the contour plot of FIG. 3B with a molecule superimposed so that the three-dimensional relationship of the molecule to the CoMFA solution can be seen.
Figure 6:
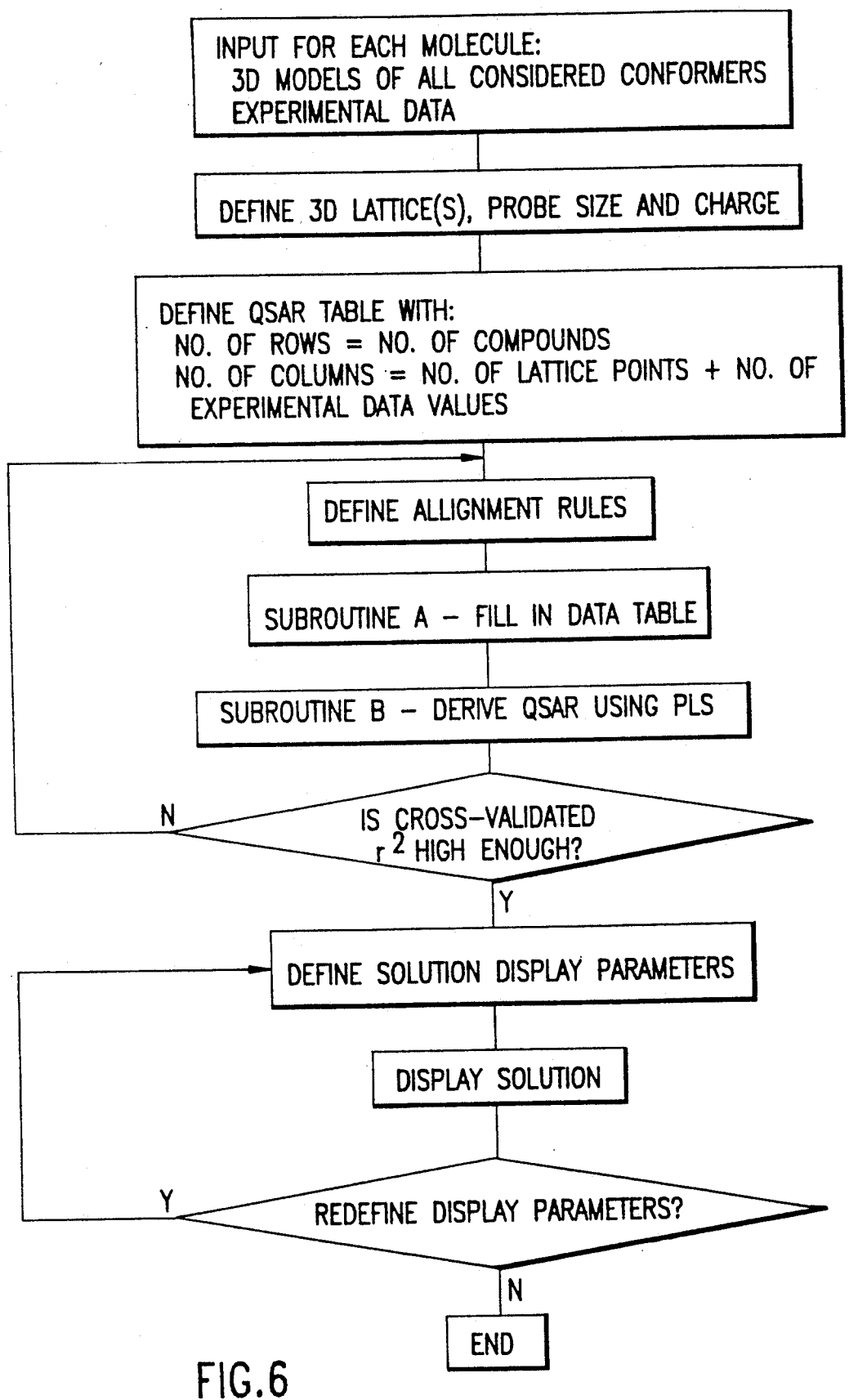
Figure 7:
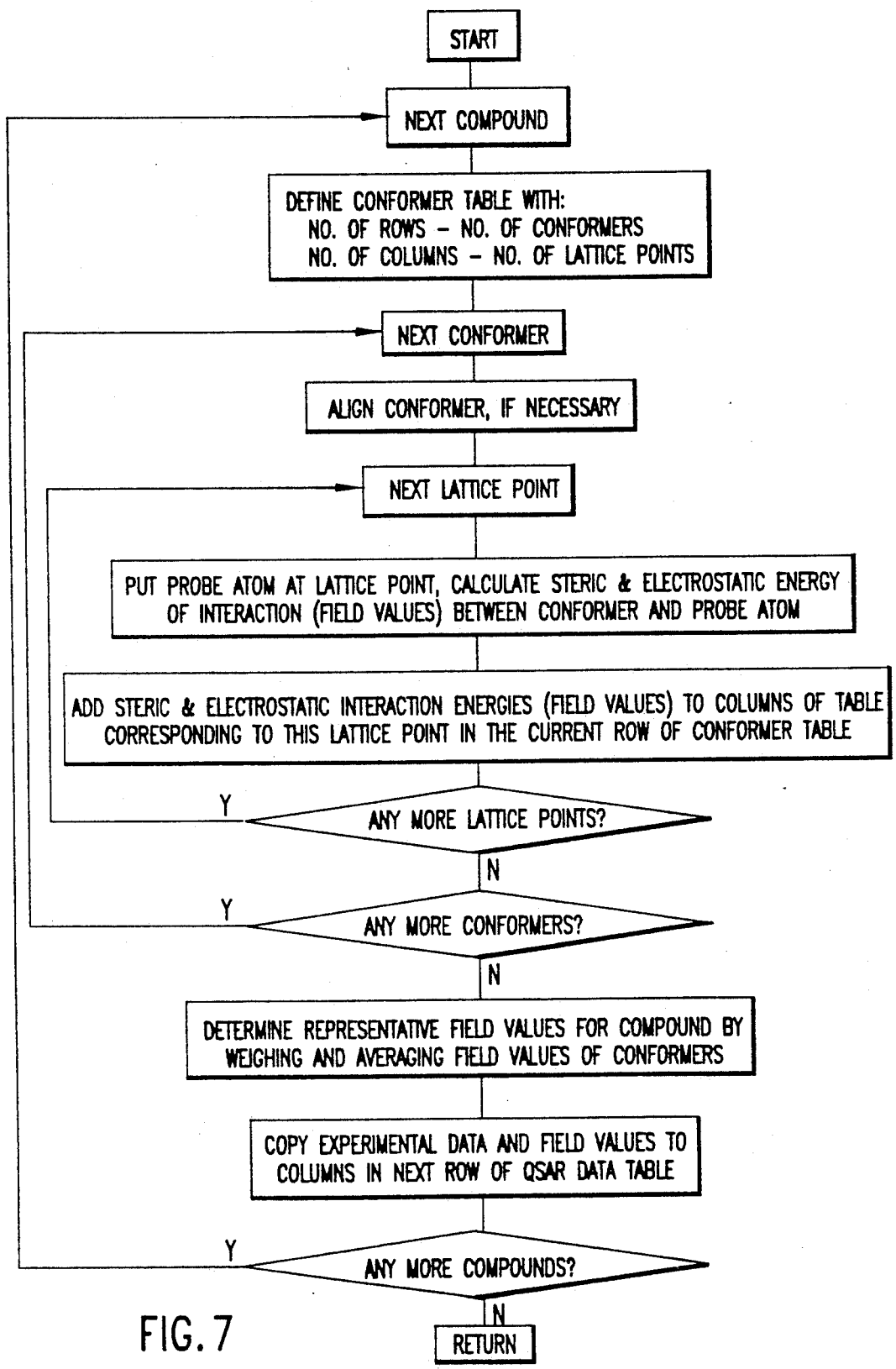
Figure 8:
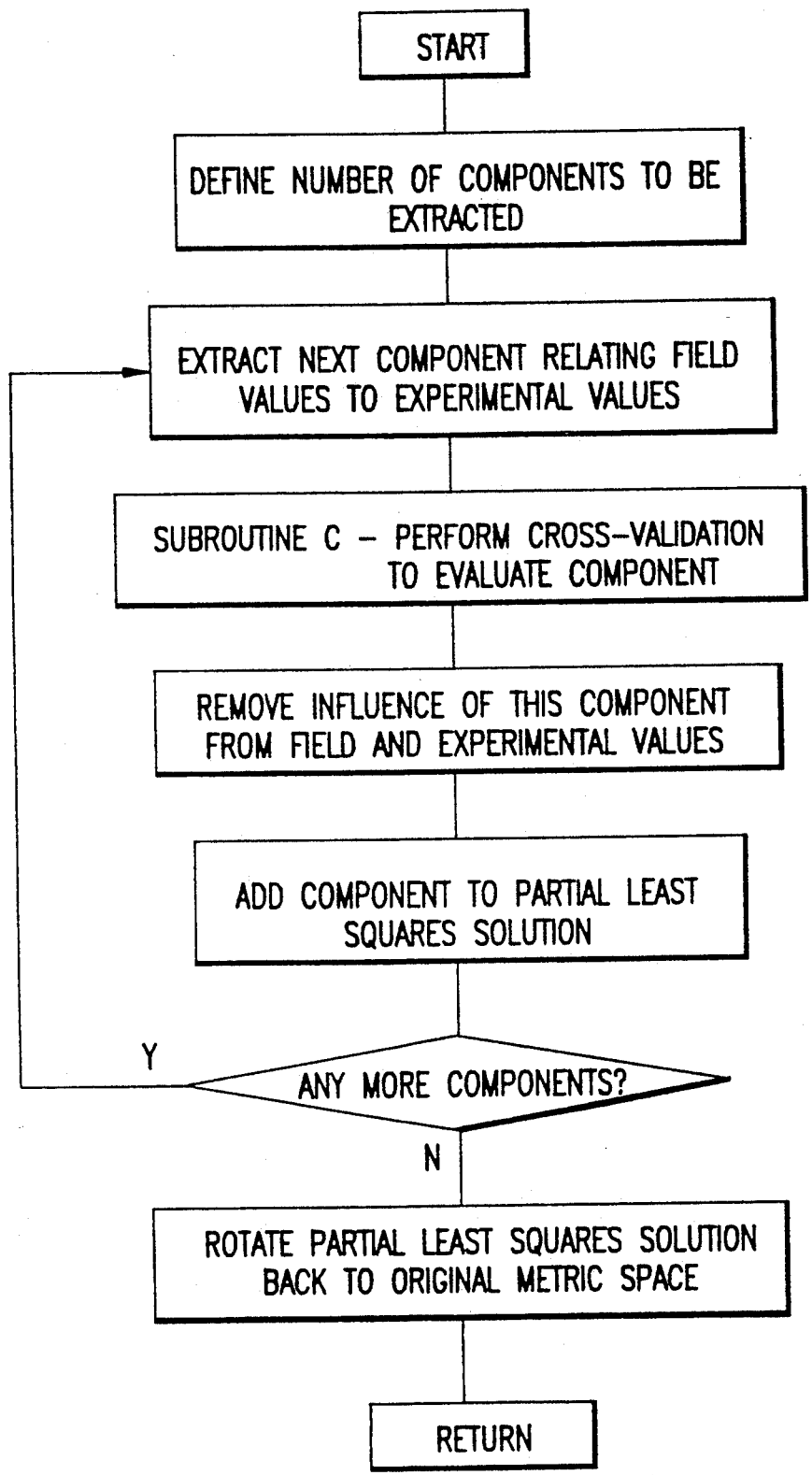
Figure 9:
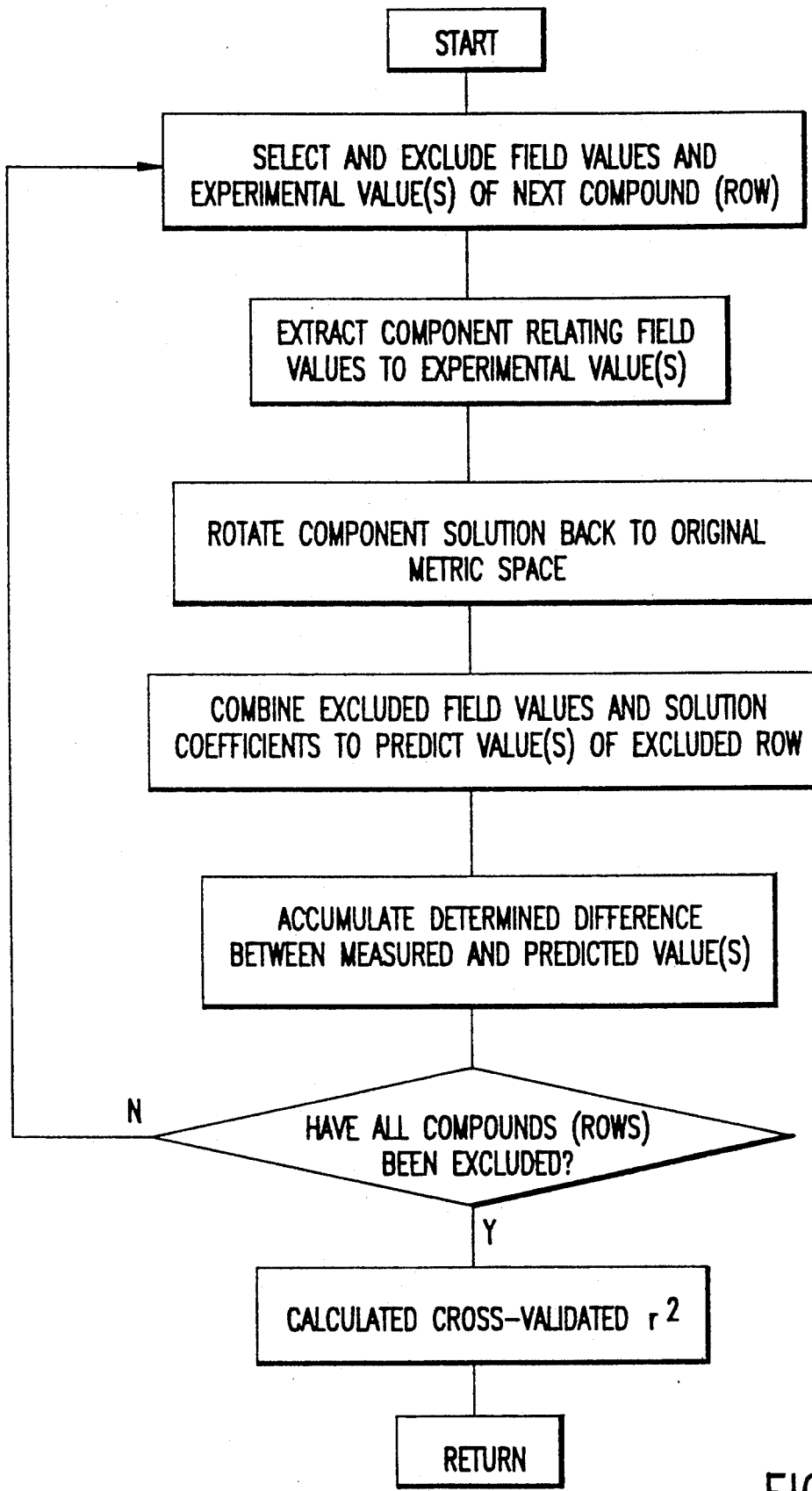

The second method of viewing the information is to plot contours in space. The contour lines connect points (terms) in lattice space having similar values. The contours form polyhedra surrounding space where the values are higher or lower than a user selected cutoff value. The colored polyhedra in each map surround all lattice points where CoMFA strongly associates changes in field values with differences in the biological parameter. FIG. 3B shows a contour plot by itself while FIG. 4B shows a contour plot with a molecule from the data set superimposed for study and comparison.

These displays clearly show the user where either increased steric bulk or increased electrostatic interaction in a region is related to greater biological affinity. Conversely, also shown are those areas where increasing steric bulk or increasing electrostatic interaction interfer (negatively relate) with biological affinity.

One can view CoMFA maps not only as three-dimensional representations of molecular shapes which are significantly related to biological functionality, but also as maps of the receptor spaces. In this view, the higher interaction areas reflect sterio specific orientation requirements of the receptor. The map of the steric terms gives an indication of the steric requirements of the receptor site, and the map of the electrostatic terms gives an indication of the electrostatic requirements of the receptor site. When combined with chemical knowledge of the receptor site derived by other means, this information can lead to interesting and predictive insights into the nature of the receptor site. This method is clearly distinguished from the prior art, such as the distance geometry method, in that no guess as to specific locations of atoms at the receptor site is needed before the 3D-QSAR is determined. In CoMFA, steric specific and electrostatic specific information about the receptor site is derived from the 3D-QSAR. One caution must be mentioned about over-interpreting the contour coefficient map as a receptor map. In a highly underdetermined system such as is used in CoMFA with many times more coefficients to be evaluated than compounds, a number of 3D-QSAR solutions to the data set may exist equally consistent with any given set of compounds and data. While this does not diminish the predictive ability or solution found by the PLS/cross-validation method, it would suggest some caution be utilized in interpreting the final map as a receptor site map.

Finally, the CoMFA map may be rotated and viewed from any desired angle in order to more thoroughly appreciate the space specific information it contains.

PREDICTIVE POWER

A significant advance achieved by the present invention over the prior art is the ability to quantitatively predict the likely biological behavior of a molecule not included in the initial data set. A major impetus for developing 3D-QSAR to describe intermolecular associations, is that such an understanding should enable the design of molecules with even higher biological affinities than those presently known. One application of this ability would be the design of new and more powerful/selective drugs. In the prior art, to the extent that suggestions as to modified molecular structures could be made based on the results of QSAR analyses, it was necessary to synthesize the suggested molecule and test it in the relevant biological system before knowing whether a desired change had been achieved. By comparison, the present invention allows immediate testing of proposed molecular modifications against the CoMFA model-solution. Thus, based upon the spatial areas shown by CoMFA to be significant to biological activity, a new molecular configuration can be proposed. The proposed molecule can be placed and aligned in the lattice structure, its interaction energies calculated, and those energies entered into a 3D-QSAR equation using the coefficients derived from the original data table. The equation yields a predicted biological value for the molecule.

The calculated interaction energies for the proposed molecule can also be displayed and compared to the initial CoMFA spatial maps. One can immediately see on the resulting display whether the changes made in the molecule design are associated with the same higher interaction energy terms and spatial areas as those predicted from the CoMFA. It has been found that the CoMFA methodology predicts with high accuracy the biological value of proposed molecules in those cases where the molecules have been synthesized/tested or were unknown when the CoMFA analysis was done. Thus, the present invention provides a quantitative process for investigating the structures of unsynthesized molecules to determine their likely biological activity. The importance of this ability to all aspects of medicinal and biological chemistry can hardly be overstated.

In addition, the CoMFA methodology will permit the retrieval of molecules with desired structures from among data bases of molecules whose shapes are described by interaction energies. Indeed, it may be found that unsuspected molecules, never tested in a given biological system, may possess the proper shape to interact as well as or better than the known molecules.

CoMFA results can also direct the user towards determining the actual conformer involved in the molecular interaction. As noted earlier, the final CoMFA display identifies those spatial volumes most highly associated with differences in biological activity. The user may superimpose any of the molecular conformations, either as stick models or in interaction energy form, used in generating the 3D-QSAR table onto the solution display to compare the shape of that conformation to those critical spatial volumes.

To an extent, some correlation must exist since the solution is derived from a table containing all conformations. However, the conformation which comes closest to matching the requirements of the solution space can be used as the principal conformation in generating another 3D-QSAR table. If the predictive $r^2$s for the new table solution are higher than for the first solution, the chosen conformation is more likely to be the active conformation. This procedure may be repeated as many times as the user feels necessary.

It will be possible with the process of the present invention to substantially reduce the trial and error approach to drug design with consequent savings of time, energy, and money. Extensive use of CoMFA should also lead to more rapid development of life-saving drugs. As mentioned earlier, CoMFA can be used as well for other types of intermolecular associations such as studies in antigen antibody binding and changes in the receptor site of genetically altered enzymes. All that is needed is some knowledge of the molecular environment involved such as the X-ray crystal structure of the enzyme and knowledge of how substituted amino acids fit into the X-ray structure. The discussion of the present invention in terms of substrate-enzyme binding affinities should be understood to be representative of the utility of CoMFA as it is appreciated at the moment, but not in any way limiting of the generality of the methodology or process disclosed in this invention. Indeed, the spatial maps generated are such an extraordinarily powerful tool in investigating intermolecular associations that it is believed the full import of the process is yet to be fully realized.

SOFTWARE DISCLOSURE [See Appendix]

The present invention is intended to be utilized in conjunction with one of several molecular modeling environments now commercially available. These environments have different hardware and display capabilities, as well as different software modalities available. Typically, however, the computing and display functions equivalent to that found in the Evans and Southerland Series 300 molecular modeling units would be most helpful in practicing the present invention.

Six source code listings are provided: Q3DEF.C, DABDEF.C, EVAL.C, FFIT.C, PLS.FOR, and MAP.C. All source code is in the C language except for PLS.FOR which is in Fortran. FFIT.C, EVAL.C, PLS, and MAP.C are programs while Q3DEF.C is a data description of all data for which the CoMFA programs look, and DABDEF.C contains the global data structures for software which manages tables of numbers.

FIGS. 5-9 schematically show how the CoMFA programs are integrated into a standard molecular modeling environment. As mentioned earlier, several programs are commercially available which can be used to build molecules of interest and their conformers into three-dimensional lattice space although the Tripos Associates, Inc. program SYBYL was used by the inventor. Similarly, while the inventor used the Tripos Associates, Inc. program DABYL to manage tables of numbers, functionally equivalent software includes RS/1 from BBN Software in Cambridge, Mass.

The methodology of the present invention provides for selection of input options/parameters by the user. The data structures for the input options/parameters are specified in Q3DEF.C while DABDEF.C specifies data structures for the data management program. EVAL.C creates a 3D-QSAR table from the information provided by the molecular modeling program and from the input of biological parameters. FFIT.C performs the Field Fit alignment procedure to properly align molecules, either conformers or the molecules in the tested series. PLS.FOR performs the Partial Least Squares Analysis and cross-validation of the 3D-QSAR table created by EVAL.C. Finally, MAP.C generates the spatial maps for graphic output. If and when it is desired to superimpose a molecular structure on the output maps of the CoMFA methodology, the standard molecular modeling programs can be used to do so.

If commercial programs are not available, or if the user wishes to use programs other than Tripos Associates, Inc.'s, or if the user wishes to develop his own software environment in which to implement CoMFA, a functional description of all subroutines called by the four core CoMFA program segments is included following the source code listings. In actual use all the programs would be compiled and linked before execution. The PLS program can be converted into a stand alone program by converting appropriate comment lines at the beginning of the program back into source code.

As disclosed in the program listings, the CoMFA programs provide the user with a number of options. A complete list of options is given here:

In FIELD FIT:

1) Calculations may be done either in "interactive" mode—progress monitored on terminal or "batch"—separately, with notification of the user when complete.

2) Weighting of lattice points may be either: evenly; by QSAR coefficient; or by user-specified weights.

3) The steric and electrostatic components may either be handled independently or summed together.

4) Overall translations/rotations may be included or excluded.

5) Torsional rotations may be included (if so, user to specify which ones) or excluded.

6) How far should the molecule be moved in a trial move (initially—this value changes as Simplex minimization proceeds)?

7) Convergence criterion—how small must the geometric change in successive steps be before field fit is considered done?

8) Maximum number of steps before field fit quits, regardless of whether convergence has occurred.

9) The template ("target") field may be from a single molecule (conformer) or from several molecules (conformers) averaged together.

10) If in interactive mode (1 above), should the intermediate results be displayed after each 10 steps?

11) If in interactive mode and displaying intermediate results, should the user be asked whether to continue after each display?

12) Is this a regular field fit or else a "docking" field fit (where the objective is to maximize difference by field-fitting to complement of template field)?

13) What should be done to save the result of the field fit? The options are: nothing, write to an external file, replace the molecule in the database.

In EVAL.C:

1) The type of alignment to be performed on the molecule conformers. The options are: none, FIT, ORIENT, field fit.

2) Should the results of alignment be stored back into the database?

3) Should energy be "smoothed" (in which case the QSAR table value at a lattice point will be the average of the actual value and nine other values spaced evenly around that point)?

4) Element/hybridization state of the probe atom (controls its steric or van der Waals properties).

5) Charge of the probe atom (controls its electrostatic effect).

6) Method of estimating van der Waals parameters (standard SYBYL method or calculated by Scott/Scheraga—reference to Scott/Scheraga is in the code itself).

7) Repulsive van der Waals exponent value (usually 12).

8) Electrostatic exponent (usually 2, equivalent to a 1/r dielectric).

9) Maximum steric value to be recorded in the 3D-QSAR table (usually 30 kc/m).

10) Highest energy conformation to consider when representing a molecule as the average of conformations (excessively high energy conformers make vanishingly small contributions to the overall shape).

11) Should a 3D-QSAR table column be excluded if ANY compound in the QSAR table contributes a maximum steric value?

12) Should identities of excluded 3D-QSAR columns (which occur whenever there is no difference in value along a column in the table, because all compounds have a maximum steric value at that lattice point) be listed to terminal?

In PLS.FOR:
1) Is cross-validation to be done? If so, the number of cross-validation groups.
2) Is "bootstrapping" to be done? If so, the number of bootstrapping trials.
3) The number of components to extract.
4) Should data in individual columns be autoscaled (scaled so that the mean of values is 0.0 and the standard deviation is 0.0)? (This particular procedure is not recommended with CoMFA but is included as a general procedure available for use with PLS.)
5) Is there any relative weighting of columns? (When including other properties such as log P, it is necessary to give them extra weight in order to compete with the large number of field descriptor columns.)
6) Convergence criteria, specifically, epsilon, number of iterations, to be used within PLS itself. (A warning message printed if a round of PLS is ended by the number of iterations being exceeded rather than by a difference less than epsilon being obtained.)

In MAP.C:
1) What is the source of the 3-D data to plot, contour, or list? The options are (1) standard deviation of column times QSAR coefficient (2) standard deviation of column only (3) QSAR coefficient only (4) column value for an individual compound (5) column value for an individual compound times QSAR coefficient (6) external file.
2) Which aspect of 3-D data to plot or contour? The choices are steric, electrostatic, or both steric and electrostatic in separate display areas.

While the preceding written description of CoMFA is provided as an aid in understanding CoMFA, it should be understood that the source code listing constitutes a complete disclosure of CoMFA.

APPENDIX

/* Q3DEF.C */

```
/* Q3DEF.C provides DATA DESCRIPTION specific FOR CoMFA 3D-
QSAR METHODOLOGY. Its declarations are to be included in all
source files generating executable code. */ define KT 0.58

/* DATA STRUCTURES.

Note that, because a data type must be defined before it can
be used, the main CoMFA record structure is at the end, not
the beginning, of this file. */

/* The FOLLOWING "to_use" allows for new types of data needs
to be met in a fashion consistent with currently stored data,
in file I/O. In each of the data structures below, the *data
variable points to a record block whose first elements MUST
itself be a touse_rec,
as follows:

struct data_rec {
      struct touse_rec nxtrec;
      ..
      your actual data
      ..
      };
*/ struct touse_rec {
   char *data;
   int nbytes;
   };

struct q3lattice {         /* weights for each lattice point */
    struct touse_rec touse;   /* reserved for future use */
    int npoints;              /* number of points in *weights */
    double *weights;          /* weight for each lattice point,
sometimes used for field fit */
    };
```

```
struct q3region {     /* describes the rectangular region, or
lattice, to be used for energy sampling */
    double lo_coords [3],   /* Angstrom coordinates of starting
point */
         step_size [3];     /* spacing between lattice points,
in x, y, z; OR if nsteps all 1, and step_size[0] = 0.0,
step_size [1] (int) is probe atom type for this (one-point)
region, step_size [2] is charge */
    int nsteps [3];         /* number of steps along x, y, z */
    int inuse;              /* TRUE if following data item in
use */
    struct touse_rec touse; /* added later, points to a
q3lattice record with weights of points, sometimes used for
field fit */
    };

struct q3point {     /* describes a point in space that a
designated atom in each molecule should fit to, when the
alignment rule is least squares FIT, by rotation &
translation */
    double coords[3],       /* the point coordinates */
         weight;            /* the relative weight of this point
in the FIT */
    int atype;              /* type of atom to be fit to
(optionally used for checking correctness of input data) */
    int inuse;              /* TRUE if following data item in
use */
    struct touse_rec touse; /* reserved for future use */
    };

struct q3atom {     /* within a molecule description, describes
the atom in the molecule to be fit to a q3point description,
when the alignment rule is least squares FIT, by rotation &
translation */
    int id, atype;          /* identifier, type of the atom to
fit */
    int fit_to;             /* identifier of q3point record this
atom fits to */
    struct touse_rec touse; /* reserved for future use */
    };

struct q3align {    /* element of overall molecule description
that describes the atoms to be used in least squares FITting,
when FIT is the alignment procedure */
    int natoms;             /* total number of atoms in molecule
*/
    int natfit, atdim;      /* atoms to fit, number
present/allocated */
    struct q3atom *atm_ptr; /* points to atoms */
    int inuse;              /* TRUE if following data item in
use */
    struct touse_rec touse; /* point to fieldfit record */
    };

struct q3conf {     /* identifies a particular conformer of a
molecule */
    int id,                 /* identifier of conformer within a
SYBYL data base */
         mirror,            /* identifier of mirror image
conformer if not symmetric */
         savemap,           /* true if field map to be saved */
         encoords;          /* number of coords in saved field
```

```
map */
    char *m_name,              /* name (for checking input data) */
         *angles;              /* name of angle file (if any) to
scan */
    double energy,             /* energy of this conformation (for
Boltzman weighting) */
           weight,             /* user-supplied conformer weight */
           *emap;              /* energy values for field map */
    int different;             /* if TRUE this conformer's
connectivity is different from parent molecule (as tautomer
or protomer) */
    struct q3align q3align_rec;   /* used only if "different" is
true */
    int inuse;                 /* TRUE if following data item in
use */
    struct touse_rec touse;    /* reserved for future use */
    };

struct q3mol {          /* identifies a molecule */
    char *dbname;              /* complete filename of the data
base */
    int nconfs, confdim;       /* number of conformers to average,
actually & space allocated */
    int key1;                  /* identfier of default conformation
*/
    struct q3conf *cnf_ptr;    /* points to conformers - at least
one conformer must be present */
    double weight,             /* weight of the molecule */
           low_energy;         /* lowest energy of any conformer */
    struct q3align q3align_rec;   /* molecule alignment data */
    int bio_row;               /* identifier of table row
containing biodata */
    int chem_row;              /* same, for auxiliary physiochem
data */
    int inuse;                 /* TRUE if following data item in
use */
    struct touse_rec touse;    /* reserved for future use */
    };

struct q3dab {          /* describes a column in a table */
    int colid;                 /* identifier of column of the datum
*/
    char *col_name;            /* used to check input data */
    int inuse;                 /* TRUE if following data item in
use */
    struct touse_rec touse;    /* reserved for future use */
    };

struct q3plan {         /* basic description of a CoMFA study */
    int *t_d;                  /* points to a name, time, date
"stamp" */
    char *bio_data,            /* identifies table with bio data */
         *chem_data,           /* identifies table, chem data */
         *result_tbl;          /* name for any command files */
    int version,               /* TRUE if energy smoothing to be
done */
        orient,                /* =1 if alignment is ORIENT, =0 if
FIT, =2 if no ORIENT or FIT, =3 if FIELDFIT */
        valid,                 /* true if user input validated
since last edit */
        replace,               /* true if aligned molecules to
```

```
replace existing molecules in data base*/
        emaps,              /* true if any field maps present */
        ignore_atype,       /* absolute value is repulsive
exponent in VDW energy; if negative, distance-dependent
dielectric is omitted */
        ffield,             /* force field type code */
        nycols,             /* number of dependent vars (input
to PLS) */
        probe_type;         /* atom type of probe atom */
    double probe_charge,    /* charge on probe atom */
        hiOKenergy,         /* absolute value is highest energy
rotamer/ conformer may have; if negative, electrostatic also
is checked */
        too_big;            /* steric repulsion energy cutoff */
    int nregions, regdim;   /* number of regions, actual &
allocated */
    struct q3region *reg_ptr; /* points to region descriptions */
    int npoints, ptdim;     /* number of FIT atoms, actual &
allocatd */
    struct q3point *pt_ptr; /* points to FIT point descriptions
*/
    int nmols, moldim;      /* number of mols, actual &
allocated */
    struct q3mol *mol_ptr;  /* points to molecule descriptions
*/
    int nbios, biodim;      /* biological data for mol, actual &
allocated */
    struct q3dab *bio_ptr;  /* points to biodata descriptors */
    int nchems, chemdim;    /* chemical data for mol, actual &
allocated */
    struct q3dab *chem_ptr; /* points to chemdata descriptors */
    int inuse;              /* TRUE if following data item in
use */
    struct touse_rec touse; /* reserved for future use */
    };

/* GLOBAL DATA declaration */ extern struct q3plan *Q3D;    /* pointer to the user input -
space for actual data to be allocated as needed */ extern short COMPONENT, M1, M2, M3;
    extern int BIODAB, CHEMDAB;   /* identifier of bio, chem
tables */
    extern char lastSYB [D_MAX_STLG]; /* name of molecule data
base */
```

/* DABDEF.C */

```
/* DABDEF.C contains global data structures for the Tripos
Associates, Inc., general software for managing tables of
numbers, such as the QSAR, biological, and chemical data in
CoMFA. Functionally equivalent software includes RS/1 from
BBN Software, Cambridge, MA.
    Because the compiler must have each data type defined
before it can be used in another definition, the most
important elements of these data structures are at the end of
this listing.
    A number of data items included here are not used by any
of the CoMFA operations; these are indicated by comments
which have not been bolded and italicized. */
```

```
/* CONSTANTS */ define void            int
define D_MAX_TAB       16
#define TRUE            1
#define FALSE           0
#define MORE            0
#define QUIT            1
#define LOG1TRUE        '\1'    /* used in passing logical *1 to
FORTRAN */
#define LOG1FALSE       '\0'
#define D_MAX_STLG      133
#define D_CNEW          20
#define D_RNEW          100
#define D_ANEW          10
#define D_NANATYPES     14
#define N_COLORS        8       /* # of colors supported by
hardware */
#define WINDOW          10.0    /* display space +/- WINDOW */

/* STRUCTURES related to COLUMNS and ROWS */ struct err_bars
{
    double hi_bar,          /* highest value */
           lo_bar;          /* lowest value */
};

struct col_header       /* describes a column in a table */
{
    char *name_ptr;                 /* points to its name (if any) */
    struct err_bars *err_ptr;       /* points to an nrow - long array of
errbars, if any */
    int data_type,                  /* type of column (0 = "double", 1
= discrete variable which codes to text input or output */
        err_type,                   /* type of error */
        val_chged,                  /* value in column been updated? */
        active,                     /* column active (use in
calculations)? */
        nactv_rows,                 /* number of active rows */
        num_width,                  /* width of number (or text) field
on output */
        frc_width;                  /* if data_type = 0, width of
floating portion; if data_type = 1, number of different text
labels */
    char *misc                      /* if data_type = 1, points to head
of array of pointers to text label strings */
        ;
/* following are various univariate statistics for column
values */
    double hi_val,          /* highest value in column */
           lo_val,          /* lowest value in column */
           hi_quant,        /* high quantile */
           lo_quant,        /* low quantile */
           mad,             /* MAD */
           mean,            /* mean of column values */
           median,          /* median of column values */
           variance,        /* variance of column */
           std_dev,         /* standard deviation of column values */
```

```
            hi_err,           /* + uncertainty, if all rows same */
            lo_err            /* - uncertainty .. */
            ;
};

struct row_header            /* describes a row of table */
{  char *name_ptr;
   int val_chged,             /* has row value been changed? */
       active,                /* is row active (used in
calculations)? */
       how_created;           /* unused */
};

/* STRUCTURES- related to ANALYSES, which are the results of
calculations on a table */ struct ana_header
{
  char *title;     /* user title for analysis */
  int nanal,       /* 1 - number of results in the block */
      weights,     /* 2 - type of row weighting of data */
      wtcol,       /* 3 - contains id of column used to
weight */
      missing,     /* 4 - type of treatment of missing data
*/
      msgana,      /* 5 - identifier of analysis used to
estimate missing data */
      *rows_in,    /* 6 - points to bitset representation of
columns actually used in analysis; length is ncols*/
      *cols_in,    /* 7 - same as rows_in for rows; length
is nrows - YES - the names are backwards */
      type,        /* 8 - type of analysis */
      impossible,  /* 9 - is analysis still performable */
      valid,       /* 10 - is analysis currently valid */
      results,     /* 11 - points to result block */
      nrows,       /* 12 - number of rows = 1 in rows_in */
      ncols,       /* 13 -number of cols = 1 in cols_in */
      getrow,      /* 14 - rows were deleted, so should be
same on redo */
      getcol,      /* 15 - columns were deleted, should be
same on redo */
      sorted;      /* 16 - has sort made this analysis no
longer valid */
};

struct tbl_header /* STRUCTURE of table HEADER BLOCK itself */
{
  int *stamp,         /* 1 - ptr to validation STAMP info */
      version,        /* 2 - version of table */
      file_type,      /* 3 - type of data file currently associated */
      rows_named,     /* 4 - rows named? */
      cols_named,     /* 5 - cols named? */
      row_name_width, /* 6 - number of characters in longest
row name */
      read_err,       /* 7 - true if these data are corrupt */
      data_chged      /* 8 - have any data been changed? */
      ;
  long ncols,         /* 9 - number of column in use */
       nrows,         /* 10 - number of rows in use */
```

```
        nanas,          /* 11 - number of analyses performed */
        coldim,         /* 12 - number of columns allocated */
        rowdim,         /* 13 - number of rows allocated */
        anadim;         /* 14 - number of analyses allocated */
struct col_header *colhead;
        /* 15 - points to the column header array */
struct row_header *rowhead;
        /* 16 - points to the row header array */
double *data;
        /* 17 - points to the ACTUAL data array itself */
struct ana_header *anahead;
        /* 18 - points to analysis header block array */
long misc[11];          /* allocated for future use */
};

/* ACTUAL DATA DECLARATIONS */
/*   array of pointers to tables (all actual data in virtual
memory */ extern struct tbl_header   *dab [D_MAX_TAB];

/* MISCELLANEOUS GLOBAL VARIABLES - few if any needed for
CoMFA */
   extern int pix,      /* points to picture data */
       d_ntabs, /* id of HIGHEST table created (may not be the last) */
       d_page_width[4],   /* width of output page  (3 devices, 0th is
ignored) */
       d_page_length[4],
       regr_format,
       resid_do,        /* residuals to be computed? (ync) */
       resid_ord_by_val,  /* residuals ordered by val? */
       resid_max_num,   /* max num of resids to sho - if 0 all done */
       resid_do_empty,  /* compute resids for empty? */
       resid_sho_vari,  /* show % variance with output? */
       resid_unused,    /* treatment of rows not used in derivation */
       resid_plot,      /* residuals to be plotted (anc) */
       resid_add,       /* residuals to be made into new column */
       unit,            /* code for ascii output (1 = terminal,
                     2 = printer, 3 = disk, 4,0 = none) */
       lines,           /* number of lines sent to current output page
*/
       user_names_f,    /* whether user names background files (anc) */
       term_type,  /* code for terminal type (from TERM_TYPE token */
       pick_state, /* is user picking or typing in ID#s? */
       inf_hilite,      /* whether hiliting should accompany inform */
       inf_inform, /* whether inform should accompany hiliting */
       inf_arr2tab,     /* whether array to table should be requested */
       sca_jitter, /* whether points should never have identical coords
*/
       color_ask,  /* whether color should be obtained for each element
*/
       color_range [N_COLORS],
       color_level [N_COLORS],
       color_default [N_COLORS],   /* user-definable runtime color tables
*/
       last_hilite,     /* last color used to hilite */
       inact_ana,  /* whether inactive rows/cols should be analyzed */
       sca_scale,  /* scaling option; 1=independent,2=previous,3=user */
```

```
    arr_drop_rc,        /* whether to drop unused rows and columns */
    text_sho,           /* whether to show text-coded values as such */
    eqn_max2sho,        /* maximum number of terms to show in first
output */
    tot_bkgs;           /* total number of backgrounds being displayed
*/ extern FILE *fp;      /* the ascii output file */ extern double D_MISSING;   /* value associated with EMPTY or MISSING
datum */ extern char msg[D_MAX_STLG];  /* passes message to output utilities */ define CALLOC_SIZE    1000    /* stuff for alloc/free check */ extern int calloc_num, callocd [CALLOC_SIZE];
```

/* EVAL.C */

```
/* The following is the main module that turns a database of
molecules, plus an associated table of biological data, plus
other user specified options, into a table ready for PLS
analysis.
    The computer language is C. There is a naming convention
for subroutines. If they start with "q3$", they are
explicitly associated with CoMFA. For example, a routine
beginning with "q3$_eva" can be found elsewhere in this
listing.
*/

/* general declarations */ if vax11c
module eval "V1.0"
endif include stdio
include "dab$source:dabdef.c"
# include "q3d$source:q3def.c"

/* the data structures in q3def.c are provided separately */ include "sys$runsource:vmsstrdef.h"

define MAXA    1500
define MRBDS     20 float *ptwts;    /* weights of points in fitting */

/* following declaration is only for conformer file */
short bincr[MRBDS], mbonds, angc[MRBDS], batom[MRBDS][4],
    /* C indices vs FORTRAN */ rbndnum[MRBDS], angoff[MRBDS], ok,
    nrots, engflg, flg13, flg14, nutb, snr, no = 0, snc, error;
float eng;
int nconf;
double fabs();

int q3$eval (q, tblout, nrout, nxout, nyout)
/* MAIN SUBROUTINE ========================================= */
```

/* CONVERTS PLAN INTO 3D-QSAR ARRAY, FOR PLS ANALYSIS */

```
struct q3plan *q;            /* the CoMFA user options (INPUT) -
see q3def.c for declaration */
int     *tblout,    /* identifier of QSAR table (OUTPUT) */
        *nrout,     /* number of rows in QSAR table (OUTPUT) */
        *nxout,     /* number of columns of independent variables
(OUTPUT) */
        *nyout;     /* number of columns of independent variables
(OUTPUT) */
{
    int nrow, nxcol, nycol, drophi, nx2use, nokcolprt, okcol,
        nlcol, nreg, ncoor, ncolreg, nmol, i, nconf, j, cdim, k;
    struct q3mol *m;
    struct q3conf *cf;
    extern char *UTL$STR_SAVE();
    extern VMS_String UTL$VMSSTR_CARVE();
    VMS_String *vdb;
    double boltsum, *work, *pls, loenergy, *ptcoor, *q3$map_initc(),
        *q3$map_nxc(), dab$dut_g2df(), val, Q3Dtoobig;
    struct tbl_header *btptr, *ctptr;
    struct col_header *cptr;
    struct row_header *rptr;
    char *nvalid = ("Plan has been edited and not validated\n");
    short one = 1, nr, nc, zero = 0, tbl, fopen_flg = -1, neg1 = -1;
    char err, *UTL$STR_SAVE();
    int tblid, chwts;
    struct tbl_header *tptr;
    static char *mltype[] = ("ST","EL");

if (!dab$usr_ynans ("Exclude lattice points occupied by ANY
molecule",
        TRUE, FALSE, &drophi)) return (FALSE);
    if (!dab$usr_ynans ("List description of all excluded lattice
points",
        TRUE, FALSE, &nokcolprt)) return (FALSE);

dab$stmp_list (fp, q -> t_d);
    if (!q -> valid) {
        fprintf (fp, nvalid); fprintf (stderr, nvalid);
        ferr (); return (FALSE);
    } tptr = 0;
    tblid = 0;
    nycol = q -> nbios;
/* allocate array space - How many lattice points in ALL
regions? */
    nlcol = 0;
    for (nreg = 0; nreg < q -> nregions; nreg++) {
/* increment by x*y*z steps of each region */
        nlcol += q3$eva_npts (q -> reg_ptr + nreg);
    }
    fprintf (fp, "DATA ALLOCATION\n");
    fprintf (fp, "Total of %d lattice points among %d regions; => %d
columns",
        nlcol, q -> nregions, 2 * nlcol);
    nxcol = 2 * nlcol;    /* both electrostatic and steric */

/* also any physicochemical properties  such as logP*/
    if (q -> nchems) {
        fprintf (fp, " (& %d physical properties) ", q -> nchems);
```

```
    if (!dab$usr_getbint ("How many duplicate columns (at least 1)",
        1,10000, &chwts)) return (FALSE);
    }
    fprintf (fp, " %d molecules;\n", q -> nmols);

pls = 0; work = 0; ptwts = 0;
    cdim = (q -> nchems) * chwts + q -> nbios + nxcol;
    if (!dab$mat_spdbl (&work, cdim, "Working vector")) goto free;

/* get memory for the QSAR table to store field values, with
maximum number rows */
    tbl = (short) tblid; nr = (short) q -> nmols; nc = (short) cdim;
    if (!dab$ini_table (&tbl, &nr, &nc, &zero, &zero, &tbl)) goto free;
    tptr = dab [tblid];
    cdim = tptr -> coldim;
    pls = tptr -> data;
    tptr -> cols_named = TRUE; tptr -> rows_named = TRUE;
    tptr -> nrows = 0;          /* start with no cpds in table */

/* name the columns */
    nreg = 0;
      ptcoor = q3$map_initc (&nreg, &negl, 0, 0, 0);
      for (i = 0; ptcoor; i++, ptcoor = q3$map_nxc (&nreg, &negl, 0, 0,
0))

for (j = 0; j < 2; j++) {
            sprintf (msg, "%sx%.1fy%.1fz%.1f", mltype [j],
             ptcoor[0], ptcoor[1], ptcoor[2]);
            cptr = tptr -> colhead + q -> nchems * chwts
             + q -> nbios + i + j * nlcol;
            cptr -> num_width = 19;
            cptr -> frc_width = 5;
            if (!(cptr -> name_ptr = UTL$STR_SAVE(msg)) )
              {dab$dut_mem_err ("clab"); goto free;}
        } if (!Q3D -> orient) {
      if (!dab$mat_spint (&ptwts, MAXA, "Fit weights")) goto free;
      for (i = 0; i < MAXA; i++) ptwts [i] = 1.0;
      } fprintf (fp, "Allocation successful\n");
    nrow = 0; nycol = q -> nbios; nxcol = nxcol + q -> nchems * chwts;

/* open the bio- (& possibly chem- (logP) ) database(s) */
    if (!q3$eva_dabio (q -> bio_data, "bio", BIODAB, q -> bio_ptr,
        q -> nbios, tptr, 0)) goto free;
    btptr = dab [BIODAB];
    tptr -> row_name_width = btptr -> row_name_width;

if (q -> nchems) {
      if (!q3$eva_dabio (q -> chem_data, "chem", CHEMDAB, q -> chem_ptr,
          q -> nchems, tptr, q -> nbios)) goto free;
      ctptr = dab [CHEMDAB];
      }
/* open VDW parameter file */
    if (q -> ffield == 2) {
      par$open_minvdw (&zero, &fopen_flg);
      if (fopen_flg) {
        dab$dut_sho_err ("Could not open SYBYL VDW parameter file");
        goto free;
        }
      }
```

```
/* if alignment rule is FIT, set up atoms to be fit TO in
component area */
    if (!q -> orient) {
        zap (&COMPONENT, &one);      /* SYBYL*/
        edit (&COMPONENT);           /* SYBYL */
        for (i = 0; i < q -> npoints; i++)

q3$eva_store_atom (COMPONENT, i, q -> pt_ptr + i);
    }

/* start loading 3D-QSAR data array; one row per molecule
entry */
    for (nmol = 0, nrow = 0; nmol < q -> nmols; nmol++) {
        m = q -> mol_ptr + nmol;
        fprintf (fp, "\nMolecule # %d; ", nmol+1);
        if (! m -> dbname) {
            fprintf (fp, "- no dbase name\n");
            goto nxmol;
            }
        else fprintf (fp, " data base '%s'\n", m -> dbname);
        if (!m -> weight) fprintf (fp, " .. Zero Weight");
        if (!m -> weight || !m -> inuse) {
            fprintf (fp, " - skipped\n");
            goto nxmol;}

/* check the biological (and chemical?) data for this row
*/
        if (!q3$eva_dabrow (BIODAB, m -> bio_row, "bio", m -> cnf_ptr ->
m_name))
            goto nxmol;
        if (q -> nchems && !q3$eva_dabrow (CHEMDAB, m -> chem_row, "chem",
            m -> cnf_ptr -> m_name)) goto nxmol;

/* get the bio- (and chem) data */
        rptr = tptr -> rowhead +      nrow;
        if (rptr -> name_ptr) UTL_MEM_FREE (rptr -> name_ptr);
        if (!q3$eva_gdata (btptr, m -> bio_row, q -> bio_ptr, pls,
            cdim, nrow, q -> nbios, "bio", m -> weight, 0, rptr, 1)) goto
nxmol;
        if (q -> nchems)
            if (!q3$eva_gdata (ctptr, m -> bio_row, q -> chem_ptr, pls,
                cdim, nrow, q -> nchems, "chem", m -> weight, nycol, 0, chwts))
                goto nxmol;

/* open the molecule data base for this row if not already
open - */
        if (!q3$mol_dbaseopen (m, FALSE)) {
            fwarn();
            fprintf (fp, " Data base %s not opened", m -> dbname);
            goto nxmol;
            }

/* calculate Boltzman sum over ALL conformers for molecule -
also checks molecule data; failure => no forms for the
molecule were readable
*/
        if (!q3$eva_boltstates (m, &boltsum, &loenergy)) {
            fwarn(); fprintf (fp, " Molecule %d SKIPPED\n", nmol+1);
            goto nxmol;
            }
```

```c
/* cycle thru conformers */
    for (i = 0; i < 2 * nlcol; i++) work [i] = 0.0;
    for (nconf = 0; nconf < m -> nconfs; nconf++) {
        cf = m -> cnf_ptr + nconf;
        fprintf (fp," Conformer %d\n", nconf+1);

/* read conformer from molecule data base to ml work area */
        /* SYBYL */ dbget0 (&M1, &(cf -> id), &err);
        if ((err != LOG1FALSE) || !q3$eva_chkconf (m, cf)) {
            fwarn(); fprintf (fp, "Skipping conformer %d\n", nconf +
1);
        }
/* THIS IS THE MAJOR subroutine; accumulates into a temporary
array the field values to go into a row of the QSAR table
*/
        else if (!q3$eva_addconfs (q, m, cf, work, nlcol, boltsum,
            loenergy, nconf, &M1)) {ferr(); goto nxmol;}
        }
/* copy temporary array (sum of effects of all conformers) to
PLS row */
    for (i = 0, j = q -> nchems * chwts + q -> nbios; i < 2 * nlcol;
i++,
            j++)
        dab$dut_p2df (pls, cdim, nrow, j, work [i] );
    nrow++;
    (tptr -> nrows)++;
/* jumps here if bad data means this molecule must be skipped
*/
nxmol: ;
    }

/* falls thru to here when 3D-QSAR table all ready */

/* turn off columns with zero variance - PLS can't use them,
&, if desired, columns located inside any molecule +
spatially corresponsing electrostatic columns*/ nx2use = nlcol;
if (tptr -> nrows == 1)
    dab$dut_shomsg ("only one compound - skipping variance tests");
else {
/* cycle through steric field only */
    for (j = 0, i = q -> nchems + q -> nbios, Q3Dtoobig=fabs(Q3D-
>too_big) ;
            j < nlcol; i++, j++) {
        dab$fil_setrange (tblid, i);
        cptr = tptr -> colhead + i;
        if (!(okcol = (cptr -> std_dev != 0.0 && cptr -> std_dev !=
D_MISSING))
            && nokcolprt)
        fprintf (fp, "All energies same in '%s' (column # %d); not
used\n",
            cptr -> name_ptr, i + 1);
        if (okcol && drophi)
        for (nrow = 0; nrow < tptr -> nrows && okcol; nrow++) {
            okcol = dab$dut_g2df (tptr -> data, tptr -> coldim, nrow, i)
                != Q3Dtoobig;
            if (!okcol && nokcolprt) fprintf
(fp, "Point at '%s' inside molecule # %d; column %d not used\n",
                cptr -> name_ptr, nrow + 1, i + 1);
        }
        if (!okcol) {
```

```
        cptr -> active = FALSE;
        q3$eval_makemissing(tptr,i);

/* but then turn off electrostatics */
        cptr = tptr -> colhead + (i + nlcol);
        cptr -> active = FALSE;
        q3$eval_makemissing(tptr,i + nlcol);
        nx2use--;
        }
    }

/* set "missing" electrostatic values to mean of column */
    for (j = 0, i = q -> nchems + q -> nbios + nlcol; j < nlcol; i++,
j++) {
        cptr = tptr -> colhead + i;
        if (cptr -> active) {
        dab$fil_setrange (tblid, i);
        for (k = 0; k < tptr -> nrows; k++) {
                val = dab$dut_g2df (tptr -> data, tptr -> coldim, k, i);
                if (val == D_MISSING) dab$dut_p2df (tptr -> data,
                     tptr -> coldim, k, i, cptr -> mean);
            }
        }
      }
    } fprintf (fp, "%d lattice points can be used\n", 2 * nx2use);
/* procedure succeeded if got here */
        UTL_MEM_FREE (work);
        if (ptwts) UTL_MEM_FREE (ptwts);
    *tblout = tblid;
    *nrout = nrow;
    if (!fopen_flg) par$close_minvdw();
    *nxout = nxcol;
    *nyout = nycol;
    dab$dut_shomsg (" ");
        return (TRUE);

/* procedure failed if here; free memory and return */
free:
        if (tptr) dab$ini_free_all (tblid);
        if (work) UTL_MEM_FREE (work);
        if (ptwts) UTL_MEM_FREE (ptwts);
    if (!fopen_flg) par$close_minvdw();
    dab$dut_shomsg (" ");
        return (FALSE);
} define VALID_CHARGES   2 int q3$eva_addconfs (q, m, cf, work, nlcol, boltsum, loenergy, cfid,
     molarea)
/* SUBROUTINE =================================================== */
/* (Note that a rotamer is a special type of conformer
resulting from rotation about a bond that is not constrained
by being part of a ring.)
A) For each rotamer (if a SEARCH output is referenced there
will be a number of rotational states), this routine:
    1) orients the rotamer as prescribed
```

2) computes its steric and electrostatic effects at the lattice points described and, weighted by energy, accumulates these into work.
B) If "emap" is TRUE, makes copy of effects of 1st rotamer for graphing by user, attaches to conformer & sets appropriate flags;
C) Saves the oriented state back into the SYBYL data base if appropriate
*/

```
struct q3plan *q;
struct q3mol *m;
struct q3conf *cf;
double *work, boltsum, loenergy;
int nlcol, cfid;
short *molarea;
{
  int nrots, nrot, i, okconf, atnum, nat, nl, nreg,
      anow, distok, natm, j, fitat, success = TRUE;
  short chndx, stat, premeth, ishort, lun = 0, natsht;
  double *coords, *charges, *VDWa, *VDWb, dist, dis6, dis12, steric,
elect,
      sster, select, *ptcoor, diff, nowe, nowt, q3$eva_genergy();
  struct q3align *qal;
  extern float echg();
  extern double exp(), sqrt(), dab$dut_g2df(),
      *q3$map_initcoords(), *q3$map_nxcoords();

coords = 0; charges = 0; VDWa = 0; VDWb = 0;
  if (!boltsum) boltsum = 1.0;

nrots = q3$eva_nrots (m, cfid, &lun);  /* returns number of
conformers - always at least 1, opens SEARCH file if
requested by user */ fprintf (fp, "%d Rotamers: ", nrots);
/* cycle through all conformers */
  for (nrot = 0; nrot < nrots; nrot++) {
    okconf = TRUE;

/* STAGE 1: if new conformer, prepare atomic data */
    if (!nrot) {         /* specifically coords, charges, and VDW
data */
        success = FALSE;
        qal = cf -> different ? &(cf -> q3align_rec) : &(m ->
q3align_rec);
        q3f$syb_gnatoms (molarea, &natm);
        if (qal -> natoms != natm) {
            ferr(); fprintf (fp,
"# atoms inconsistent (plan has %d and conformer has %d);", qal ->
natoms,
natm); fskip(); goto free;
        }
        if (!dab$mat_spdbl (&coords, 3 * qal -> natoms, "Coords")) goto
free;
        if (!dab$mat_spdbl (&charges, qal -> natoms, "Charges")) goto
free;
        if (!dab$mat_spdbl (&VDWa, qal -> natoms, "VDWs")) goto free;
```

```
    if (!dab$mat_spdbl (&VDWb, qal -> natoms, "VDWb")) goto free;

fndchg (&chndx, &stat, &premeth, molarea);
    if (stat != VALID_CHARGES) {
        ferr(); fprintf (fp,
"Charges invalid or missing (code = %d);", stat); fskip(); goto free;
    }
    for (i = 0, ishort = 1; i < qal -> natoms; i++, ishort++) {
      q3f$echarge (&chndx, &ishort, molarea, &(q -> probe_charge),
        &(charges [i]));
        j = i + 1;
      q3f$syb_atype (&j, molarea, &anow);
      q3$eva_VDW_tab (anow, q -> probe_type, &(VDWa [i]), &(VDWb
[i]),
        q -> ffield);
    }
    fprintf (fp, " .. atm params OK");
    }

/* STAGE 1.5. If multiple rotamers, obtain & (if conf OK)
apply
torsional rotation to existing structure in M1 */
    if (nrots > 1) {
        okconf = q3$eva_nxconf (cf -> angle_select);
        if (okconf) okconf = !engflg || (eng - loenergy <= Q3D ->
hiOKenergy);
        if (okconf) q3$eva_dochange (molarea);
    }

/* STAGE 2: ORIENT or FIT the rotamer in M1 */
    if (okconf) { if (!q3$eva_align_cf (molarea, !nrot, m, cf, qal,
/* save orientation if appropriate, requested, and 1st
rotamer */
            ((q -> replace || cf -> savemap) && (q -> orient < 2)) ))
                goto free;

/* STAGE 3 - COMPUTE STERIC & ELECTROSTATIC EFFECTS.
APPROPRIATELY (BOLTZMAN?) WEIGHTED, AND ACCUMULATE IN WORK */

/* cycle through all lattice points */ if (nrots == 1) {
            if (cf -> energy == D_MISSING) nowt = (cf -> weight) /
boltsum;
                else nowt = (cf -> weight) *
                    (exp ((loenergy - cf -> energy)/KT)) / boltsum;
        }
        else if (!engflg) nowt = (cf -> weight) / ((double) nrots);
        else nowt = (cf -> weight) * (exp ((loenergy - eng)/KT)) /
boltsum;

natsht = (short) natm;
        q3f$syb_getcoords (coords, molarea, &natsht);
        q3$eva_enrgy (coords, nlcol, natm, VDWb, VDWa, charges, work,
nowt,
```

```
                molarea);

} /* end of a rotamer energy calculation */ fprintf (fp, " %d", nrot+1);
    if (!((nrot+1) % 20))fprintf (fp, "\n ");

} /* end of all rotamers */
    success = TRUE;
        if (cf -> savemap) {
            if (cf -> encoords) {
                UTL_MEM_FREE (cf -> emap); cf -> encoords = 0;}
            if (!dab$mat_spdbl (&(cf -> emap), 2 * nlcol, "EMap")) goto
free
;
            cf -> encoords = 2 * nlcol;
            for (i = 0; i < 2 * nlcol; i++) cf -> emap [i] = work [i];
            q -> emaps = TRUE;
            } free:
   if (coords) UTL_MEM_FREE (coords);
   if (charges) UTL_MEM_FREE (charges);
   if (VDWa) UTL_MEM_FREE (VDWa);
   if (VDWb) UTL_MEM_FREE (VDWb);
   if (lun) fdab$close (&lun);
   return (success);
} define Q2KC 332.0
define MIN_SQ_DISTANCE 1.0e-10
        /* if any lattice point within .00001 Angstroms of atom,
    they overlap, drop the point*/ void q3$eva_enrgy (coords, nlcol, natm, VDWb, VDWa, charges, work, nowt,
        molarea)
/* SUBROUTINE ============================================ */
/* This is a central subroutine, both for building the CoMFA
QSAR table and also for field-fit. This routine calculates
the actual values in a row of the QSAR table, or that field-
fit uses in trying different alignments for the field-fitted
molecule. Unfortunately the logic is complicated by lots of
options. Specifically, this routine ADDS to nlcol*2 long
array "work", weighted by nowt, the interaction energy of
molecule, described on input by natm long array coords, VDWb,
VDWa, charges (if nlcol is 0, steric and electrostatic added
together !)
    Other options:
1) VDW repulsive exponent
2) probe atom type/charge may be variable by region
3) can "smooth" energy calcn at single point per lattice
intersection with average of 9 surrounding points, at 1/3
lattice separation
*/
```

```
double *coords,            /* coords for each ligand atom */
       *VDWa, *VDWb, *charges, /* parameters for each ligand atom
*/
       *work,              /* (OUTPUT) where the answers go (or
are                            accumulated) */
       nowt;               /* the weight of this conformer */
int nlcol,                 /* number of lattice points */
    natm;                  /* number of atoms */
short *molarea;
{
    int nl, nat, nreg, lastnreg, distok, i, noff, noffsets = 1,
Q3Delmax,
        stexponent, distdepdiel;
    double *tpcoor, ptcoor[3], *q3$map_initc(), diff, dab$dut_g2df(),
dist,
        dis6, dis12, steric, elect, sster, select, *q3$map_nxc(),
        offsets [9][3], ss_ster, ss_elect, Q3Dtoobig, Q3D2big, nokf,
        fabs(), sqrt();

Q3Dtoobig = fabs(Q3D->too_big);
    Q3Delmax = (Q3D->too_big < 0.0);   /* negative if el.also
has a max */ stexponent = abs(Q3D -> ignore_atype);
    distdepdiel = Q3D->ignore_atype > 0;
 offsets[0][0] = offsets[0][1] = offsets[0][2] = 0.0 ;

nreg = lastnreg = 0;

tpcoor = q3$map_initc (&nreg, molarea, VDWb, VDWa, charges);
    if (Q3D -> version) q3$eva_smooth_offsets (offsets, nreg,
&noffsets);
    Q3D2big = noffsets * Q3Dtoobig;
/* for each lattice point ... */
    for (nl = 0; tpcoor;
        nl++, tpcoor = q3$map_nxc (&nreg, molarea, VDWb, VDWa,
charges)) {
        ss_ster = 0.0; ss_elect = 0.0; nokf = 0.0;
        if (Q3D -> version && nreg != lastnreg) {
            q3$eva_smooth_offsets (offsets, nreg, &noffsets);
            Q3D2big = noffsets * Q3Dtoobig; }
        lastnreg = nreg;
            distok = TRUE;
/* ... while, possibly, accumulating interactions in a
smoothing way */
        for (noff = 0; distok && noff < noffsets; noff++) {
            for (i = 0; i < 3; i++) ptcoor[i] = tpcoor[i] + offsets
[noff][i];
/* sum steric and electrostatic interaction energy over all
atoms */
            for (nat = 0, sster = 0.0, select = 0.0;
                       (nat < natm) && distok; nat++) {
/* square of distance between lattice point & this atom */
                for (i = 0, dist = 0.0; i < 3; i++) {
                    diff = (dab$dut_g2df (coords, 3, nat, i) - ptcoor[i]);
                    dist += diff * diff;
                }
                distok = dist > MIN_SQ_DISTANCE;
```

```
              if (!distok) break;      /* lattice point too close,
skip atom! */
              dis6 = dist * dist * dist;
              switch (stexponent) {
case 6:                dis12 = dis6; break;
case 8:                dis12 = dis6 * dist; break;
case 10:       dis12 = dis6 * dist * dist; break;
case 12:       dis12 = dis6 * dis6; break;
case 14:       dis12 = dis6 * dis6 * dist; break;
default:       sprintf (msg, "Illegal repulsive exponent %d",
                  stexponent);
               dab$dut_sho_err (msg);
               return;
              }
      /* steric energy between point and atom */
              steric = VDWb [nat] / dis12 - VDWa [nat] / dis6;
              sster += steric;
      /* electrostatic energy - by default, use 1/r dielectric */
              if (!distdepdiel) dist = sqrt (dist);
                 elect = charges [nat] / dist;
                 select += elect;
                 } /* end of all atoms with a lattice point */ ss_ster += sster;
         if (ss_ster > Q3D2big) distok = FALSE; /* already too much
steric repulsion */
             ss_elect += select;
             nokf += 1.0;
         } /* end of smoothing offsets */

/* divide sum by noffsets; check range; zap if out of range;
do cleanup */
/* add weighted energy of conformer / probe atom interaction
to work */
      if (!distok) {
         ss_ster = Q3Dtoobig;
         nokf = 0.0;  }
           else if (noffsets != 1) ss_ster /= nokf; /* nokf is noffsets
as a double*/
         ss_ster *= nowt;
           work [nl] += ss_ster;

if (nokf==0.0 || work [nl + nlcol] == D_MISSING)
             work [nl + nlcol] =.D_MISSING;
            else {
            ss_elect *= Q2KC;
            if (noffsets != 1) ss_elect /= nokf;
            if (Q3Delmax) { /* Q3D->too_big assumed negative here!
*/
                if (ss_elect < Q3D->too_big)   ss_elect = Q3D-
>too_big;
                else if (ss_elect > Q3Dtoobig) ss_elect = Q3Dtoobig;
        }
            ss_elect *= nowt;
            work [nl + nlcol] += ss_elect;
            }
          }    /* end of all points in all regions */

}
```

```
q3$eva_smooth_offsets (f, nreg, noffsets)
/* SUBROUTINE =============================================== */
/* computes successive offsets when smoothing is in effect;
result is initial point plus offsets to generate 8 corners of
surrounding parallelipipid whose coordinates are initial
coords +/- 1/3 of corresponding step_size */
double f [9][3];
int nreg, *noffsets;
{
   struct q3region *r;
   double of2s [2] [3];
   int i, j;

r = Q3D -> reg_ptr + nreg;
   *noffsets = 9;

f[0][0]= f[0][1]= f[0][2]= 0.0 ;

if (r -> nsteps [0] == 1 && r -> nsteps [1] == 1 && r -> nsteps [2]
== 1
       && ! r -> step_size [0]) {
            *noffsets = 1;
            return;
            }
   for (i = 0; i < 3; i++) {
       of2s [0][i] = r -> step_size [i] / 3.0;
       of2s [1][i] = 0 - of2s[0][i] ;
       } f[1][0] = of2s[0][0];   f[1][1] = of2s[0][1]; f[1][2] = of2s[0][2]; /* +
+ + */
 f[2][0] = of2s[0][0];   f[2][1] = of2s[0][1]; f[2][2] = of2s[1][2]; /* +
+ - */
 f[3][0] = of2s[0][0];   f[3][1] = of2s[1][1]; f[3][2] = of2s[0][2]; /* +
- + */
 f[4][0] = of2s[0][0];   f[4][1] = of2s[1][1]; f[4][2] = of2s[1][2]; /* +
- - */
 f[5][0] = of2s[1][0];   f[5][1] = of2s[0][1]; f[5][2] = of2s[0][2]; /* -
+ + */
 f[6][0] = of2s[1][0];   f[6][1] = of2s[0][1]; f[6][2] = of2s[1][2]; /* -
+ - */
 f[7][0] = of2s[1][0];   f[7][1] = of2s[1][1]; f[7][2] = of2s[0][2]; /* -
- + */
 f[8][0] = of2s[1][0];   f[8][1] = of2s[1][1]; f[8][2] = of2s[1][2]; /* -
- - */
} int q3$eva_align_cf (molarea, chkatypes, m, cf, cal, saveit)
/* SUBROUTINE =============================================== */
/* aligns a conformer of a molecule as user requests */
short *molarea;
int chkatypes, saveit;
```

```
struct q3mol *m;
struct q3conf *cf;
struct q3align *qal;
{
    int i, fitat, *aprfit, atnum, j, success = FALSE;
    short shatm [3], *atmprs, nshtatm, szero = 0, sone = 1, ishort;
    char *UTL_MEM_CALLOC ();

aprfit = 0;
    atmprs = 0;
    switch (Q3D -> orient) {
case 2:     break;          /* no alignment done */
case 1:                     /* action is ORIENT */
        if (chkatypes && !q3$eva_chkatypes (Q3D, qal)) goto free;
                /* atoms present & OK ? */
        for (i = 0; i < 3; i++) shatm [i] = (short)
           q3$eva_getatid (m, i, &fitat);
        /* SYBYL */ orient (molarea, &(shatm [0]), &(shatm [1]),
&(shatm [2]));
        break;
case 0:                     /* action is FIT */
        if (chkatypes && !q3$eva_chkatypes (Q3D, qal)) goto free;
        if (!(atmprs = (short *) UTL_MEM_CALLOC
                    (MAXA*2, sizeof (short)) )) {
            dab$dut_mem_err ("Atom Pairs"); goto free;}
        if (!dab$mat_spbit (&aprfit, qal -> natoms, "Atom Pairs"))
            goto free;
        dab$bit_init (aprfit, qal -> natoms);
        for (i = 0; i < qal -> natfit; i++) {
            atnum = q3$eva_getatid (m, i, &fitat);
            atmprs [i] = (short) atnum;    /* M1 to be fit */
            dab$bit_on (aprfit, atnum);
            atmprs [MAXA+i] = (short) (fitat + 1);   /* C "to be fit"
*/
        }
        j = qal -> natfit;
        for (i = 1; i <= qal -> natoms; i++)
        if (!dab$bit_isiton (aprfit, i)) {
                atmprs [j] = i;            /* other atoms in M1 */
            j++;
        }
        nshtatm = (short) qal -> natfit;

bestfit (molarea, &nshtatm, atmprs, &szero, &sone,
            &szero, ptwts);
/* case 3 would be Field Fit */
        break;
    }
    if (saveit && chkatypes) {
            ishort = (short) cf -> id;
            /* SYBYL */ dbput (molarea, &ishort);
        fprintf (fp, " .. SYBYL db #%d  replaced\n", cf->id);
    }
    success = TRUE;
free:
    if (atmprs) UTL_MEM_FREE (atmprs);
    if (aprfit) UTL_MEM_FREE (aprfit);
    return (success);
```

}

```
static int q3$eva_boltstates (m, boltsum, loenergy)
/* SUBROUTINE ============================================== */
/* computes Boltzman sum; returns fail if no states were
readable */
struct q3mol *m;
double *boltsum,      /* output: Boltzman sum */
        *loenergy;    /* output: lowest energy found for any
conformer */
{
    int oknow, okpass, nc, nr, havel, oklo;
    double nowe;
    static int nrot;
    struct q3conf *cf;
    extern double q3$eva_genergy(), exp();
    short lun = 0;

*loenergy = m -> low_energy;
    havel = FALSE;

if (m -> nconfs == 1 && !m -> cnf_ptr -> angles) {
                /* only 1 rotamer of 1 conf */
      *boltsum = 1.0;
      *loenergy = 0.0;
      havel = TRUE;
      }
     else do {      /* start of repeat until loenergy is stable */
       *boltsum = 0.0;
       for (nc = 0, oklo = TRUE; (nc < m -> nconfs) && oklo; nc++) {
                                /* loop over all conformers .. */
          cf = m -> cnf_ptr + nc;
         nrot = q3$eva_nrots (m, nc, &lun);
         if (cf -> angle_select) {
             nrot = nrot / cf -> angle_select;
             if (nrot < 2) {
                 dab$dut_shomsg (
"Only one rotamer selected - calculations will be done for parent
conformation")
;
                 nrot = 1;
                 }
             }
        if (nrot == 1) {
             havel= TRUE;
             if (cf -> energy == D_MISSING) *boltsum += cf -> weight;
             else
               {eng = cf->energy;
                *boltsum += (cf -> weight) * exp ((*loenergy - eng)/KT); }
             }
      else for (nr = 0; (nr < nrot) && oklo; nr++) {
             havel = TRUE;
             if (nrot == 1) eng = cf -> energy;
             if (!q3$eva_nxconf (cf -> angle_select)) return (FALSE);
                oknow = (eng >= *loenergy) && (*loenergy != D_MISSING);
                if (!oknow) {
```

```
            if (oklo) {
                fwarn (); fprintf (fp,
" Energy of rotamer %d of %d of conformer %d = %g, lower than %g\n",
nr+1, nrot,
nc+1, eng, *loenergy);
                fprintf (fp, "Restarting Boltzman sum\n");
                oklo = FALSE;
            }
                m -> low_energy = *loenergy = eng;
                }
            else if (eng - *loenergy > Q3D -> hiOKenergy) {
                fwarn (); fprintf (fp,
"Rotamer %d of %d ignored; energy too high (difference = %f)\n",
nr+1, nrot, eng - *loenergy);
                }
            else *boltsum += (cf -> weight) * exp ((*loenergy -
eng)/KT);
            }
        }
        if (lun) fdab$close (&lun);
        } }while (!oklo);
    return (havel);
} static int q3$eva_nrots (m, nc, lun)
/* SUBROUTINE ================================================ */
/* returns number of rotamers for conformer (depends on
whether there is a search file). Opens search file if present
*/
struct q3mol *m;
int nc;
short *lun;
{
    struct q3conf *cf;
    VMS_String molnam, vmsfname, UTL$VMSSTR_CARVE ();

if (nc > m -> nconfs) {
        ferr (); fprintf (fp, "No %d conformer\n", nc+1);
        return (FALSE);    /* i.e., 0 states */
        }
    cf = m -> cnf_ptr + nc;
    if (! cf -> angles) return (1);    /* only the parent */
    else {
        molnam = UTL$VMSSTR_CARVE ("                    ");
        vmsfname = UTL$VMSSTR_CARVE (cf -> angles);
        fdab$anginit (vmsfname, lun, molnam, &mbonds, bincr, angoff,
            batom, rbndnum, &nconf, &engflg, &flg13, &flg14);
        engflg = (engflg == 1); flg13 = (flg13 != 0); flg14 = (flg14 !=
0);
        if (!engflg) {
            sprintf (msg, "No energy data in %s; weighting of conformers
equal",
                cf-> angles);
            dab$dut_shomsg (msg);
            }
        UTL$VMSSTR_DISPOSE (molnam);
```

```
      UTL$VMSSTR_DISPOSE (vmsfname);
      if (!(*lun)) return (0); else return (nconf);
      }
} static int q3$eva_nxconf (nxl)
/* SUBROUTINE ============================================== */
/* retrieves from SEARCH file the nxlth conformation after
present one, updating module-wide parameters appropriately */
int nxl;
{
    int i;
    if (!nxl) {
       dab$dut_sho_err ("Illegal rotamer selection criterion");
       return (FALSE);
       }
    for (i = 0; i < nxl; i++) {
       getconf (&mbonds, angoff, angc, &error);
       if (error) goto readerr;
       if (engflg) {
          gtconeng (&eng, &error);
          if (error) goto readerr;
          }
       }
    return (TRUE);

readerr:
    sprintf (msg, "Error reading %d-th rotamer from last", i + 1);
    return (FALSE);
} static int q3$eva_dochange (molarea)
/* SUBROUTINE ============================================== */
/* apply current angle descriptions in SEARCH file to
molecule in work area */
short *molarea;
{
    int i, *i1, *i2, *i3, *i4;
    float value;
    short rcode, three = 3;

for (i = 0; i < mbonds; i++) {
       i1 = &(batom [i][0]); i2 = &(batom [i][1]);
       i3 = &(batom [i][2]); i4 = &(batom [i][3]);
       q3f$tau (i1, i2, i3, i4, molarea, &value);
       value = value - angoff [i];
       change (&three, &value, i1, i2, i3, i4, molarea, &rcode);
       if (!rcode) {
          sprintf (msg, "Bond %d-%d-%d-%d not set to %f", *i1, *i2,
             *i3, *i4, angoff [i]);
          dab$dut_sho_err (msg);
          }
       }
}
```

}

```
int q3$eva_getatid (m, ptnum, fitat)
/* SUBROUTINE =============================================== */
/* returns identifier of atom described by ptnumth point of m
*/
struct q3mol *m;
int ptnum, *fitat;
{
    struct q3atom *atm;

if (ptnum < 0 || ptnum > m -> q3align_rec.natfit) {
       sprintf (msg, "Illegal point id %d", ptnum);
       dab$dut_sho_err (msg); return (FALSE);
       }
     atm = m -> q3align_rec.atm_ptr + ptnum;
     *fitat = atm -> fit_to;
     return (atm -> id);
} int q3$eval_makemissing(tp,icol)
/* SUBROUTINE =============================================*/
/* sets all values in a column to MISSING */
struct tbl_header *tp;
int icol;
{
 int i;

for (i=0; i< tp->nrows; i++)
   dab$dut_p2df(tp->data,tp->coldim,i,icol, D_MISSING);
} int q3$eva_chkatypes (q, qal)
/* SUBROUTINE =============================================== */
/* when aligning using FIT, checks actual number and types of
atoms in molecule vs. point types provided by user */
struct q3plan *q;
struct q3align *qal;
{
    int nat, cfhas;
    struct q3point *pt;
    struct q3atom *at;

if (qal -> natfit < q -> npoints) {
        ferr (); fprintf (fp,
"Fewer fitting atoms in conformer (%d) than plan (%d) - Molecule
skipped\n",
          qal -> natfit, q -> npoints);
        return (FALSE);
        }
    if (qal -> natfit > q -> npoints) {
        fwarn (); fprintf (fp,
"More fitting atoms in conformer (%d) than plan (%d)\n", qal -> natfit,
       q -> npoints);
        }
    if (q -> ignore_atype) return (TRUE);   /* atypes irrelevant */
        for (nat = 0; nat < q -> npoints; nat++) {
          pt = q -> pt_ptr + nat;  at = qal -> atm_ptr + nat;
```

```
            if (pt -> atype != at -> atype) {
                fwarn (); fprintf (fp,
"For atom %d, plan specifies type %d but conformer has type %d\n",
                nat, pt -> atype, at -> atype);
                }
            }
        return (TRUE);
} int q3$eva_npts (rg)
/* SUBROUTINE ================================================ */
/* returns number of lattice points contained in the user
specified region */
struct q3region *rg;
{
    int ncolreg = 1, ncoor;

for (ncoor = 0; ncoor < 3; ncoor++)
            ncolreg *= rg -> nsteps [ncoor];
    return (ncolreg);
} int q3$eva_chkconf (m, cf)
/* SUBROUTINE ================================================ */
/* a stub that checks conformer - action never needed */
struct q3mol *m;
struct q3conf *cf;
{
    return (TRUE);

'if (!(tcptr -> name_ptr = UTL$STR_SAVE(cptr -> name_ptr) ))
            {dab$dut_mem_err ("Names"); return (FALSE);}
        tcptr -> frc_width = 2;
            }
        }
    return (TRUE);
} void q3$eva_store_atom (work_area, atnum, fitatm)
/* SUBROUTINE ================================================ */
/* if alignment rule is FIT, adds a user-specified atom for
alignment to COMPONENT, as describe by fitatm, for fit */
short work_area;
int atnum;
struct q3point *fitatm;
{
    float x, y, z;
    char *caatom, *catc3, *UTL$STR_SAVE(), *q3$lis_aname();

sprintf (msg, "p%-3d", atnum + 1);
    catc3 = UTL$STR_SAVE (msg);

sprintf (msg, "%-4s", q3$lis_aname (fitatm -> atype));
    caatom = UTL$STR_SAVE (msg);

q3$eva_addatom (caatom, catc3,
            (float) fitatm -> coords [0],
```

```
            (float) fitatm -> coords [1],
            (float) fitatm -> coords [2]);

ptwts [atnum] = fitatm -> weight;
    UTL_MEM_FREE (caatom);
    UTL_MEM_FREE (catc3);
} q3$eva_addatom (catc3, caatom, x, y, z)
/* SUBROUTINE ========================================= */
/* actually dispatches add atom call */
char *catc3, *caatom;
float x, y, z;
{
    VMS_String vaatom, vatom_c3, UTL$VMSSTR_CARVE();

vatom_c3 = UTL$VMSSTR_CARVE (catc3);
    vaatom = UTL$VMSSTR_CARVE (caatom);

aatom (vatom_c3, vaatom, &x, &y, &z);

UTL$VMSSTR_DISPOSE (vaatom);
    UTL$VMSSTR_DISPOSE (vatom_c3);
}
            .rowid + 1, errname, cpdname);
            return (FALSE);
            }
    if (dab [tblid] -> rows_named && cpdname) {
        rptr = dab [tblid] -> rowhead + rowid;
        if (!rptr -> name_ptr || strcmp (rptr -> name_ptr, cpdname)) {
            fwarn ();
            fprintf (fp,
"Plan cpd name differs from %s DABYL row # %d name - ", errname, rowid +
1);
            if (rptr -> name_ptr) fprintf (fp, "%s\n", rptr -> name_ptr);
                else fprintf (fp, "??\n");
            }
        }
    return (TRUE);
} int q3$eva_dabio (name, errname, tblid, qcols, qncols, tptr, offset)
/* SUBROUTINE =========================================*/
/* initially opens, reads in bio or chem table, and checks
its columns against user-provided column info */
char *name,          /* file name */
    *errname;        /* goes into error message */
struct q3dab *qcols; /* list of columns to check */
int tblid,           /* table identifier */
    offset,
    qncols;          /* number of columns to check */
struct tbl_header *tptr;
{
    int i;
    struct col_header *cptr, *tcptr;
    char *UTL$STR_SAVE();
```

```c
/* check user-provided column identifiers and names against
those of table */
    for (i = 0; i < qncols; i++) {
        if (!dab$dut_colid_ok (tblid, qcols [i].colid, TRUE)) {
            fprintf (fp, "ERROR: %s Column # %d has illegal column id #
%d\n",
                i+1, qcols [i].colid+1);
            return (FALSE);
        }
        if ((dab [tblid] -> cols_named) && (qcols[i].col_name)) {
            cptr = dab [tblid] -> colhead + qcols [i].colid;
            if ((!cptr -> name_ptr) ||
                (strcmp (cptr -> name_ptr, qcols[i].col_name) )) {
                fprintf (fp,
"WARNING: Column name in Plan '%s' differs from Column name in Table
%s",
qcols [i].col_name, errname);
                if (cptr -> name_ptr) fprintf (fp, "'%s'\n", cptr ->
name_ptr);
                else fprintf (fp, "??\n");
            }
        }
        if (tptr) {
            tcptr = tptr -> colhead + offset + i;

/* puts biological or chemical table data value into the QSAR
table - returns FALSE if MISSING datum transferred */
struct tbl_header *tptr;    /* table transferred from */
int inrow, ndupl;            /* row being transfered from */
struct q3dab *qcols;        /* references identifiers of columns
to transfer */
double *dest;        /* destination */
int destcd,     /* destinations column dimension */
    outrow,    /* identifies row destination */
    ncols;     /* number of values to transfer */
char *errname;   /* type of data */
double weight;   /* weighting factor */
int offset;
struct row_header *rptr;
{
    int i, okdata = TRUE, j;
    double val;
    extern double dab$dut_g2df();
    struct row_header *trptr;
    char *UTL$STR_SAVE();

for (i = 0; i < ncols; i++) {
        val = dab$dut_g2df (tptr -> data, tptr -> coldim, inrow,
            qcols [i].colid);
        if (val == D_MISSING) {
            fwarn ();
            fprintf (fp,
"%s datum EMPTY: %d column, id # %d\n", errname, i+1, qcols[i].colid+1);
            return (FALSE);
        }
        for (j = 0; j < ndupl; j++)
            dab$dut_p2df (dest, destcd, outrow, i *ndupl + offset + j,
                val);
        if (rptr) {
            trptr = tptr -> rowhead + inrow;
            if (trptr -> name_ptr &&
```

```c
            !(rptr -> name_ptr = UTL$STR_SAVE (trptr -> name_ptr)))
                {dab$dut_mem_err ("Labels"); return (FALSE);}
        }
    }
    return (TRUE);
} int q3$eva_dabrow (tblid, rowid, errname, cpdname)
/* SUBROUTINE ================================================ */
/* checks for consistency between user's compound description
and actual bio- or chem- table  row data */
int tblid, rowid;
char *errname, *cpdname;
{
    struct row_header *rptr;

if (!dab$dut_rowid_ok (tblid, rowid, FALSE)) {
        ferr(); fprintf (fp,
            "Row %s not in %s DABYL table - %s skipped\n",
    sybkey = UTL$VMSSTR_CARVE (key);
    par$minvdw (&two, atsht, &eps, sybkey, &errflg);
    if (errflg) {
       sprintf (msg, "Could not find VDW eps for %s - %s interaction",
            q3$lis_aname (anum), q3$lis_aname (probe_type));
       dab$dut_sho_err (msg);
       }
    *b = eps * pow (rad1 + rad2, ((double) Q3D -> ignore_atype));
    *a = 2.0 * eps * pow (rad1 + rad2, 6.0);
    UTL$VMSSTR_DISPOSE (sybkey);
    break;
    }
    return;
} double q3$eva_ceff (anum)
/* SUBROUTINE ================================================ */
/* returns "ceff"  (number of electrons), in Scott-Scheraga,
for anum atomic type */
int anum;
{
    if (anum == 1) return (0.9);
        else if (anum <= 8) return((double) anum );
        else return ( ((double)((anum / 8) + 1)) * 7.0);
} double q3$eva_pol (anum, atype)
/* SUBROUTINE ================================================ */
/* returns "pol"  (polarizability of electrons), in Scott-
Scheraga, for anum atomic type */
int anum, atype;
{
    if (anum == 1) return (0.46);
        else if (anum > 8) return (24.0);
        else return ( 1.5);
}
```

```c
static void ferr()
/* SUBROUTINE ================================================ */
/* prints ERROR */
{ fprintf (fp, "\nERROR: "); } static void fwarn()
{ fprintf (fp, "\nWARNING: "); } static void fskip()
{ fprintf (fp, "Skipping conformer\n");
} int q3$eva_gdata (tptr, inrow, qcols, dest, destcd, outrcw, ncols,
        errname, weight, offset, rptr, ndupl)
/* SUBROUTINE ================================================ */
int q3$eva_VDW_tab (anum, probe_type, a, b, fftype)
/* SUBROUTINE ================================================ */
/* returns van der Waals A and B constant between atoms of
SYBYL type "anum" and "probe_type". If fftype == 1: using
Scott - Scheraga formalism (see Hopfinger, "Conformational
Properties of Macromolecules, pp 45-47). If (fftype == 2: use
SYBYL vdW parameters, recasting these in conventional
Lennard-Jones form */
int anum,
    probe_type;
double *a, *b;    /* the answers */
int fftype;
{
define PLANCK      416.9 double sqrt (), dist, ceff1, ceff2, q3$eva_ceff(), pol1, pol2,
      q3$eva_pol(), rad1, rad2, pow(), dist2;
    int anum1, anum2;
    short atsht[2], at2sht, two = 2, five = 5, errflg = 0;
    VMS_String sybkey, UTL$VMSSTR_CARVE();
    float eps;
    static char key[]={"           "};
    char *q3$lis_aname();

*a = 0.0; *b = 0.0;
    atsht [0] = (short) anum;
    q3f$syb_aprop_int (&(atsht[0]), &five, &anum1);
    if (!anum1) return;            /* a dummy atom */
    atsht [1] = (short) probe_type;
    q3f$syb_aprop_int (&(atsht[1]), &five, &anum2);
    if (!anum2) return;            /* a dummy atom */ q3f$syb_aprop_dbl (&(atsht[0]), &two, &rad1);
    q3f$syb_aprop_dbl (&(atsht[1]), &two, &rad2);

switch (fftype) { case 3:
    dab$dut_shomsg ("Hopfinger not yet implemented; using similar
Original");
case 1:
    ceff1 = q3$eva_ceff (anum1);
    ceff2 = q3$eva_ceff (anum2);
    pol1 = q3$eva_pol (anum1, anum);
    pol2 = q3$eva_pol (anum2, probe_type);
```

```
    *a = PLANCK * pol1 * pol2 /
        (sqrt (pol1 / ceff1) + sqrt (pol2 / ceff2 ));
    dist = rad1 + rad2;
    dist2 = dist * dist;
    dist = dist2 * dist2 * dist2;   /* r6th */
    *b = 0.5 * dist * (*a);
    break;

case 2:
```

/* FFIT.C */

```
/* ffit.c performs FIELD-FIT. After the user is quizzed for
directions and the necessary molecular data are obtained, the
main routine, the first, calls an external Simplex minimizer.
(A minimizer can be thought of as a subroutine that tries to
find a minimum value in some function supplied to it. For
FIELD-FIT, that critical supplied function is the second
subroutine, "q3$ffit_objctv"; the data structures needed by
this routine are also passed through by the Simplex
minimizer.) */ if vax11c
module ffit "V1.0"
endif include stdio
include "dab$source:dabdef.c"
# include "q3d$source:q3def.c"
# include "sys$runsource:vmsstrdef.h"
# define PI_DEG 57.29378

/* data structures used to pass data needed by q3$ffit_objctv
*/ struct ftors {    /* used if torsional variations are requested,
to keep track of which intermolecular interactions vary with
which angles. */
    int at1, at2;       /* identifier numbers, in order, of the
atoms defining a torsion */
    int *aggregate;     /* not used */
    };

struct enrec {    /* needed for internal energy if torsional
variations */
    int natoms;
    double *vdwA, *vdwB, *charges, *atcoords;
    };

struct ffit {    /* data needed by q3$ffit_objctv */
    int natoms,          /* number of atoms in molecule */
        ntrot_df,        /* number of degrees of freedom for
trans/rot - either 0 or 6 */
        ntors,           /* number of torsional rotations */
        pool_se,         /* true if steric and electrostatic
together */
        tblid,           /* ID of a table recording progress; 0 if
none */
        ncalls,          /* number of calls to objective funcn so
far */
        display,         /* true if structure display after each
```

```
10 iterations */
    interrupt_ok,      /* true if user may also interrupt after
display */
    f_difference,      /* true if standard ffit; false if trying
to fit ligand to the field of receptor, rather than field of
another ligand */
    niter2do,          /* maximum number of iterations */
    npoints;           /* number of lattice points in all
regions */
  struct ftors *tors;  /* describes any individual torsions */
    double maxc[3],    /* maxima of region coord vals, for
boundary test */
    minc[3],           /* minima of region coord vals */
    base,              /* basic step size */
    intenergy,         /* internal energy of molecule, before
torsional */
    intweight,         /* internal energy weighting, relative to
field diff */
    oobpart,           /* contribution from any escaping beyond
boundary */
    intenpart,         /* contribution from internal energy */
    fldiffpart,        /* contribution from field difference
ITSELF */
    fldtotal,          /* sum of previous three - value BEING
MINIMIZED */
    *template,         /* field energies being fit to */
    *work,             /* computed energies (scratch) */
    *wts,              /* normalized weights for individual
lattice points */
    *sav_coords,       /* coords of starting molecule */
    *use_coords,       /* coords after current transformation
(scratch) */
    *vdwA,             /* pairwise vdwA value, for each atom
with probe */
    *vdwB,             /* pairwise vdwB value, for each atom
with probe*/
    *charges;          /* product of charges, for each atom with
probe   */
  double *vdwAintra,   /* vdwA for internal energy evaluation */
    *vdwBintra,        /* vdwB for internal energy evaluation */
    *chargesintra;     /* charges for internal energy evaluation
*/
};

q3$ffit_top (batch_int, fitid, one_template, evenwts, merge_se,
basestep, max_iter, converg)
/* MAIN SUBROUTINE ==================== ================ */
/* user call to field fit molecules */
short *batch_int, /* ignored */
    *fitid,          /* identifier of molecule being FIELD FIT
*/
    *one_template,   /* true if only one template molecule */
    *evenwts,        /* true when lattice points weighted same */
    *merge_se,       /* true if steric and electrostatic values at
a lattice point are pooled, rather than considered
independently */
    *max_iter;       /* maximum number of iterations to minimize */
float *basestep,     /* number of Angstroms to move an atom at
first */
```

```c
    *converg;       /* ends when successive steps less than
this */

{
  int fid, doput, maxinter, sim_dim, i, q3$ffit_tabulate(), put_option,
    niter, ok, shoit, intrpt, ffit_conv = TRUE, dotr;
  double basedbl, convdbl, *simplex, *answer, diff, q3$ffit_objctv();
  struct ffit *q3$ffit_get_fit (), *ff;
  short natsht;
  static char yorn[] = {'y','n'};
  static char *templs[] = {"ONE","SEL","ALL"};
  char *mname, *q3$go_batch_setup();

answer = simplex = 0;
/* GET ADDITIONAL INSTRUCTIONS FROM USER */
  shoit = intrpt = FALSE;
  if ((!dab$usr_ynans ("Include translation/rotation", TRUE, TRUE,
&dotr)
     || !dab$usr_getcase ("fit_put_option", &put_option)
     || !dab$usr_ynans ("Display molecule after each 10 iterations",
         TRUE, FALSE, &shoit))
     || (shoit && !dab$usr_ynans ("Allow minimization interruption",
         TRUE, TRUE, &intrpt))
     ) return;

if (!q3$add_ok()) return;

if (!Q3D -> reg_ptr) {
    dab$dut_sho_err ("No Region defined");
    return;
    }
  if (!(dab [0])) {
    dab$dut_sho_err ("No RESULTS present");
    return;
    }

/* get the molecule to fit */
  fid = (int) *fitid - 1;
  if (fid < 0 || fid >= Q3D -> nmols) {
    sprintf (msg, "Plan has %d compounds; %d is illegal", Q3D -> nmols,
        fid - 1);
    dab$dut_sho_err (msg);
    return;
    }
/* is this a 'conventional' ffit or receptor fit ?
(If one MAXIMIZEs rather than MINIMIZEs the difference
between the fields of two molecules (by changing the sign of
the value returned from the objective function), the effect
will be that of finding the optimal docking between the two,
for example of a ligand into a receptor.)
*/
  if ((*one_template) == 1 &&
     !dab$usr_ynans ("Conventional field fit (not receptor)", TRUE,
TRUE,
        &(ffit_conv))) return;

/* get the coord data for the molecule being FIELD FIT */
  ff = 0;
  if (!(ff = q3$ffit_get_fit (fid))) goto free;
  ff -> base = basedbl = (double) *basestep;
  ff -> ntrot_df = dotr ? 6 : 0;
```

```
    convdbl = (double) *converg;
    maxinter = (int) *max_iter;
    ff -> display = shoit;
    ff -> interrupt_ok = intrpt;
    ff -> f_difference = ffit_conv;

/* add the REGION/LATTICE description to the data for the
minimizer - also obtain data for the template molecule(s) */
    if (!q3$ffit_gregion (ff, fid, *evenwts, (*merge_se == 1),
       *one_template)) goto free;

/* allocate the storage needed by the minimizer itself */
    sim_dim = ff -> ntors + ff -> ntrot_df;
    if (!dab$mat_spdbl ( &simplex, (sim_dim + 1) * sim_dim, "")) goto
free;
    if (!dab$mat_spdbl ( &answer, sim_dim, "")) goto free;

q3$ffit_setupsimplex (simplex, ff, basedbl, sim_dim, TRUE, maxinter);

/* do it (call SIMPLEX), passing the function to be called
and the data needed by the function */ if ((niter = SYB_MATH_SIMPLEX (sim_dim, simplex, q3$ffit_objctv, ff,
convdbl, maxinter, q3$ffit_tabulate, ff, answer, &diff)) >= maxinter)
        dab$dut_shomsg ("\07WARNING: SIMPLEX did not converge");

/* report results and apply the resulting transformation to
molecule in M1 display area */
    q3$ffit_wtransform (ff, diff, answer, niter, "Final", TRUE);
    q3$ffit_tsfm_mol (answer, ff);
    natsht = (short) ff -> natoms;
    q3f$syb_putcoords (ff -> use_coords, &M1, &natsht);

display (&M1);
    doput = FALSE;

switch (put_option) {
case 1: doput = TRUE; break;
case 2: if (!dab$usr_ynans ("Replace the Fit Molecule (in the data
base",
        TRUE, TRUE, &doput)) goto free; break;
case 3: doput = FALSE; break;
case 4: q3$ffit_molout(); break;
    }
    if (doput) q3$ffit_put (ff, fid);
       else if (put_option !=4)
           dab$dut_shomsg ("PUT to save the new configuration");
free:
    if (answer) UTL_MEM_FREE (answer);
    if (simplex) UTL_MEM_FREE (simplex);
    q3$ffit_free (ff);
} double q3$ffit_objctv (offsets, ffrec)
/* SUBROUTINE =================================================== */
```

/* the objective function called by the Simplex minimizer:
returns the mean-square energy difference between the
template vector and the energy vector (performing the
operations implied by "offsets" on the molecule before
calculating the energy vector), combined with a repulsive
effect by the boundary and with the internal energy
difference associated with any requested torsions.*/

```c
double *offsets;
struct ffit *ffrec;
{
   int i, nat, nts, nc, vecsize;
   double tsfm [3][3], scratch [3][3], ansr, diff, sqrt(),fabs(),
      nowcoo, q3$ffit_intra(), Q3Dtoobig ;
   short fl = -1;
   static double total;
   struct ftors *nowt;

Q3Dtoobig = fabs(Q3D->too_big);

/* I. APPLY REQUESTED TRANSFORMATIONS */
   if (!q3$ffit_tsfm_mol (offsets, ffrec)) return (1.0e19);

/* II. compute repulsive effect from any portion of molecule
outside of REGIONS?   (beyond boundary) */
   total = 0.0;
   for (i = 0; i < ffrec -> natoms; i++) for (nc = 0; nc < 3; nc++) {
      nowcoo = *(ffrec -> use_coords + 3 * i + nc);
      if (nowcoo < ffrec -> minc [nc])
         total += Q3Dtoobig *
            (ffrec -> minc [nc] - nowcoo) / ffrec -> base;
      else if (nowcoo > ffrec -> maxc [nc])
         total += Q3Dtoobig *
            (nowcoo - ffrec -> maxc [nc]) / ffrec -> base;
      }
   ffrec -> oobpart = total;

/* III. CALCULATE internal ENERGY difference if needed */
   if (ffrec -> ntors) {
      ffrec -> intenpart = (q3$ffit_intra (ffrec) - ffrec -> intenergy);
      total += ffrec -> intweight * ffrec -> intenpart;
      }

/* IV. CALCULATE THE field for this alignment of the molecule
being FIELD-FIT (only if needed - the difference in fields
may be swamped by internal energy or region edge effects */
if (total < 2.0 * Q3Dtoobig) {
/* zero work */
   vecsize = ffrec -> pool_se ? ffrec -> npoints : 2 * ffrec -> npoints;
   for (i = 0; i < vecsize; i++) ffrec -> work [i] = 0.0;

q3$eva_enrgy (ffrec -> use_coords,
      ffrec -> pool_se ? 0 : ffrec -> npoints,
      ffrec -> natoms,
      ffrec -> vdwB,
      ffrec -> vdwA,
      ffrec -> charges,
      ffrec -> work,
```

```
      1.0,
         &f1);

/* V. CALCULATE THE mean square field difference (or sum) -
note that this may be weighted differently for each lattice
point */
   ansr = 0.0;
   for (i = 0; i < vecsize; i++) {
      diff = ffrec -> f_difference ?
            ffrec -> work [i] - ffrec -> template [i] :
            ffrec -> work [i] + ffrec -> template [i] ;
      ansr +=     ffrec -> wts [i] * diff * diff;
      }
   total += (ffrec -> fldiffpart = sqrt (ansr / (double) vecsize));
   ffrec->fldtotal = total;
   }

(ffrec -> ncalls)++;
  return (total);
} static int q3$ffit_tsfm_mol (offsets, ffrec)
/* SUBROUTINE =========================================== */
/* applies the transformations in offsets to the molecule
whose coords are in ff->sav_coords, putting them in ff-
>use_coords */
double *offsets;
struct ffit *ffrec;
{
   int i, j, nat, nts, nc, vecsize;
   double tsfm [3][3], scratch [3][3], scratch2 [3][3], ansr, diff,
sqrt ();
   static double pivot [3] = {0.0, 0.0, 0.0}; /* KEEP AS ZERO!!! */
   struct ftors *nowt;

/* restore use_coords */
   for (nat = 0 ; nat < 3*ffrec -> natoms; nat++)
      *(ffrec -> use_coords + nat) = *(ffrec -> sav_coords + nat);

/* apply torsional rotations to the appropriate atoms */
   for (nts = 0; nts < ffrec -> ntors; nts++) {
      nowt = ffrec -> tors + nts;
      if (offsets [nts + ffrec -> ntrot_df]) {
         UTL_GEOM_MFORM (ffrec -> use_coords + 3*(nowt ->at1 - 1),
            ffrec -> use_coords + 3*(nowt ->at2 - 1),
            offsets [nts + ffrec -> ntrot_df], tsfm);

for (nat = 0; nat < ffrec -> natoms; nat++)
           if (dab$bit_isiton (nowt -> aggregate, nat))
           UTL_GEOM_ROTATE ( ffrec -> use_coords + 3*(nowt ->at2 - 1),
               tsfm, &(ffrec -> use_coords [nat*3]));
         }
      }

/* perform global rotations */
if (ffrec -> ntrot_df) {
```

```
        UTL_GEOM_IDENTITY_M (tsfm);
        for (nc = 0; nc < 3; nc++) if (offsets [nc + 3]) {
            switch (nc) {
case 0:        UTL_GEOM_MAKE_ROTX (offsets [nc + 3] / PI_DEG, scratch);
break;
case 1:        UTL_GEOM_MAKE_ROTY (offsets [nc + 3] / PI_DEG, scratch);
break;
case 2:        UTL_GEOM_MAKE_ROTZ (offsets [nc + 3] / PI_DEG, scratch);
break;
            }
        UTL_GEOM_MMULT (tsfm, scratch, scratch2);
        for (i = 0; i < 3; i++) for (j = 0; j < 3; j++)
            tsfm [i][j] = scratch2 [i][j];
        }
        UTL_GEOM_MROTATE (tsfm, pivot, ffrec -> natoms, ffrec -> use_coords);

/* perform global translations */
        for (nc = 0; nc < 3; nc++) if (offsets [nc])
            for (nat = 0; nat < ffrec -> natoms; nat++)
                ffrec -> use_coords [nat * 3 + nc] += offsets [nc];
    } return (TRUE);

err:
    dab$dut_sho_err("illegal bond rotation attempted");
    return (FALSE); /* report error */
} static q3$ffit_end_setup (mname)
/* SUBROUTINE ================================================ */
/* ends a batch file setup run */
char *mname;
{
    fprintf (fp, " %s\n", mname);
    fclose (fp);
    fp = stdout;
} static q3$ffit_molout()
/* SUBROUTINE ================================================ */
/* adds a NEW molecule into the molecule data base, after
field fit */
{
    static char molname [D_MAX_STLG];
    VMS_String vname, UTL$VMSSTR_CARVE();
    short two = 2;
    int nok;

do {
        if (!dab$usr_cmtext ("mol_name", msg)) return;
        if ((nok = strchr (msg, '.'))) dab$dut_sho_err ("No file extnsn");
    } while (nok);
    sprintf (molname, "%s.mol", msg);
    vname = UTL$VMSSTR_CARVE (molname);
    dbmol (&two, &M1, vname);
```

```
static q3$ffit_put (ff, fid)
/* SUBROUTINE ============================================= */
/* REPLACES the entry in the data base with the field fit
mol*/
struct ffit *ff;
int fid;
{
    struct q3mol *m;
    struct q3conf *cf;
    short ids;

m = Q3D -> mol_ptr + fid;
    q3$mol_dbaseopen (m, FALSE);
    cf = m -> cnf_ptr;
    ids = (short) cf -> id;
    dbput (&M1, &ids);
} static int q3$ffit_setupsimplex (simplex, ff, basestep, sim_dim,
dotable, maxiter)
/* SUBROUTINE ============================================= */
/* provides initial trial values (rotations, translation,
torsions), for SIMPLEX minimization. Also initializes a user-
accessible output table for intermediate stage data, if
requested */
int sim_dim, dotable, maxiter;
double basestep, *simplex;
struct ffit *ff;
{
    int i, nc, nt, nclab;
    struct ftors *tor;
    static double centroid[3] ;
    double maxdist, nowdist, UTL_GEOM_VDIST(), UTL_GEOM_VDIST_SQ(),
stepsize,
        sqrt();
    short nr, snc, zero = 0, tbl;
    struct tbl_header *tptr;
    struct col_header *cptr;
    char *UTL$STR_SAVE();

centroid[0]= centroid[1]= centroid[2] =0.0 ;

/* compute centroid of test mol */
    for (i = 0; i < ff -> natoms; i++) for (nc = 0; nc < 3; nc++)
        centroid [nc] += *(ff -> sav_coords + i*3 + nc);
    for (nc = 0; nc < 3; nc++) centroid [nc] /= (double) (ff -> natoms);

/* compute max distance of any atom from centroid */
    for (i = 0, maxdist = 0.0; i < ff -> natoms; i++)
        if ((nowdist = UTL_GEOM_VDIST_SQ (centroid, ff -> sav_coords +
i*3))
            > maxdist) maxdist = nowdist;
    maxdist = sqrt (maxdist);
```

```
/* translations */
if (ff -> ntrot_df) {
   dab$dut_p2df (simplex, sim_dim, 1, 0, basestep);
   dab$dut_p2df (simplex, sim_dim, 2, 1, basestep);
   dab$dut_p2df (simplex, sim_dim, 3, 2, basestep);
   for (i = 0; i < 3; i++) for (nc = 0; nc <= sim_dim; nc++)
      *(simplex + sim_dim*nc + i) -= basestep / 2.0;

/* rotations, in degrees */
   stepsize = basestep * PI_DEG / maxdist;
   dab$dut_p2df (simplex, sim_dim, 4, 3, stepsize);
   dab$dut_p2df (simplex, sim_dim, 5, 4, stepsize);
   dab$dut_p2df (simplex, sim_dim, 6, 5, stepsize);
   for (i = 3; i < 6; i++) for (nc = 0; nc <= sim_dim; nc++)
      *(simplex + sim_dim*nc + i) -= stepsize / 2.0;
   }

/* torsionals, in degrees - how far is rotated group from
center? */
   for (nt = 0; nt < ff -> ntors; nt++) {
      tor = ff -> tors + nt;
      stepsize = basestep * PI_DEG
/ (maxdist - UTL_GEOM_VDIST (centroid, ff -> sav_coords +
            3*(tor -> at2 - 1) ));
      dab$dut_p2df (simplex, sim_dim, nt + ff -> ntrot_df + 1,
            nt + ff -> ntrot_df, stepsize);
      for (nc = 0; nc <= sim_dim; nc++)
         *(simplex + sim_dim*nc + nt + ff -> ntrot_df) -= stepsize / 2.0;
      }

/* set up table if desired */
   if (dotable) {
      if ((ff -> tblid = dab$ini_tblid()) < 0)
         dab$dut_shomsg ("WARNING: Minimization NOT saved to table");
      else {
      tbl = (short) ff -> tblid;
      nr = (short) maxiter + sim_dim;
      ff -> niter2do = maxiter;
      snc = sim_dim + 5;
      if (!dab$ini_table (&tbl, &nr, &snc, &zero, &zero, &tbl))
         ff -> tblid = 0;
         else {
         tptr = dab [ff -> tblid];
         tptr -> nrows = 0;
         tptr -> cols_named = TRUE;
         nclab = 0;
         if (ff -> ntrot_df) for (nclab = 0; nclab < 6; nclab++) {
            cptr = tptr -> colhead + nclab;
            switch (nclab) {
case 0:     sprintf (msg, "X Tran"); break;
case 1:     sprintf (msg, "Y Tran"); break;
case 2:     sprintf (msg, "Z Tran"); break;
case 3:     sprintf (msg, "X Rotn"); break;
case 4:     sprintf (msg, "Y Rotn"); break;
case 5:     sprintf (msg, "Z Rotn"); break;
            }
            cptr -> frc_width = 5;
            cptr -> num_width = 11;
```

```c
            cptr -> name_ptr = UTL$STR_SAVE (msg);
            }
            for (nt = 0; nt < ff -> ntors; nt++) {
            cptr = tptr -> colhead + nclab;
            sprintf (msg, "Tors %d", nt + 1);
            cptr -> name_ptr = UTL$STR_SAVE (msg);
            nclab++;
            }
        cptr = tptr -> colhead + nclab;
        sprintf (msg, "Total");
        cptr -> name_ptr = UTL$STR_SAVE (msg);
        nclab++;
        cptr = tptr -> colhead + nclab;
        sprintf (msg, "OOB Enrgy");
        cptr -> name_ptr = UTL$STR_SAVE (msg);
        nclab++;
        cptr = tptr -> colhead + nclab;
        sprintf (msg, "Intrnl Enrgy");
        cptr -> name_ptr = UTL$STR_SAVE (msg);
        nclab++;
        cptr = tptr -> colhead + nclab;
        sprintf (msg, "RMS Fld diff");
        cptr -> name_ptr = UTL$STR_SAVE (msg);
        nclab++;
        cptr = tptr -> colhead + nclab;
        sprintf (msg, "Total diff");
        cptr -> name_ptr = UTL$STR_SAVE (msg);
    }
      }
   }
} int *q3$ffit_arr2set(setarr, id)
/* SUBROUTINE ===============================================*/
/* utility, returns idth set from setarr, an array of sets - not
currently used */
int *(setarr[]), id;
{
    return (setarr [id]);
}
define VALID_CHARGES 2 static struct ffit *q3$ffit_get_fit (fid)
/* SUBROUTINE =============================================== */
/* fills in data for field-fit on molecule being fit */
int fid;
{
    struct q3mol *m;
    struct q3conf *cf;
    struct ffit *f;
    struct ftors *ft;
    char err;
    int dotors, anow, natm, i, j, abort, at1, at2, typ1, typ2, i1, i2,
      atst, atend, *q3$ffit_arr2set();
    short natsht, zero = 0, fopen_flg = -1, chndx, stat, premeth, ishort;
    double dab$dut_g2df(), unit = 1.0, charge1, q3$ffit_intra();
```

```c
/* open VDW parameter data base */
   if (Q3D -> ffield == 2) {
     par$open_minvdw (&zero, &fopen_flg);
     if (fopen_flg) {
        dab$dut_sho_err ("Could not open SYBYL parameter file");
        return (FALSE);
        }
     }
/* open molecule data base */
   m = Q3D -> mol_ptr + fid;
   if (!q3$mol_dbaseopen (m, FALSE)) {
      dab$dut_sho_err ("Can't find dbase for molecule to fit");
      return (FALSE);
      }
/* read in molecule */
   if (m -> nconfs > 1) dab$dut_shomsg ("Using conformer 1");
   cf = m -> cnf_ptr;
   dbget0 (&M1, &(cf -> id), &err);
   if (err != LOG1FALSE) {
      dab$dut_shomsg ("Could not GET molecule to fit");
      return (FALSE);
      }
/* get number atoms in mol */
   q3f$syb_gnatoms (&M1, &natm);

/* allocate storage needed for mol data in field-fit
procedure */
   if (!(f = (struct ffit *) UTL_MEM_CALLOC (1, sizeof (struct ffit)) ))
{
     dab$dut_mem_err ("Fit record");
     return (FALSE);
     }
   f-> sav_coords = f-> use_coords = f -> vdwA = f -> vdwB = f ->
charges =
      f->work = f-> wts = f-> template = f -> vdwAintra = f -> vdwBintra
= f -> chargesintra = 0;
   f -> tors = 0;
   if (!dab$mat_spdbl (&(f -> sav_coords), 3 * natm, "")) goto free;
   if (!dab$mat_spdbl (&(f -> use_coords), 3 * natm, "")) goto free;
   if (!dab$mat_spdbl (&(f -> vdwA), natm, "")) goto free;
   if (!dab$mat_spdbl (&(f -> vdwB), natm, "")) goto free;
   if (!dab$mat_spdbl (&(f -> charges), natm, "")) goto free;
   natsht = (short) natm;

/* copy atomic coords to here */
   q3f$syb_getcoords (f -> sav_coords, &M1, &natsht);
   f -> natoms = natm;

/* copy atomic charges and VDW parameters to here */
   fndchg (&chndx, &stat, &premeth, &M1);
   if (stat != VALID_CHARGES) {
     dab$dut_sho_err ("Invalid charges in fit mol");
     goto free;
     }
   for (i = 0, ishort = 1; i < natm; i++, ishort++) {
     q3f$echarge (&chndx, &ishort, &M1, &(Q3D -> probe_charge),
        &(f -> charges [i]));
```

```
      j = i + 1;
      q3f$syb_atype (&j, &M1, &anow);
      q3$eva_VDW_tab (anow, Q3D -> probe_type, &(f -> vdwA [i]),
           &(f -> vdwB [i]), Q3D -> ffield);
      }

/* get torsional parameters from user, if any */
   if (!dab$usr_ynans ("Include torsional variations", TRUE, FALSE,
&dotors))
      goto free;

if (dotors) {
/* how many torsions are there? */
    if (!dab$usr_cmgetreal ("INTENWEIGHT", &(f -> intweight ))) goto
free;
    edit (&M1);
    display (&M1);
    if (!dab$usr_cmgetbint ("ffit_ntorsions", 0, 100, &(f -> ntors)))
goto free;

/* allocate storage for torsion descriptions */
    if (f -> ntors) {
       if (!(f -> tors = (struct ftors *) UTL_MEM_CALLOC (f -> ntors,
           sizeof (struct ftors))) ) {
          dab$dut_mem_err ("");
          goto free;
          }
       if (!dab$mat_spdbl (&(f -> vdwAintra), natm * natm, "")) goto free;
       if (!dab$mat_spdbl (&(f -> vdwBintra), natm * natm, "")) goto free;
       if (!dab$mat_spdbl (&(f -> chargesintra), natm * natm, "")) goto
free;
       for (i = 0; i < f -> ntors; i++) {
          ft = f -> tors + i;
          ft -> aggregate = 0;
          }
       for (i = 0; i < f -> ntors; i++) {
          ft = f -> tors + i;
          if (!dab$mat_spbit (&(ft -> aggregate), natm, "")) goto free;
          }
       for (i = 0; i < f -> ntors; i++) {
          ft = f -> tors + i;
          q3$ff_getors (&(ft -> at1), &(ft -> at2), &(ft -> aggregate),
             &at1, &at2, &M1, &abort);
          if (abort) goto free;
          }

/* set up internal energy params for torsions */
       for (at1 = 0, i1 = 1; at1 < natm; at1++, i1++) {
          ishort = (short) i1;
          q3f$echarge (&chndx, &ishort, &M1, &unit, &charge1);
          for (at2 = 0, i2 = 1; at2 < at1; at2++, i2++) {
             q3f$syb_atype (&i1, &M1, &typ1);
             q3f$syb_atype (&i2, &M1, &typ2);
             q3$eva_VDW_tab (typ1, typ2,
                f -> vdwAintra + natm * at1 + at2,
                f -> vdwBintra + natm * at1 + at2,
                Q3D -> ffield);
             ishort = (short) i2;
```

```c
        q3f$echarge (&chndx, &ishort, &M1, &charge1,
         f->chargesintra + natm * at1 + at2);
        dab$dut_p2df (f->vdwAintra, natm, at2, at1,
         dab$dut_g2df (f->vdwAintra, natm, at1, at2));
        dab$dut_p2df (f->vdwBintra, natm, at2, at1,
         dab$dut_g2df (f->vdwBintra, natm, at1, at2));
        dab$dut_p2df (f->chargesintra, natm, at2, at1,
         dab$dut_g2df (f->chargesintra, natm, at1, at2));
        }
      } /* at1 */
    }

/* get initial internal energy */
    for (at1 = 0; at1 < 3 * natm; at1++)
        *(f -> use_coords + at1) = *(f -> sav_coords + at1);
    f -> intenergy = q3$ffit_intra (f);
    }
    if (!fopen_flg) par$close_minvdw ();
    return (f);

free:
    if (!fopen_flg) par$close_minvdw ();
    q3$ffit_free (f);
    return (FALSE);
} static int q3$ffit_free_enrec (mprop)
/* SUBROUTINE =================================================== */
/* utility to return temporary storage to operating system*/
struct enrec *mprop;
{
    if (mprop->vdwA) UTL_MEM_FREE (mprop->vdwA);
    if (mprop->vdwB) UTL_MEM_FREE (mprop->vdwB);
    if (mprop->atcoords) UTL_MEM_FREE (mprop->atcoords);
    if (mprop->charges) UTL_MEM_FREE (mprop->charges);
} static int q3$ffit_gregion (ff, fitid, evenwts, merge_se, temp_option)
/* SUBROUTINE =================================================== */
/* adds region-dependent data to ff, plus the data for all
the template molecule(s), plus any individual weighting of
lattice points, for example weighting by the current CoMFA
QSAR coefficients. */
struct ffit *ff;
int fitid, evenwts, merge_se, temp_option;
{
    int i, j, nr, nlcol = 0, wtid, ntempmol, templ_id, done,
one_template,
        cl = 1, *results, success = FALSE;
    double sum, wtval, *coeff, fabs();
    struct q3region *r;
    struct ana_header *a;
    short zero = 0, fopen_flg = -1;
    struct enrec mprop;

mprop.natoms = 0;
```

```
    mprop.atcoords = mprop.vdwA = mprop.vdwB = mprop.charges = 0;

for (nr = 0; nr < Q3D -> nregions; nr++)
        nlcol += q3$eva_npts (Q3D -> reg_ptr + nr);
    ff -> npoints = nlcol;
    ff -> pool_se = merge_se;
    if (!merge_se) nlcol *= 2;

if (Q3D -> ffield == 2) {
        par$open_minvdw (&zero, &fopen_flg);
        if (fopen_flg) {
            dab$dut_sho_err ("Could not open SYBYL parameter file");
            return (FALSE);
            }
        }
    if (!dab$mat_spdbl (&(ff -> template), nlcol, "")) return (FALSE);
    if (!dab$mat_spdbl (&(ff -> work), nlcol, "")) return (FALSE);
    if (!dab$mat_spdbl (&(ff -> wts), nlcol, "")) return (FALSE);

/* get the template (s) */
    ntempmol = 0;
    switch (temp_option) {
    case 1:
    case 2:
        one_template = (temp_option == 1);
        do {        /* until all templates entered or only one both
  needed and entered */
            do {    /* until legitimate mol identifier obtained */
                done = !dab$usr_cmgetbint ("ffd_temp_id", 1, Q3D -> nmols,
&templ_id);
                if (done && !ntempmol) return (FALSE);
                templ_id--;
                if (!done && templ_id == fitid)
                    dab$dut_sho_err ("Cannot fit to oneself");
                } while (!done && templ_id == fitid);
            if (!done || one_template) {
                ntempmol++;
                if (!q3$ffit_get_field (templ_id, &mprop, ff)) goto free;
                }
            } while (!done && !one_template);
        break;
    case 3:
        for (templ_id = 0; templ_id < dab[0] -> nrows; templ_id++)
            if (templ_id != fitid) {
                ntempmol++;
                if (!q3$ffit_get_field (templ_id, &mprop, ff)) goto free;
                }
        break;
        } for (i = 0; i < nlcol; i++) ff -> template [i] /= (double) ntempmol;

/* get the weights for each lattice point in the Field Fit */
    for (i = 0; i < nlcol; i++) ff -> wts [i] = 1.0;
    if (evenwts > 1) {
        switch (evenwts) {
    case 2:     /* weight by QSAR coefficients */
        a = dab[0] -> anahead;
```

```c
        if (!(results = (int *) a -> results)) {
            dab$dut_sho_err ("No QSAR to weight lattice points by");
            return (FALSE);
        }
        dab$pls4_getint (&results, &coeff, &cl);
        for (i = 0; i < nlcol; i++) ff -> wts [i] = fabs (coeff [i]);
        break;
    case 3: /* user allowed to weight each point differently */
        while (dab$usr_getbint ("ffd_pt_id", 1, merge_se ? nlcol : nlcol /
2, &wtid)) if (dab$usr_cmgetreal ("ffd_pt_wt", &wtval)) {
            ff -> wts [wtid - 1] = wtval;
            if (!merge_se) ff -> wts [wtid + nlcol/2 - 1] = wtval;
        }
        break;
    }

/* normalize weights */
    for (i = 0, sum = 0.0; i < nlcol; i++) sum += ff -> wts [i];
    sum = (double) nlcol / sum;
    for (i = 0; i < nlcol; i++) ff -> wts [i] *= sum;
    }

/* compute max and min region coordinates */
    r = Q3D -> reg_ptr;
    for (i = 0; i < 3; i++) {
        ff -> minc [i] = r -> lo_coords [i];
        ff -> maxc [i] = r -> lo_coords [i] + (r -> nsteps [i] - 1) *
            r -> step_size [i];
    }
    for (j = 1; j < Q3D -> nregions; j++) {
        r = Q3D -> reg_ptr + j;
        for (i = 0; i < 3; i++) {
            if (ff -> minc [i] > r -> lo_coords [i])
                ff -> minc [i] = r -> lo_coords [i];
            if (ff -> maxc [i] < r -> lo_coords [i] + (r -> nsteps [i] - 1) *
                    r -> step_size [i])
                ff -> maxc [i] = r -> lo_coords [i] + (r -> nsteps [i] - 1) *
                    r -> step_size [i];
        }
    }
    success = TRUE;
free:
    q3$ffit_free_enrec (&mprop);
    if (!fopen_flg) par$close_minvdw ();
    return (success);
} static int q3$ffit_get_field (fid, mprop, ffrec)
/* SUBROUTINE ============================================== */
/* adds field data on one template molecule to the Field-fit
data    - routine resembles q3$ffit_get_fit but simpler */
int fid;
struct enrec *mprop;
struct ffit *ffrec;
{
    struct q3mol *m;
    struct q3conf *cf;
```

```c
struct ffit *f;
struct ftors *ft;
char err;
int dotors, anow, natm, i, j, abort, at1, at2, typ1, typ2, i1, i2,
    atst, atend, *q3$ffit_arr2set();
short natsht, chndx, stat, premeth, ishort, fl = -1;
double dab$dut_g2df(), unit = 1.0, charge1, q3$ffit_intra();

m = Q3D -> mol_ptr + fid;
if (!q3$mol_dbaseopen (m, FALSE)) {
   dab$dut_sho_err ("Can't find dbase for molecule to fit");
   return (FALSE);
}
if (m -> nconfs > 1) dab$dut_shomsg ("Using conformer 1");
cf = m -> cnf_ptr;
dbget0 (&M1, &(cf -> id), &err);
if (err != LOG1FALSE) {
   dab$dut_shomsg ("Could not GET molecule to fit");
   return (FALSE);
}
q3f$syb_gnatoms (&M1, &natm);
if (natm > mprop -> natoms) {
   q3$ffit_free_enrec (mprop);
   mprop -> natoms = natm;
   if (!dab$mat_spdbl (&(mprop -> atcoords), 3 * natm, "")) goto free;
   if (!dab$mat_spdbl (&(mprop -> vdwA), natm, "")) goto free;
   if (!dab$mat_spdbl (&(mprop -> vdwB), natm, "")) goto free;
   if (!dab$mat_spdbl (&(mprop -> charges), natm, "")) goto free;
}
natsht = (short) natm;
q3f$syb_getcoords (mprop -> atcoords, &M1, &natsht);

fndchg (&chndx, &stat, &premeth, &M1);
if (stat != VALID_CHARGES) {
   dab$dut_sho_err ("Invalid charges in fit mol");
   goto free;
}
for (i = 0, ishort = 1; i < natm; i++, ishort++) {
   q3f$echarge (&chndx, &ishort, &M1, &(Q3D -> probe_charge),
        &(mprop -> charges [i]));
   j = i + 1;
   q3f$syb_atype (&j, &M1, &anow);
   q3$eva_VDW_tab (anow, Q3D -> probe_type, &(mprop -> vdwA [i]),
        &(mprop -> vdwB [i]), Q3D -> ffield);
} q3$eva_enrgy (mprop -> atcoords,
   ffrec -> pool_se ? 0 : ffrec -> npoints,
   mprop -> natoms,
   mprop -> vdwB,
   mprop -> vdwA,
   mprop -> charges,
   ffrec -> template,
   1.0,
   &fl);

return (TRUE);
```

```
free:
    q3$ffit_free (f);
    return (FALSE);
} static void q3$ffit_free (f)
/* SUBROUTINE ============================================== */
/* frees all storage allocated for purposes of performing
field fit */
struct ffit *f;
{
    struct ftors *ft;
    int i;

if (!f) return;
    if (f->vdwA) UTL_MEM_FREE (f->vdwA);
    if (f->vdwB) UTL_MEM_FREE (f->vdwB);
    if (f->vdwAintra) UTL_MEM_FREE (f->vdwAintra);
    if (f->vdwBintra) UTL_MEM_FREE (f->vdwBintra);
    if (f->sav_coords) UTL_MEM_FREE (f->sav_coords);
    if (f->use_coords) UTL_MEM_FREE (f->use_coords);
    if (f->charges) UTL_MEM_FREE (f->charges);
    if (f->chargesintra) UTL_MEM_FREE (f->chargesintra);
    if (f->work) UTL_MEM_FREE (f->work);
    if (f->template) UTL_MEM_FREE (f->template);
    if (f->wts) UTL_MEM_FREE (f->wts);
    if (f->tors) {
     for (i = 0; i < f -> ntors; i++) {
          ft = f -> tors + i;
          if (ft -> aggregate) UTL_MEM_FREE (ft -> aggregate);
          }
     UTL_MEM_FREE (f->tors);
     }
    UTL_MEM_FREE (f);
} static double q3$ffit_intra (ff)
/* SUBROUTINE ============================================== */
/* calculates internal non-bonded energy for coordinates in
use_coords; necessary when torsional variations are being
done. (uses 1/r dielectric) */
struct ffit *ff;
{
  int i, nt, at1, at2, nc;
  double ans = 0.0, diff, dist, dis6, dis12;

for (at1 = 0; at1 < ff -> natoms; at1++) for (at2 = 0; at2 < at1;
at2++) {
       for (nc = 0, dist = 0.0; nc < 3; nc++) {
           diff = *(ff -> use_coords + 3 * at1 + nc)
                 - *(ff -> use_coords + 3 * at2 + nc);
           dist += diff * diff;
           }
        if (dist == 0.0) return (1.0e19);     /* atoms overlap */
       dis6 = dist * dist * dist;
       dis12 = dis6 * dis6;
```

```c
        ans += (*(ff -> vdwBintra + (ff -> natoms) * at1 + at2)) / dis12;
        ans -= (*(ff -> vdwAintra + (ff -> natoms) * at1 + at2)) / dis6;
        ans += (*(ff -> chargesintra + (ff -> natoms) * at1 + at2)) / dist;
        }
    return (ans);
} int q3$ffit_tabulate (ncalls, ansr, offsets, ffrec)
/* SUBROUTINE ============================================ */
/* called by SIMPLEX; saves intermediate data to table after
each iteration, if requested by user */
int ncalls;   /* ignored */
double ansr, *offsets;
struct ffit *ffrec;
{
    struct tbl_header *tptr;
    int ok = TRUE, i;
    short natsht, one = 1, tblsht, n2add;

if (ffrec -> tblid) {
        tptr = dab [ffrec -> tblid];
        if (!tptr -> nrows) q3$ffit_wtransform (ffrec, ansr, offsets, 1,
            "Initial", FALSE);
        if (tptr -> nrows == tptr -> rowdim) {
            tblsht = (short) ffrec -> tblid;
            n2add = (short) ffrec -> niter2do;
            dab$bigger (&tblsht, &one, &n2add, &one);
            }
        (tptr -> nrows)++;

for (i = 0; i < ffrec -> ntrot_df + ffrec -> ntors; i++)
            dab$dut_p2df (tptr -> data, tptr -> coldim, tptr -> nrows - 1,
i,  offsets [i]);
        dab$dut_p2df (tptr -> data, tptr -> coldim, tptr -> nrows - 1,
            ffrec -> ntors + ffrec -> ntrot_df, ansr);
        dab$dut_p2df (tptr -> data, tptr -> coldim, tptr -> nrows - 1,
            ffrec -> ntors + ffrec -> ntrot_df+1, ffrec -> oobpart);
        dab$dut_p2df (tptr -> data, tptr -> coldim, tptr -> nrows - 1,
            ffrec -> ntors + ffrec -> ntrot_df+2, ffrec -> intenpart);
        dab$dut_p2df (tptr -> data, tptr -> coldim, tptr -> nrows - 1,
            ffrec -> ntors + ffrec -> ntrot_df+3, ffrec->fldiffpart);
        dab$dut_p2df (tptr -> data, tptr -> coldim, tptr -> nrows - 1,
            ffrec -> ntors + ffrec -> ntrot_df+4, ffrec->fldtotal);
        if (!(tptr -> nrows % 10) && ffrec -> display) {
            sprintf (msg, "After %d iterations, energy diff = %f kcal/mol-point",
            tptr -> nrows, ansr);
            dab$dut_shomsg (msg);
            natsht = (short) ffrec -> natoms;
            q3f$syb_putcoords (ffrec -> use_coords, &M1, &natsht);
            display (&M1);
            if (ffrec -> interrupt_ok &&
              !dab$usr_ynans ("Continue", TRUE, TRUE, &ok)) ok = FALSE;
            }
    }
```

```
    return (ok);
} static void q3$ffit_wtransform (ff, diff, answer, niter, calltype,
    shotsf)
/* SUBROUTINE ============================================== */
/* writes answer, energy, to the users's terminal */
struct ffit *ff;
double diff, *answer;
int niter, shotsf;
char *calltype;
{
    int i;
    static cooch [3] = {'X','Y','Z'};
    struct ftors *tor;

sprintf (msg, "%s difference = %f kcal / mol-point", calltype, diff);
    dab$dut_shomsg (msg);
    if (!shotsf) return;

sprintf (msg, "(%d iterations, %d function calls)", niter, ff ->
ncalls);
    dab$dut_shomsg (msg);
 if (ff -> ntrot_df) {
    for (i = 0; i < 3; i++) {
        sprintf (msg, " Translation of %f Angstrom along %c axis",
            answer[i], cooch[i]);
        dab$dut_shomsg (msg);
    }
    for (i = 0; i < 3; i++) {
        sprintf (msg, " Rotation of %f degrees about %c axis", answer[i+3],
cooch[i
]);
        dab$dut_shomsg (msg);
    }
}
    for (i = 0; i < ff -> ntors; i++) {
        tor = ff -> tors + i;
        sprintf (msg, " Rotation of %f degrees about %d - %d bond",
            answer[i+ ff -> ntrot_df],
            tor -> at1, tor -> at2);
        dab$dut_shomsg (msg);
    }
}
```

```
C                          PLS.FOR
C       PROGRAM NEWPLS
C
C
C       NEW PLS with bootstrap and cross validation and centering option
C       REAL*8 X(1000),Y(1000),WEYT(100),BETA(2200),SCRTCH(4000)
C       *,YPRED(1000),RES(1100),W1(100),W2(100),B(100),PRESS(220)
C       *,U(1000),V(1000),RO(10),XBAR(20),OFF(220),EPS,SS(22),R2(22),
C       *CR2(220),WEYTB(100)
C       DIMENSION XXX(100),YYY(100),X1(100)
C       INTEGER*4 NPAT,NVAR1,NVAR2,NCOMP,NITMAX,IERR,ICROS,IBOOT,ICENT,
C       *IX(100),NOPT(22)
C       DATA NITMAX,EPS/100,0.0001/
C       REWIND 11
```

```
C       WRITE(6,3)
C  3    FORMAT(/' GIVE NPAT,NVAR1,NVAR2,NCOMP,ICROS,IBOOT,ICENT')
C       READ(5,*) NPAT,NVAR1,NVAR2,NCOMP,ICROS,IBOOT,ICENT
C       READ(11,*)(WEYT(I),I=1,NPAT)
C       DO 1 I=1,NPAT
C       L1=(I-1)*NVAR1+1
C       L2=I*NVAR1
C       L3=(I-1)*NVAR2+1
C       L4=I*NVAR2
C       READ(11,*)(X(L),L=L1,L2),(Y(L),L=L3,L4)
C  1    CONTINUE
C       READ(11,12)(X1(I),I=1,NPAT)
C  12   FORMAT(19A4/)
C       IF(IBOOT.EQ.0) IBOOT1=1
C
C          MAIN PLS DRIVER
C
C       CALL PLS(NPAT,NVAR1,NVAR2,NCOMP,NITMAX,EPS,IBOOT,ICROS,ICENT,
C      *X,Y,WEYT,WEYTB,XBAR,OFF,BETA,W1,W2,B,U,V,RO,SS,R2,PRESS,CR2,NOPT,
C      *YPRED,RES,IERR,SCRTCH,IX)
C       WRITE(6,69) IERR
C  69   FORMAT(/' IERR: ',I4)
C       WRITE(6,2)(XBAR(J),J=1,NVAR1+NVAR2)
C  2    FORMAT(/' AVERAGES:'/(5F15.4))
C       IBIC=IBOOT+2
C       IF(IBOOT1.EQ.1) IBIC=ICROS
C       DO 65 IB=1,IBIC
C       J1=(IB-1)*NVAR2+1
C       J2=IB*NVAR2
C       WRITE(6,6)(OFF(J),J=J1,J2)
C  6    FORMAT(/' OFFSETS:'/(5F15.4/))
C  65   CONTINUE
C       IBIC=IBOOT+2
C       IF(IBOOT1.EQ.1) IBIC=ICROS
C       DO 666 IB=1,IBIC
C       DO 66 I=1,NVAR2
C       L1=(IB-1)*NVAR1*NVAR2+(I-1)*NVAR1+1
C       L2=(IB-1)*NVAR1*NVAR2+I*NVAR1
C  66   WRITE(6,7)(BETA(L),L=L1,L2)
C 666   CONTINUE
C  7    FORMAT(' BETA'/(5F15.4/))
C       DO 81 IB=1,IBOOT+2
C       J1=(IB-1)*NCOMP+1
C       J2=IB*NCOMP
C       WRITE(6,82)(PRESS(J),J=J1,J2)
C  82   FORMAT(/' PRESS: '/(5F15.4/))
C  81   CONTINUE
C       DO 86 IB=1,IBOOT+2
C       J1=(IB-1)*NCOMP+1
C       J2=IB*NCOMP
C       WRITE(6,87)(CR2(J),J=J1,J2)
C  87   FORMAT(/' CR2: '/(5F15.4/))
C  86   CONTINUE
C       WRITE(6,84)(SS(IB),IB=1,IBOOT+2)
C  84   FORMAT(/' SUM OF SQUARED RESIDUALS:'/(5F15.4/))
CC      WRITE(6,85)(R2(IB),IB=1,IBOOT+2)
C  85   FORMAT(/'R2:'/(5F15.4/))
C       WRITE(6,83)(NOPT(IB),IB=1,IBOOT+2)
C  83   FORMAT(/' OPTIMAL COMP:'/10I5)
C       WRITE(6,16)
C  16   FORMAT(//' SAMPLE       ACTUAL       PREDICTED      DIFFERENCE'/)
C       DO 10 I=1,NPAT
```

```
C      L1=(I-1)*NVAR2+1
C      L2=I*NVAR2
C 10   WRITE(6,11) I,(Y(L),YPRED(L),RES(L),L=L1,L2)
C 11   FORMAT(I5,3F15.4/(5X,3F15.4))
C   PLOT Y VS. YPRED
C      DO 100 I=1,NPAT
C      L=(I-1)*NVAR2+1
C      XXX(I)=Y(L)
C      YYY(I)=YPRED(L)
C 100  CONTINUE
C      CALL PRINT(XXX,YYY,X1,NPAT)
C   PLOT Y VS. RESIDUAL
C      DO 101 I=1,NPAT
C      L=(I-1)*NVAR2+1
C      XXX(I)=Y(L)
C      YYY(I)=RES(L)
C 101  CONTINUE
C      CALL PRINT(XXX,YYY,X1,NPAT)
C      STOP
C      END
C  INPUT:
C      NPAT        # OF SAMPLES
C      NVAR1       # OF VARIABLES IN THE FIRST BLOCK
C      NVAR2       # OF VARIABLES IN THE SECOND BLOCK
C      NCOMP       MAXIMUM # OF LATENT COMPONENTS    DEFAULT=NVAR1
C                  AS OUTPUT: OPTIMAL NUMBER OF COMPONENTS
C      NITMAX      MAXIMUM # OF ITERATION     DEFAULT=100
C      EPS         CONVERGENCE CRITERIUM      DEFAULT=0.0001
C      IBOOT       BOOTSTRAP FLAG    0 - NO BOOTSTRAP   (DEFAULT)
C                                    GT 1 - BOOTSTRAP
C      ICROS       CROSSVALIDATION FLAG    0 - NO CROSSVALIDATION
C                                    GT 1 - CROSSVALIDATION
(DEFAULT)
C      ICENT       CENTERING FALG      0 - FORCED TO GO THROUGH
THE ORIGIN
C                                    GT 1 - OFFSET IS CALCULATED
(DEFAULT)
C      X(NVAR1,NPAT)   FIRST BLOCK
C      Y(NVAR2,NPAT)   SECOND BLOCK
C      WEYT(NPAT)      WEIGHTS
C      WEYTB(NPAT)     BOOTSTRAP SAMPLE WEIGHTS
C  OUTPUT:
C      XBAR(NVAR1+NVAR2)   MEAN OF X AND Y
C      OFF(NVAR2,MAX(IBOOT+2,ICROS))  OFFSETS
C      BETA(NVAR1,NVAR2,MAX(IBOOT+2,ICROS))   REGRESSION MATRIX
C      W1(NVAR1,NCOMP)    WEIGHTS OF FIRST BLOCK
C      W2(NVAR2,NCOMP)    WEIGHTS OF SECOND BLOCK
C      B(NVAR1,NCOMP)  LOADINGS
C      U(NPAT,NCOMP)   LATENT VARIABLES OF FIRST BLOCK
C      V(NPAT,NCOMP)   LATENT VARIABLES OF SECOND BLOCK
C      RO(NCOMP)    INNER REALATIONSHIP COEFF
C      SS(IBOOT+2)   SUM OF SQUARED RESIDUALS
C      R2(IBOOT+2)   R SQUARE
C      PRESS(NCOMP,IBOOT+2)   CROSSVALIDATED SUM OF SQUARED
C         RESIDUALS
C      CR2(NCOMP,IBOOT+2) CROSSVALIDATED R SQUARE
C      NOPT(IBOOT+2)   OPTIMAL NUMBER OF COMPONENTS
C      YPRED(NVAR2,NPAT)   PREDICTED Y-S
C      RES(NVAR2+1,NPAT)   RESIDUALS, LAST ROW IS THE
THEORETICAL
C          QUANTILES
C      IERR      ERROR FLAG
```

```
C          0 - NO ERROR
C          1 - SUM OF WEIGHTS IS ZERO
C          2 - SUM OF SQUARES IS ZERO
C   SCRATCH:
C          SCRTCH(NPAT*(NVAR1+NVAR2+1)+MAX(NPAT,NVAR1*(NVAR1+1)))
C             SCRTCH   VECTOR
C       IX(NPAT)       INTEGER SCRATCH VECTOR
        SUBROUTINE PLSJER(NPAT,NVAR1,NVAR2,NCOMP,NITMAX,EPS,IBOOT,ICROS,
       *ICENT,X,Y,WEYT,WEYTB,XBAR,XSCAL,OFF,BETA,VARNC,W1,W2,B,U,V,RO,SS,
       *R2,PRESS,CR2,NOPT,YPRED,RES,SSS,SSY,IERR,SCRTCH,IX)
C
C       MAIN of PLS Implementation
C
        REAL*8 X(NVAR1,NPAT),Y(NVAR2,NPAT),WEYT(1),BETA(NVAR1,NVAR2,1),
       *SCRTCH(1),W1(NVAR1,NCOMP),W2(NVAR2,NCOMP),B(NVAR1,NCOMP),WEYTB(1),
       *U(NPAT,NCOMP),V(NPAT,NCOMP),RO(1),XBAR(1),EPS,SS(NVAR2,IBOOT+2),
       *OFF(NVAR2,1),CR2(NVAR2,NCOMP,1),PRESS(NVAR2+1,NCOMP,1),YPRED(NVAR
       *2,NPAT),RES(NVAR2+1,NPAT),XNPAT,SSS(1),PMIN,RAT,S,R2(NVAR2,IBOOT+
       *2),SSY(1),ATL,XNPATT,XSCAL(1),VARNC(NVAR2,NCOMP),SUM
        INTEGER*4 IX(1),NPAT,NVAR1,NVAR2,NCOMP,NITMAX,IERR,ICOMP,NOPT(1),
       *ICROS,IBOOT,ICENT,ICROS1,IBOOT1,IC,NN,IB,L,I,IOUT,IEX,J,JJ,KL
        integer*4 novariance    ! flag for zero variance
        real*8 varmax           ! flag for max variance
        IERR=0
        ICROS1=0
        IBOOT1=0
        RAT=FLOAT(NPAT)/float(NPAT-1)
        NN=NPAT*(NVAR1+NVAR2+1)+1
C   calculate quantiles for the q-q plot
        call qq(npat,weyt,scrtch,ierr)
        if(ierr.ne.0) return
        do 50 i=1,npat
   50   res(nvar2+1,i)=scrtch(i)
C   set flags for no cross-validation and no bootstrap
        IF(ICROS.EQ.0) THEN
        ICROS=1
        ICROS1=1
        END IF
        IF(IBOOT.EQ.0) THEN
        IBOOT=1
        IBOOT1=1
        END IF
C   bootstrap loop
        DO 100 IB=1,IBOOT
        DO 21 ICOMP=1,NCOMP
        DO 21 J=1,NVAR2+1
   21   PRESS(J,ICOMP,IB)=0.
C   no bootstrap, copy the weights
        IF(IBOOT1.EQ.1) THEN
        CALL NOBOOTP(WEYTB,WEYT,NPAT)
        GOTO 10
        END IF
C   draw a bootstrap sample , new weights in weytb
        CALL RANDOMP(WEYTB,WEYT,IX,NPAT)
   10   CONTINUE
C   set up an auxiliary vector for cross-validation pointing
C to non zero c
C       weight
        IF(ICROS1.NE.1) THEN
        KL=0
        DO 30 I=1,NPAT
        IF(WEYTB(I).LE.0.) GOTO 30
```

```
      KL=KL+1
      IX(KL)=I
30    CONTINUE
      CALL RANUMS(SCRTCH,KL)
      CALL SORT(SCRTCH,IX,1,KL)
      DO 32 I=1,NPAT
32    SCRTCH(I)=0.
c     calculate how many samples to delete
      IOUT=KL/ICROS
      IEX=MOD(KL,ICROS)
      END IF
c     calculate sum of squares
      DO 40 J = 1,NVAR2
      SSY(J) = 0.
      ATL = 0.
      XNPATT = 0.
      DO 41 I = 1,NPAT
      XNPATT = XNPATT + WEYTB(I)
41    ATL = ATL + Y(J,I)*WEYTB(I)
      ATL = ATL / XNPATT
      DO 40 I = 1,NPAT
40    SSY(J) = SSY(J) + (Y(J,I) - ATL)**2 * WEYTB(I)
c     cross-validation loop
      DO 200 IC=1,ICROS
      IF(ICROS1.EQ.1) THEN
c     no cross-validation, copy the weights
      CALL NOBOOTP(SCRTCH,WEYTB,NPAT)
      GOTO 20
      END IF
c     set weights for cross-validation in scrtch
      CALL CROSSP(SCRTCH,WEYTB,IX,KL,IOUT,IEX,IC)
20    CONTINUE
      IF(SCRTCH(I).GT.0.) S=S+(Y(J,I)-XBAR(JJ))**2*SCRTCH(I)
666   CONTINUE
      XSCAL(JJ)=DSQRT(S/(XNPAT-1))

if (xscal(j).eq.0) then
      IERR = 2
      RETURN
      END IF
66    continue
      END IF
C     ICENT = 1 NO CENTERING OR SCALING
      IF(ICENT.EQ.1) THEN
      DO 788 I=1,NPAT
      DO 789 J=1,NVAR1
      L=(I-1)*NVAR1+J+NPAT
789   SCRTCH(L) = X(J,I)
      DO 790 J=1,NVAR2
      L=NPAT+NPAT*NVAR1+(I-1)*NVAR2+J
790   SCRTCH(L) = Y(J,I)
788   CONTINUE
      DO 791 J=1,NVAR1+NVAR2
      XBAR(J) = 0.
791   XSCAL(J) = 1.
      END IF
C     ICENT = 2
      IF(ICENT.EQ.2) THEN
      DO 5 I=1,NPAT
      DO 6 J=1,NVAR1
      L=(I-1)*NVAR1+J+NPAT
      SCRTCH(L)=X(J,I)-XBAR(J)
```

```
      6 CONTINUE
        DO 7 J=1,NVAR2
        JJ=J+NVAR1
        L=NPAT+NPAT*NVAR1+(I-1)*NVAR2+J
        SCRTCH(L)=Y(J,I)-XBAR(JJ)
      7 CONTINUE
      5 CONTINUE
        DO 792 J=1,NVAR1+NVAR2
    792 XSCAL(J) = 1.
        END IF
C   ICENT = 3
        IF(ICENT.EQ.3) THEN
        DO 793 I=1,NPAT
        DO 794 J=1,NVAR1
        L=(I-1)*NVAR1+J+NPAT
        SCRTCH(L)=(X(J,I)-XBAR(J))/XSCAL(J)
    794 CONTINUE
        DO 795 J=1,NVAR2
        JJ=J+NVAR1
        L=NPAT+NPAT*NVAR1+(I-1)*NVAR2+J
        SCRTCH(L)=(Y(J,I)-XBAR(JJ))/XSCAL(JJ)
    795 CONTINUE
    793 CONTINUE
        END IF
C   ICENT = 4
        IF(ICENT.EQ.4) THEN
        DO 796 I=1,NPAT
        DO 797 J=1,NVAR1
C   SUM OF WEIGHTS
        XNPAT=0.
        DO 1 I=1,NPAT
        IF(SCRTCH(I).GT.0.) XNPAT=XNPAT+SCRTCH(I)
      1 CONTINUE
        IF(XNPAT.LE.0.) THEN
        IERR=2
        RETURN
        END IF
C   MEAN VALUES AND SCALE, depending on ICENT. If
C   1 - X;   2 - X-XBAR;   3 - (X-XBAR)/XSCAL;    4 - X/XSCAL;
C   CALCULATE XBAR THE MEAN
        IF(ICENT.GT.1) THEN
        DO 33 J=1,NVAR1
        S=0.
        DO 3 I=1,NPAT
        IF(SCRTCH(I).GT.0.) S=S+X(J,I)*SCRTCH(I)
      3 CONTINUE
     33 XBAR(J)=S/XNPAT
        DO 4 J=1,NVAR2
        S=0.
        DO 44 I=1,NPAT
        IF(SCRTCH(I).GT.0.) S=S+Y(J,I)*SCRTCH(I)
     44 CONTINUE
        JJ=J+NVAR1
      4 XBAR(JJ)=S/XNPAT
        END IF
C   CALCULATE XSCAL THE VARIANCE
        IF(ICENT.GE.3) THEN
        novariance = 0
        DO 55 J=1,NVAR1
        S=0.
        DO 555 I=1,NPAT
        IF(SCRTCH(I).GT.0.) S=S+(X(J,I)-XBAR(J))**2*SCRTCH(I)
```

```
555 CONTINUE
    XSCAL(J)=DSQRT(S/(XNPAT-1))
    IF(S.le.0.) novariance=novariance+1
 55 continue
    if (novariance.NE.0) then
    varmax=1.e20
    do 7701 j=1,NVAR1
     if (xscal(j).gt. 0.0  .AND. xscal(j).lt.varmax) varmax=xscal(j)
7701 continue
    if (varmax.eq.1.e20) then
    IERR = 2
    RETURN
    END IF
    varmax=varmax/1000.
    do 556 j = 1,NVAR1
     if (xscal(j).le.0.0) then
       xscal(j) = varmax
       endif
556 continue
    endif
    DO 66 J=1,NVAR2
    JJ=J+NVAR1
    S=0.
    DO 666 I=1,NPAT
    L=(I-1)*NVAR1+J+NPAT
    SCRTCH(L)=X(J,I)/XSCAL(J)
797 CONTINUE
    DO 798 J=1,NVAR2
    JJ=J+NVAR1
    L=NPAT+NPAT*NVAR1+(I-1)*NVAR2+J
    SCRTCH(L)=Y(J,I)/XSCAL(JJ)
798 CONTINUE
796 CONTINUE
    DO 799 J=1,NVAR1+NVAR2
799 XBAR(J) = 0.
    END IF
C   CALCULATE MODEL OF NCOMP COMPONENTS
    DO 2 ICOMP=1,NCOMP
    CALL PCPLS(NVAR1,NVAR2,NPAT,NCOMP,ICOMP,NITMAX,EPS,
   *SCRTCH(NPAT+1),SCRTCH(NPAT*(NVAR1+1)+1),SCRTCH,W1,W2,B,RO,U,V,
   *SCRTCH(NN),IERR)
    IF(IERR.NE.0) THEN
    NCOMP = ICOMP-1
    IF(NCOMP.LE.0) RETURN
    IERR = 0
    CALL DAB$WRI4_INT('No more than @ components can be calculated',
   *ncomp,4)
    IQUIT = 0
    CALL DAB$WRI4_LN(IQUIT)
    GOTO 222
    END IF
    DO 23 J = 1,NVAR2
    SUM = 0.
    JJ = J + NVAR1
    DO 22 I = 1, NPAT
    L = NPAT + NPAT*NVAR1 + (I-1)*NVAR2 + J
 22 SUM = SUM + SCRTCH(L)**2 * SCRTCH(I)
    IF(ICENT.GE.3) SUM = SUM * XSCAL(JJ)**2
 23 VARNC(J,ICOMP) = 1. - SUM / SSY(J)
  2 CONTINUE
222 CONTINUE
```

```
c     load the data again for residual calculation
      DO 9 I=1,NPAT
      DO 15 J=1,NVAR1
      L=(I-1)*NVAR1+J+NPAT
   15 SCRTCH(L)=X(J,I)
      DO 11 J=1,NVAR2
      L=(I-1)*NVAR2+J+NPAT*(NVAR1+1)
   11 SCRTCH(L)=Y(J,I)
    9 CONTINUE
      IF(ICROS1.EQ.1) THEN
c     samples with negative weights are predicted, so set all of
them to -
      DO 13 I=1,NPAT
   13 SCRTCH(I)=-SCRTCH(I)
      END IF
C     REGRESSION MATRIX AND PREDICTION
      DO 8 ICOMP=1,NCOMP
      IF(IBOOT1.NE.1) THEN
      CALL MATRIX(NVAR1,NVAR2,NCOMP,ICOMP,BETA(1,1,IB),
     *W1,W2,B,RO,SCRTCH(NN))
      CALL RESID(NPAT,NVAR1,NVAR2,SCRTCH(NPAT+1),SCRTCH(NPAT*(NVAR
     *1+1)+1),SCRTCH,XBAR,XSCAL,OFF(1,IB),BETA(1,1,IB),RES,YPRED,SSS,
     *IERR)
      ELSE
      CALL MATRIX(NVAR1,NVAR2,NCOMP,ICOMP,BETA(1,1,IC),
     *W1,W2,B,RO,SCRTCH(NN))
      CALL RESID(NPAT,NVAR1,NVAR2,SCRTCH(NPAT+1),SCRTCH(NPAT*(NVAR
     *1+1)+1),SCRTCH,XBAR,XSCAL,OFF(1,IC),BETA(1,1,IC),RES,YPRED,SSS,
     *IERR)
      END IF
      IF(IERR.NE.0) RETURN
      IF(ICROS1.EQ.0) THEN
c     sum of cross-validated squared residuals
      DO 88 J = 1,NVAR2
   88 PRESS(J,ICOMP,IB)=PRESS(J,ICOMP,IB)+SSS(J)
      END IF
    8 CONTINUE
      IF(ICROS1.EQ.1) THEN
c     sum of squared residuals and r squared
      DO 89 J = 1,NVAR2
      SS(J,IB)=SSS(J)
   89 R2(J,IB)=1.-SS(J,IB)/SSY(J)
      DO 90 J = 1,NVAR2
   90 SS(J,IB) = SS(J,IB)/XNPATT
      END IF
  200 CONTINUE
c     find the optimal number of components
      IF(ICROS1.NE.1) THEN
      PMIN=1.D10
      DO 12 ICOMP=1,NCOMP
      S = 0.
      DO 123 J = 1,NVAR2
  123 S = S + PRESS(J,ICOMP,IB)
      PRESS(NVAR2+1,ICOMP,IB) = S/NVAR2
      IF (PRESS(NVAR2+1,ICOMP,IB).LT.PMIN) THEN
      PMIN=PRESS(NVAR2+1,ICOMP,IB)
      NOPT(IB)=ICOMP
      END IF
   12 CONTINUE
      END IF
```

```
C CROSS-VALIDATED R SQUARED
      IF(ICROS1.NE.1) THEN
      DO 122 ICOMP=1,NCOMP
      DO 122 J = 1,NVAR2
  122 CR2(J,ICOMP,IB)=1.-PRESS(J,ICOMP,IB)/(RAT*SSY(J))
      DO 124 J = 1,NVAR2+1
      DO 124 ICOMP = 1,NCOMP
  124 PRESS(J,ICOMP,IB) = PRESS(J,ICOMP,IB)/XNPATT
      END IF
  100 CONTINUE
      IF(IBOOT1.EQ.1) IBOOT=0
      IF(ICROS1.EQ.1) ICROS=0
c    calculate the mean and the variance of the bootstrapped
quantities
      IF(IBOOT1.EQ.1) goto 7734
      CALL BOOTPLS(SS,R2,PRESS,CR2,OFF,BETA,NOPT,NCOMP,IBOOT,NVAR2,
     *NVAR1)
 7734 call see(ss,press,(iboot+2)*nvar2,(nvar2+1)*ncomp*(iboot+2),
     1          npat,ncomp) !SEE (sqrt)

RETURN
      END

SUBROUTINE BOOTPLS(SS,R2,PRESS,CR2,OFF,BETA,NOPT,NCOMP,IBOOT,
     *NVAR2,NVAR1)
C
C       MEAN AND AVERAGE OF THE BOOTSTRAPED QUANTITIES
C
      REAL*8 SS(NVAR2,1),R2(NVAR2,1),CR2(NVAR2,NCOMP,1),PRESS(NVAR2+1,
     *NCOMP,1),OFF(NVAR2,1),BETA(NVAR1,NVAR2,1)
      INTEGER*4 NOPT(1),NCOMP,IBOOT,NVAR2,NVAR1
C   ZERO THE STORAGES
      DO 9 J = 1,NVAR2
      SS(J,IBOOT+1)=0.
      R2(J,IBOOT+1)=0.
      SS(J,IBOOT+2)=0.
      R2(J,IBOOT+2)=0.
      DO 10 K=1,NCOMP
      PRESS(J,K,IBOOT+1)=0.
      PRESS(J,K,IBOOT+2)=0.
      CR2(J,K,IBOOT+2)=0.
   10 CR2(J,K,IBOOT+1)=0.
    9 CONTINUE
      NOPT(IBOOT+1)=0
      NOPT(IBOOT+2)=0.
      DO 20 J=1,NVAR2
      OFF(J,IBOOT+1)=0.
      DO 20 I=1,NVAR1
   20 BETA(I,J,IBOOT+1)=0.
      DO 21 J=1,NVAR2
      OFF(J,IBOOT+2)=0.
      DO 21 I=1,NVAR1
   21 BETA(I,J,IBOOT+2)=0.
C   SUM THE ELEMENTS OF ALL VECTORS INTO THE IBOOT+1-TH
ELEMENTS
      DO 1 IB=1,IBOOT
      DO 11 K = 1,NVAR2
      SS(K,IBOOT+1)=SS(K,IBOOT+1)+SS(K,IB)
      R2(K,IBOOT+1)=R2(K,IBOOT+1)+R2(K,IB)
      DO 30 J=1,NCOMP
      CR2(K,J,IBOOT+1)=CR2(K,J,IBOOT+1)+CR2(K,J,IB)
```

```
   30 PRESS(K,J,IBOOT+1)=PRESS(K,J,IBOOT+1)+PRESS(K,J,IB)
   11 CONTINUE
      NOPT(IBOOT+1)=NOPT(IBOOT+1)+NOPT(IB)
      DO 40 J=1,NVAR2
      OFF(J,IBOOT+1)=OFF(J,IBOOT+1)+OFF(J,IB)
      DO 40 I=1,NVAR1
   40 BETA(I,J,IBOOT+1)=BETA(I,J,IBOOT+1)+BETA(I,J,IB)
    1 CONTINUE
C    CALCULATE AVERAGE
      DO 12 K = 1,NVAR2
      SS(K,IBOOT+1)=SS(K,IBOOT+1)/IBOOT
      R2(K,IBOOT+1)=R2(K,IBOOT+1)/IBOOT
      DO 50 J=1,NCOMP
      PRESS(K,J,IBOOT+1)=PRESS(K,J,IBOOT+1)/IBOOT
   50 CR2(K,J,IBOOT+1)=CR2(K,J,IBOOT+1)/IBOOT
   12 CONTINUE
      NOPT(IBOOT+1)=NOPT(IBOOT+1)/IBOOT
      DO 60 J=1,NVAR2
      OFF(J,IBOOT+1)=OFF(J,IBOOT+1)/IBOOT
      DO 60 I=1,NVAR1
   60 BETA(I,J,IBOOT+1)=BETA(I,J,IBOOT+1)/IBOOT
C    SUM THE SQUARED DEVIATION FROM THE AVERAGES IN THE
     IBOOT+2-TH  C   ELEMENT
      DO 2 IB=1,IBOOT
      DO 22 K = 1,NVAR2
      SS(K,IBOOT+2)=SS(K,IBOOT+2)+(SS(K,IB)-SS(K,IBOOT+1))**2
      R2(K,IBOOT+2)=R2(K,IBOOT+2)+(R2(K,IB)-R2(K,IBOOT+1))**2
      DO 31 J=1,NCOMP
      CR2(K,J,IBOOT+2)=CR2(K,J,IBOOT+2)+(CR2(K,J,IB)-CR2(K,J,IBOOT+1))
     ***2
   31 PRESS(K,J,IBOOT+2)=PRESS(K,J,IBOOT+2)+(PRESS(K,J,IB)-PRESS(K,J,
     *IBOOT+1))**2
   22 CONTINUE
      NOPT(IBOOT+2)=NOPT(IBOOT+2)+(NOPT(IB)-NOPT(IBOOT+1))**2
      DO 41 J=1,NVAR2
      OFF(J,IBOOT+2)=OFF(J,IBOOT+2)+(OFF(J,IB)-OFF(J,IBOOT+1))**2
      DO 41 I=1,NVAR1
   41 BETA(I,J,IBOOT+2)=BETA(I,J,IBOOT+2)+(BETA(I,J,IB)-BETA(I,J,IBOOT+1
     *))**2
    2 CONTINUE
C    CALCULATE VARIANCE
      DO 52 K = 1,NVAR2
      SS(K,IBOOT+2)=dsqrt( SS(K,IBOOT+2)/IBOOT )        !DEP sqrted them
      R2(K,IBOOT+2)=dsqrt( R2(K,IBOOT+2)/IBOOT )
      DO 51 J=1,NCOMP
      PRESS(K,J,IBOOT+2)=dsqrt( PRESS(K,J,IBOOT+2)/IBOOT )
   51 CR2(K,J,IBOOT+2)   =dsqrt( CR2(K,J,IBOOT+2)/IBOOT )
   52 CONTINUE
      NOPT(IBOOT+2)= int( sqrt( float(NOPT(IBOOT+2))/IBOOT ) )
      DO 61 J=1,NVAR2
      OFF(J,IBOOT+2)=dsqrt( OFF(J,IBOOT+2)/IBOOT )
      DO 61 I=1,NVAR1
   61 BETA(I,J,IBOOT+2)=dsqrt( BETA(I,J,IBOOT+2)/IBOOT )
      RETURN
      END SUBROUTINE PCPLS(NVAR1,NVAR2,NPAT,NCOMP,ICOMP,NITMAX,
     *EPS,X,Y,WEYT,W1,W2,B,RO,U,V,VT,IERR)
C    THE PLS CORE -
C        CALCULATES THE ICOMP-TH PLS COMPONENT
```

```
C
      REAL*8 X(NVAR1,NPAT),Y(NVAR2,NPAT),WEYT(1),SUMU,
     *W1(NVAR1,NCOMP),W2(NVAR2,NCOMP),B(NVAR1,NCOMP),
     *U(NPAT,NCOMP),V(NPAT,NCOMP),RO(1),EPS,SS,VT(1)
      INTEGER*4 NPAT,NVAR1,NVAR2,NCOMP,NITMAX,IERR,ICOMP
      IERR=0
C
C     Initialize V
C
      DO 12 I=1,NPAT
   12 V(I,ICOMP)=Y(1,I)
      ITER=0
  100 CONTINUE
      ITER=ITER+1
C
C     Weights of first block
C
      DO 1 J=1,NVAR1
      SS=0.
      DO 3 I=1,NPAT
      IF(WEYT(I).LE.0.) GOTO 3
      SS=SS+X(J,I)*V(I,ICOMP)*WEYT(I)
    3 CONTINUE
    1 W1(J,ICOMP)=SS
      SS=0.
      DO 4 K=1,NVAR1
    4 SS=SS+W1(K,ICOMP)**2
      IF(SS.LE.0.) THEN
      IERR=-1
      RETURN
      END IF
      SS=DSQRT(SS)
      DO 5 K=1,NVAR1
    5 W1(K,ICOMP)=W1(K,ICOMP)/SS
C
C     Latent variable of first block
C
      DO 6 I=1,NPAT
      IF(WEYT(I).LE.0.) GOTO 6
      SS=0.
      DO 7 K=1,NVAR1
    7 SS=SS+X(K,I)*W1(K,ICOMP)
      U(I,ICOMP)=SS
    6 CONTINUE
C
C     Normalization of U
C
      SUMU=0.
      DO 88 I=1,NPAT
      IF(WEYT(I).LE.0.) GOTO 88
      SUMU=SUMU+U(I,ICOMP)**2*WEYT(I)
   88 CONTINUE
C
C     Weights of second block
C
      DO 11 J=1,NVAR2
      SS=0.
      DO 2 I=1,NPAT
      IF(WEYT(I).LE.0.) GOTO 2
      SS=SS+Y(J,I)*U(I,ICOMP)*WEYT(I)
    2 CONTINUE
```

```
   11 W2(J,ICOMP)=SS
      SS=0.
      DO 44 K=1,NVAR2
   44 SS=SS+W2(K,ICOMP)**2
      IF(SS.LE.0.) THEN
      IERR=-2
      RETURN
      END IF
      SS=DSQRT(SS)
      DO 55 K=1,NVAR2
   55 W2(K,ICOMP)=W2(K,ICOMP)/SS
C
C        Latent variable of second block
C
      DO 66 I=1,NPAT
      IF(WEYT(I).LE.0.) GOTO 66
      SS=0.
      DO 77 K=1,NVAR2
   77 SS=SS+Y(K,I)*W2(K,ICOMP)
      VT(I)=SS
   66 CONTINUE
C
C        convergence check
C
      SS=0.
      DO 67 I=1,NPAT
      IF(WEYT(I).LE.0.) GOTO 67
      SS=SS+(VT(I)-V(I,ICOMP))**2
   67 CONTINUE
      DO 68 I=1,NPAT
   68 V(I,ICOMP)=VT(I)
      IF(SS.GT.EPS.AND.ITER.LT.NITMAX) GOTO 100
C
C        Inner relationship
C
      IF(SUMU.LE.0.) THEN
      IERR=-3
      RETURN
      END IF
      SS=0.
      DO 30 I=1,NPAT
      IF(WEYT(I).LE.0.) GOTO 30
      SS=SS+U(I,ICOMP)*V(I,ICOMP)*WEYT(I)
   30 CONTINUE
      RO(ICOMP)=SS/SUMU
C
C        Normalization of the model vector
C
      SUMU=0.
      DO 188 I=1,NPAT
      IF(WEYT(I).LE.0.) GOTO 188
      SUMU=SUMU+(U(I,ICOMP)*RO(ICOMP))**2*WEYT(I)
  188 CONTINUE
C
C        Loadings
C
      IF(SUMU.LE.0.) THEN
      IERR=-4
      RETURN
      END IF
      DO 21 J=1,NVAR1
      SS=0.
```

```
      DO 19 I=1,NPAT
      IF(WEYT(I).LE.0.) GOTO 19
      SS=SS+X(J,I)*U(I,ICOMP)*RO(ICOMP)*WEYT(I)/SUMU
   19 CONTINUE
      B(J,ICOMP)=SS
   21 CONTINUE
C
C     Residuals
C
      DO 22 I=1,NPAT
      IF (WEYT(I).LE.0.) GOTO 22
      SS=RO(ICOMP)*U(I,ICOMP)
      DO 24 J=1,NVAR1
      X(J,I)=X(J,I)-B(J,ICOMP)*SS
   24 CONTINUE
      DO 25 J=1,NVAR2
      Y(J,I)=Y(J,I)-W2(J,ICOMP)*SS
   25 CONTINUE
   22 CONTINUE
      RETURN
      END SUBROUTINE NOBOOTP(X,Y,NPAT)
C
C     COPY WEIGHT VECTOR
C
      REAL*8 X(1),Y(1)
      INTEGER*4 NPAT
      DO 1 I=1,NPAT
    1 X(I)=Y(I)
      RETURN
      END SUBROUTINE RANDOMP(X,Y,IX,NPAT)
C
C     RANDOM NUMBER GENERATOR FOR DRAWING BOOTSTRAP SAMPLE
C
      REAL*8 X(1),Y(1)
      INTEGER*4 IX(1),NPAT
      CALL RANUMS(X,NPAT)
      DO 1 I=1,NPAT
    1 IX(I)=NPAT*X(I)+1
      DO 2 I=1,NPAT
    2 X(I)=0.
      DO 3 I=1,NPAT
      II=IX(I)
    3 X(II)=X(II)+Y(II)
      RETURN
      END SUBROUTINE CROSSP(X,Y,IX,NPAT,IOUT,IEX,IC)
C
C     SET WEIGHTS FOR CROSS-VALIDATION
C
      REAL*8 X(1),Y(1)
      INTEGER*4 IOUT,IC,NPAT,IEX,IX(1),I1,I2,i
      I1=(IC-1)*IOUT+MIN(IEX,IC-1)+1
      I2=IC*IOUT+MIN(IEX,IC)
      DO 1 I=1,NPAT
```

```
      ii=ix(i)
      X(ii)=Y(ii)
      IF(I.GE.I1.AND.I.LE.I2) X(ii)=-X(ii)

1     CONTINUE
      RETURN
      END
```

/* MAP.C */

```c
/* MAP.C does all processing of the numerical data produced
by the various other CoMFA operations into forms which allow
their visualization on a variety of standard display systems.
Has three main entry points, q3$map_contour (makes contour
maps), q3$map_display (makes scatter plots), and q3$map_list
(prints the numerical values). */ if vax11c
module map "V1.0"
endif include stdio
include "dab$source:dabdef.c"
# include "q3d$source:q3def.c"
# include "sys$runsource:vmsstrdef.h"

define MISSING -1.0e14 double fabs();

/* numerical codes for colors */
static int colorcode[] = {1 /* purple */, 2 /*blue */, 3 /* cyan */,
    4 /*green*/, 5 /* yellow */, 6 /* orange */, 7 /* red */};

void q3$map_contour (source, field_type)
/* MAIN SUBROUTINE =========================================== */
/* when invoked by user, displays, as contoured display, any
of several different CoMFA displays of field data as a
function of spatial coordinates, especially (by default) the
contour map of the QSAR coefficients times the standard
deviation of the corresponding column values */ short
    *source, /* 1 = individual molecule, 2 = overall QSAR */
    *field_type /* 1 = steric 2 = electrostatic, 3 = both (as
separate images) */
{
  struct q3mol *m, *q3$mol_select();
  struct q3conf *cf, *q3$cnf_select();
  int ie, nr, i, offset, results, nx, *xcols, c1 = 1, c19 = 19, ny,
      c16 = 16, c17 = 17, vtype;
  double val, *coords, *coeff;
  struct q3region *r, *q3$reg_select();
  struct ana_header *a;

if (!Q3D) {dab$dut_sho_err ("No plan"); return;}
  coords = 0;

/* get the values corresponding to the lattice points, either
... */
  switch (*source) {
```

```
/*    ... from a single molecule selected by the user */
case 1: if (!(m = q3$mol_select (&nr))) return;
        if (!(cf = q3$cnf_select (m, &nr))) return;
        if (!cf -> encoords) {
           dab$dut_sho_err ("No energy map for the conformer");
           .return;
           }
        if (!dab$mat_spdbl (&coords, cf -> encoords, ""))) return;
        ie = cf -> encoords / 2;
            /* use MISSING for sterically excluded regions */
        for (i = 0; i < cf -> encoords; i++)
            coords [i] = ((i < ie && cf -> emap [i] == fabs(Q3D ->
too_big) ) ||
            (i >= ie && !cf -> emap)) ? MISSING : cf -> emap [i];
        offset = 0;
        break;
case 2:    /* ... or from the QSAR */
    if (!(coords = q3$map_receptor (&ie, &vtype))) return;
        offset = 0;
        break;
        }

/* get starting point for this region coords - nr has ID of
selected region - must skip both static and Coulombic fields
of any preceding regions */ if (!(r = q3$reg_select (&nr))) goto free;
    for (i = 0; i < nr - 1; i++) offset += 2 * q3$eva_npts (Q3D ->
reg_ptr + i);

/* write out the data selected for contouring; increment
offset if energy field is electrostatic */
    switch (*field_type) {
case 1: q3$map_wrcnt (*field_type, *source, &(coords [offset]), r);
break;
case 2: offset += q3$eva_npts (r);
        q3$map_wrcnt (*field_type, *source, &(coords [offset]), r);
        break;
case 3: q3$map_wrcnt (1, *source, &(coords [offset]), r);
        offset += q3$eva_npts (r);
        q3$map_wrcnt (2, *source, &(coords [offset]), r);
        break;
        }
free:
    if (coords) UTL_MEM_FREE (coords);
    return;
} static q3$map_wrcnt (ftype, source, coords, r)
/* SUBROUTINE ================================================ ===== */
/* actually writes the coords to  a file for contouring */
int ftype, source;
double *coords;
struct q3region *r;
{
    FILE *fp;
    double mean, val, max, min, ssq, cssq, sq;
    float hicl, locl;
    short warea;
    int i, nr, nv, ncoords, workarea;
    static char *ftn[] = {"Steric", "Electrostatic"};
    char fname[100];
```

```
    VMS_String UTL$VMSSTR_CARVE(), vmsname;

ncoords = q3$eva_npts (r);
    max = min = coords [0];
    for (i = 0; i < ncoords; i++) if (coords [i] != D_MISSING) {
        if (coords [i] > max) max = coords [i];
        if (coords [i] < min) min = coords [i];
        } sprintf (msg, "File name for %s contour input data ('.cnt')",
        ftn [ftype - 1]);
    if (!dab$usr_getstring (msg, fname)) return;
    if (!(fp = fopen (fname, "w"))) {
        sprintf (msg, "Could not open '%s'", fname);
        dab$dut_sho_err (msg);
        return;
        }
    val = 1.0;
    for (nr = 0; nr < 3; nr++) if (!q3$map_wriflo (fp, val)) goto err;
    val = 90.0;
    for (nr = 0; nr < 3; nr++) if (!q3$map_wriflo (fp, val)) goto err;
    for (nr = 0; nr < 3; nr++)
        if (!q3$map_wriflo (fp, r -> step_size[nr])) goto err;
    for (nr = 0; nr < 3; nr++)
        if (!q3$map_wriflo (fp, r -> lo_coords[nr])) goto err;
    for (nr = 0; nr < 3; nr++)
        if (!q3$map_wriflo (fp, r -> lo_coords [nr] +
            (r -> nsteps [nr] - 1) * r -> step_size [nr])) goto err;
    if (!q3$map_wriflo (fp, min)) goto err;
    if (!q3$map_wriflo (fp, max)) goto err;
    for (nr = 0; nr < ncoords; nr++) if (!q3$map_wriflo (fp, coords
[nr])) goto err;
    fclose (fp);
    if (!dab$usr_ynans ("See contour map now", TRUE, TRUE, &nr) || !nr)
return;
    if (!dab$usr_getcase ("work_area", &workarea))
            return (FALSE);
    warea = (short) workarea;
    hicl = (float) max; locl = (float) min;
    edit (&warea);
    vmsname = UTL$VMSSTR_CARVE (fname);
    q3user_contour (vmsname, &hicl, &locl);

/* write the mean & variance of values enclosed by contour
lines */
    mean = ssq = cssq = 0.0;
    for (nr = nv = 0 ; nr < ncoords; nr++) if (coords [nr] != D_MISSING)
{
        nv++;
        mean += coords [nr];
        }
    if (nv) {
        mean /= (double) nv;
        for (nr = 0 ; nr < ncoords; nr++) if (coords [nr] != D_MISSING)
{
            sq = coords [nr] - mean;
            sq *= sq;
            ssq += sq;
```

```
            if (coords [nr] > hicl || coords [nr] < locl) cssq += sq;
        }
        sprintf (msg,
"Values within contours represent %5.2f%% of total %s variance",
            100.0 * cssq / ssq, ftn [ftype - 1]);
        dab$dut_shomsg (msg);
        }
    UTL$VMSSTR_DISPOSE (vmsname);
done:
    return;
err: dab$dut_sho_err ("Writing Contour data file");
    fclose (fp);
    goto done;
} static int q3$map_wriflo (fp, val)
/* SUBROUTINE ================================================== */
/* writes double, as float, to fp; signals a write error */
FILE *fp;
double val;
{
    float ans;

ans = (float) (val == D_MISSING) ? MISSING : val;
    return (fwrite (&ans, sizeof (float), 1, fp));
} double *q3$map_receptor(ndim, vtype)
/* SUBROUTINE ================================================== */
/* builds and returns the data to be plotted against 3D
coords, as weighted scalar product over the cpds, of the
energies and the PLS coefficients, weighted as input by user
*/
int *ndim, *vtype;
{
    double *coeff, dab$arr_gdbl(), q3$map_ptvolume (), ptvol = 1.0,
sqrt(),
        *coords, dab$dut_g2df(), term, *q3$cmpr_read(), sum, sumsq, val;
    struct ana_header *a;
    struct tbl_header *tptr;
    int nys, ny = 0, nterms, bootstrap, ib = 0, nx, ie, i, j, nxs,
        c17 = 17, c1 = 1, nm, all, c16 = 16, c23 = 23, results;
    struct col_header *cptr;

if (dab$dut_not_tbl (0)) return (FALSE);

/* get type of data weighting from user */
        if (!dab$usr_getcase ("all_cpds", &all)) return (FALSE);

/* 1 means average over all cpds, 2 contribution of only 1, 3
= only coefficients, 4 means standard deviation of input
columns (mean of electrostatic and static), 5 means external
file, 6 means field of only one cpd */

*vtype = all;
```

```
tptr = dab[0];
if (all == 5) return (q3$cmpr_read (ndim));
    else {
      if (all == 2 || all == 6)
         if (!dab$usr_getbint ("Plan ID# of compound",
            1, Q3D -> nmols, &nm)) return (FALSE);
         nm--;
         }
      a = tptr -> anahead;
      if (!(results = a -> results)) {
         if (all != 6) {
           dab$dut_sho_err("No results present");
           return (FALSE);
           }
            nys = 0;
            }
         else {
            dab$pls4_getint (&results, &nys, &c17);
            dab$pls4_getint (&results, &coeff, &c1);
            dab$pls4_getint (&results, &nterms, &c16);
            dab$pls4_getint (&results, &bootstrap, &c23);
            if (bootstrap && all <= 3) {
                ib = bootstrap;
                dab$dut_sho_err (
"This operation invalid for cross-validated or bootstrapped equation ");
                dab$dut_shomsg (
"You should Rederive the equation, stating number of components to be
used");
                return (FALSE);
                }
            if (nys > 1 && all < 4) {
                if (!dab$usr_getbint ("For which bio variable", 1, nys,
&ny)) return (FALSE);
                 ny--;
                 }
                if (all == 1) ptvol = q3$map_ptvolume() / (double) a ->
nrows;
                } nx = tptr -> ncols - nys;
        if (!dab$mat_spdbl (&coords, nx, "")) return (FALSE);
        for (i = 0, ie = 0; i < nx; i++) {
            if (all == 4) {
            cptr = tptr -> colhead + i + nys;
            coords [ie] = cptr -> std_dev;
            }
            else if (all == 6) {
            coords [ie] += dab$dut_g2df (tptr -> data,
                tptr -> coldim,   nm, ie + nys);
            }
            else if (!dab$bit_isiton (a -> cols_in, nys + i))
                coords [ie] = D_MISSING;
            else {
            coords [ie] = 0.0;
                term = dab$arr_gdbl (coeff, ib, ie, nterms, ny, nys);
            switch (all) {
       case 1:      for (j = 0, nxs = 0, sum = 0.0, sumsq = 0.0;
                        j < tptr -> nrows; j++)
```

```
                    if (dab$bit_isiton (a -> rows_in, j)) {
                        val = dab$dut_g2df (tptr -> data,
                            tptr -> coldim,   j, ie + nys);
                        sum += val; sumsq += val * val;
                        nxs++;
                        }
                val = (double) nxs;
                coords [ie] = nxs > 1 ?
                    term * sqrt((sumsq - ((sum * sum)/val))/(val - 1.0)) :
                    D_MISSING;
                break;
        case 2:         coords [ie] += dab$dut_g2df (tptr -> data,
                    tptr -> coldim,   nm, ie + nys) * term;
                break;
        case 3:     coords [ie] = term;
                break;
                }
            }
          ie++;
          }
      *ndim = nx;
      return (coords);
      } int q3$map_display (source, maptype, workarea)
/* MAIN SUBROUTINE =================================================== */
/* displays, as scatter plot, any of several different CoMFA
displays of field data as a function of spatial coordinates,
especially (by default) the QSAR coefficient times the
standard devn of the column values. */ short *workarea,        /* where should display go */
    *source,            /* 1 = individual molecule, 2 = overall
QSAR */
    *maptype            /* 1 = steric 2 = electrostatic, 3 = both
(in separate backgrounds) */
    ;
{
   struct q3mol *m, *q3$mol_select();
   struct q3conf *cf, *q3$cnf_select();
   int nr, ie, i, c17 = 17, c1 = 1, ny = 0, nx, results, c23 = 23, c16 =
16,
        ib = 0, nys, j, vtype;
   double *coords, *q3$map_receptor();

/* color bounds */
    static double histeric[] = {-10.0, -1.0, -0.1, 0.1, 1.0, 10.0};
    static double hielec[] = {-10.0, -1.0, -0.1, 0.1, 1.0, 10.0};

coords = 0;
   if (!Q3D) {dab$dut_sho_err ("No plan"); return;}
   switch (*source) {
case 1:     if (!(m = q3$mol_select (&nr))) return;
        if (!(cf = q3$cnf_select (m, &nr))) return;
        if (!(ie = cf -> encoords / 2)) {
          dab$dut_sho_err ("No energy map for the conformer");
          return;
```

```
            .}
        coords = cf -> emap;
        break;
case 2: if (!(coords = q3$map_receptor (&nx, &vtype))) return;
        ie = nx / 2;
        break;
        }
/* build maps */
    switch (*maptype) {
case 1: if (!q3$map_make (coords, *workarea, cf, ie, histeric, 1,
*source))
            return (FALSE);
        break;
case 2: if (!q3$map_make (&(coords [ie]), *workarea, cf, ie,
            hielec, 2, *source)) return (FALSE);
        break;
case 3: if (!q3$map_make (coords, *workarea, cf, ie, histeric, 1,
*source))
            return (FALSE);
        if (!dab$usr_getcase ("work_area", &workarea))
            return (FALSE);
        if (!q3$map_make (&(coords [ie]), workarea, cf, ie,
            hielec, 2, *source)) return (FALSE);
        break;
        } if (coords) UTL_MEM_FREE (coords);
    return (TRUE);
} static int q3$map_make (edata, workarea, cf, npts, eranges, eidx,
source)
/* SUBROUTINE =================================================== */
/* makes and displays data vs 3D coords as scatter plot,
rather than contour map */
double *edata, *eranges;
int workarea, source;
struct q3conf *cf;
int npts, eidx;
{
    char *bfname, *dab$dsp_opfname(), *UTL$STR_SAVE();
    int npoints, zero = 0, i, idx, colidx, one = 1, two = 2, regstep,
        npt, fd, wa, *color, tblid, *pidx;
    static double *dcoords;
    double *q3$map_nxc(), *q3$map_initc(), *x, *y, *z,
        dab$dut_dbl_maxmin(), max, min, range;
    float coords [3], save;
    short nc = 4, nr, no = 0, tsh, negl = -1;
    static char *colabs[] = {"x","y","z","St.En","El.En."};
    static int colids[] = {0, 1, 2, 3};
    struct tbl_header *tptr;
    struct col_header *cptr;

wa = workarea - 1;
    x = y = z = 0; pidx = color = 0;
    if (!dab$mat_spdbl (&x, npts, "")) goto done;
    if (!dab$mat_spdbl (&y, npts, "")) goto done;
```

```
        if (!dab$mat_spdbl (&z, npts, "")) goto done;
        if (!dab$mat_spint (&color, npts, "")) goto done;
        if (!dab$mat_spint (&pidx, npts, "")) goto done;

/* create table for response to point selection from scatter
graph */
        if (!(tblid = dab$ini_tblid () ) < 0) {
            dab$dut_shomsg ("Deleting oldest display table");
            dab$ini_free_all (3);
            dab [3] = 0;
            tblid = 3;
            }
        sprintf (msg, "Associated data stored in DABYL table # %d",
tblid+1);
        dab$dut_shomsg (msg);
        tsh = (short) tblid;  nr = (short) npts;
        if (!dab$ini_table (&tsh, &nr, &nc, &no, &no, &tsh)) return (FALSE);
        tptr = dab [tblid];
/* column names */
        tptr -> cols_named = TRUE;
        for (i = 0; i < 4; i++) {
            cptr = tptr -> colhead + i;
            if (!(cptr -> name_ptr =
                UTL$STR_SAVE (colabs [i < 3 ? i : i+eidx-1]) )) {
                    dab$dut_mem_err ("Label"); goto done;}
            if (i == 3 && source == 3) cptr -> frc_width = 4;
            }

/* data */
        if (source == 3) range = dab$dut_dbl_maxmin (edata, npts, &max,
&min);

dcoords = q3$map_initc (&regstep, &neg1, 0, 0, 0);
        for (npt = idx = 0; dcoords; idx++, dcoords = q3$map_nxc
            (&regstep, &neg1, 0, 0, 0)) {
         for (i = 0; i < 3; i++) dab$dut_p2df (tptr -> data, tptr -> coldim,
            idx, i, dcoords [i]);
         dab$dut_p2df (tptr -> data, tptr -> coldim, idx, 3,
            edata [idx] == fabs(Q3D -> too_big) ? D_MISSING : edata [idx]);
         x [npt] = dcoords [0];
         y [npt] = dcoords [1];
         z [npt] = dcoords [2];
         pidx [npt] = idx;

/* compute color for each displayed point */
         if (source == 3) {
            colidx = (int) (7.0 * (edata [idx] - min) / range) + 1;
            if (colidx > 7) colidx = 7;
            }
         else {
            for (colidx = 0, fd = FALSE; (colidx < 6) && !fd; colidx++)
                fd = edata [idx] < eranges [colidx];
            if (!fd) colidx = 6;
            }
         color [npt] = colidx;
         if (edata [idx] != D_MISSING) npt++;
         }
/* post graph */
```

```
    dab$sca_show (wa, tblid, -1, -1, -1, -1,
        npts, 1, pidx, 0, 0, 0, 3, 2, colids,
        2, 0, TRUE, x, y, z, TRUE, color, colabs [eidx + 2], 0, 0, 0,
0);

/* visible title */
    if (!(bfname = dab$dsp_opfname (wa, TRUE, 0))) goto done;
    sprintf (msg, "%s for %s", colabs [eidx + 2], source == 1 ? cf ->
m_name : "Receptor");
    dab$bkg_label (msg, -7.0, 7.0, 0.0);
    SBL$WDSP_CLOSE();
    dab$dsp_post(wa, bfname, "Region Map");

done:
    if (x) UTL_MEM_FREE (x);
    if (y) UTL_MEM_FREE (y);
    if (z) UTL_MEM_FREE (z);
    if (color) UTL_MEM_FREE (color);
    return (TRUE);
}

/* the following variable values controlled by following two
routines */
    static int xstep, ystep, zstep;
    static double coords[3];
    static struct q3region *regn;

double *q3$map_nxc (regstep, molarea, vdwB, vdwA, chg)
/* ============================================================ */
/* Used throughout CoMFA to sequentially process a set of
lattices (AKA regions). On each call, returns pointer to next
set of coordinates defined by the Plan description of region;
returns 0 (FALSE) when no more. If molecule present (molarea
> 0) and probe atom is associated with region, and region
changes, recomputes all values of vdw and charges, based on
interaction between molecule in molarea & the probe.

x varies > y varies > z varies > region.

Precede its use by call to q3$map_initcoords(), which
initiates counters and returns first set of coords. */ int *regstep;      /* This is OUTPUT - tells caller if region
changed */
short *molarea;
double *vdwA, *vdwB, chg;
{
    int i;

if (!Q3D -> reg_ptr) return (FALSE);

xstep++;
    if (xstep < regn -> nsteps [0]) {
        coords [0] += regn -> step_size [0];
        return (coords);
        }
    coords [0] = regn -> lo_coords [0];
```

```
    xstep = 0; ystep++;
    if (ystep < regn -> nsteps [1]) {
        coords [1] += regn -> step_size [1];
        return (coords);
        }
    coords [1] = regn -> lo_coords [1];
    ystep = 0; zstep++;
    if (zstep < regn -> nsteps [2]) {
        coords [2] += regn -> step_size [2];
        return (coords);
        }

/* traversed all coordinates for this region if got here */
    zstep = 0; *regstep = *regstep + 1;
    if (*regstep < Q3D -> nregions) {
        regn = Q3D -> reg_ptr + *regstep;
        for (i = 0; i < 3; i++) coords [i] = regn -> lo_coords [i];
        if (*molarea >= 0) q3$map_nuparams (molarea, regn, vdwA, vdwB,
chg);
        return (coords);
        }

/* finished processing all regions defined if got here */
    return (FALSE);
} double *q3$map_initc (regstep, molarea, vdwA, vdwB, chg)
/* SUBROUTINE ============================================ */
/* initializes scan of regions described by the user. Returns
coords of 1st lattice point (if present). See preceding
routine. */
int *regstep;
short *molarea;
double *vdwA, *vdwB, chg;
{
    int i;

if (!Q3D -> reg_ptr) return (FALSE);

xstep = ystep = zstep = 0;
    *regstep = 0;
    regn = Q3D -> reg_ptr;
    for (i = 0; i < 3; i++) coords [i] = regn -> lo_coords [i];
    if (*molarea >= 0) q3$map_nuparams (molarea, regn, vdwA, vdwB, chg);
    return (coords);
} static int q3$map_nuparams (molarea, r, vdwA, vdwB, chg)
/* SUBROUTINE ============================================ */
/* called when next region is being processed. Checks to see
if each region has its own probe atom; if so, recomputes all
charge and vdw interaction parameters between the region
probe atom and the molecule in molarea */
short *molarea;
double *vdwA, *vdwB, *chg;
struct q3region *r;
```

```
{
   int natm, anow, i, j;
   short a1, a2, a0, isht;

if (r -> nsteps [0] != 1 || r -> nsteps [1] != 1
         || r -> nsteps [2] != 1 || r -> step_size [0]) return
(TRUE);
   q3f$syb_gnatoms (molarea, &natm);
   fndchg (&a0, &a1, &a2, molarea);
   for (i = 0, isht = 1; i < natm; i++, isht++) {
       q3f$echarge (&a0, &isht, molarea, &(r -> step_size [2]),
            &(chg [i]));
       j = i+1;
       q3f$syb_atype (&j, molarea, &anow);
       q3$eva_VDW_tab (anow, (int) (r -> step_size [1]), &(vdwA [i]),
            &(vdwB [i]), Q3D -> ffield);
       }
   return (TRUE);
} int q3$map_list (maptype, unit)
/* MAIN SUBROUTINE ===================================== */
/* lists, to logical unit specified, the numerical values
produced by CoMFA */ short *unit,
      *maptype /* 2 = electrostatic, 1 = steric, 3 = both   */
      ;
{
  struct q3mol *m, *q3$mol_select();
  struct q3conf *cf, *q3$cnf_select();
  int nr;

if (!Q3D) {dab$dut_sho_err ("No plan"); return;} if (!(m = q3$mol_select (&nr))) return;
       if (!(cf = q3$cnf_select (m, &nr))) return;
       if (!cf -> encoords) {
          dab$dut_sho_err ("No energy map for the conformer");
          return;
          }
   if (!dab$lis_openwf (unit)) return (FALSE);

if (*maptype == 2 || *maptype == 3)
       q3$map_write (cf -> emap, "ELECTROSTATIC", cf);

if (*maptype == 1 || *maptype == 3)
       q3$map_write (&(cf -> emap [(cf -> encoords)/2]), "STERIC", cf);

return (TRUE);
} define EWIDTH 7 static void q3$map_write (edata, ename, cf)
```

```c
/* SUBROUTINE ============================================== */
/* actually writes the numerical values */
double *edata;
char *ename;
struct q3conf *cf;
{
    double *coords, zcoord, ycoord, *q3$map_initc(), *q3$map_nxc();
    int regstep, lastreg, np;
    short neg1 = -1;

coords = q3$map_initc (&regstep, &neg1, 0, 0, 0);
    q3$map_regheader (ename, regstep, cf);
    for (np = 0; coords; np++, coords = q3$map_nxc (&regstep, &neg1,
0,0,0)) {
        if (regstep != lastreg)
          q3$map_regheader (ename, regstep, cf);
        if (coords [2] != zcoord || regstep != lastreg)
            q3$map_blkheader (regstep, coords[2]);
        if (coords [1] != ycoord || coords [2] || zcoord ||
            regstep != lastreg) {
            fprintf (fp, "%*.1f", EWIDTH, coords [1]);
            if (!dab$lis_line()) return;
            }
        if (edata [np] >= fabs(Q3D -> too_big) )
            fprintf (fp, "%*s", EWIDTH, "     -    ");
          else fprintf (fp, "%*.3f", EWIDTH, edata[np]);
        lastreg = regstep; ycoord = coords [1]; zcoord = coords [2];
        }
    if (!dab$lis_nline(2)) return;
} static void q3$map_regheader (ename, regstep, cf)
/* SUBROUTINE ============================================== */
/* writes header for new region, including conformer
identification */
char *ename;
int regstep;
struct q3conf *cf;
{
    struct q3region *r;

if (unit != 1) fprintf (fp, " \f");
    fprintf (fp,
"%s Field Values for Conformer #%d", ename, cf -> m_name);
    if (!dab$lis_nline(2)) return;
    fprintf (fp, "Region # %d", regstep + 1);
    r = Q3D -> reg_ptr + regstep;
    q3$lis_region (r);
    return;
} static void q3$map_blkheader (rstep, zcoord)
/* SUBROUTINE ============================================== */
/* at top of new z block, writes x coord values as column
headers */
int rstep;
```

```
double zcoord;
{
    int i;
    double xcoord;
    struct q3region *r;

fprintf (fp, "%*s", EWIDTH, "   y \\ x");
    r = Q3D -> reg_ptr + rstep;
    for (i = 0, xcoord = r -> lo_coords [0]; i < r -> nsteps [0];
            i++) {
        fprintf (fp, "%*.1f", EWIDTH, xcoord);
        xcoord += r -> step_size [0];
        }
    return (dab$lis_line());
} double q3$map_ptvolume ()
/* SUBROUTINE ================================================== */
/* returns magnitude of the volume represented by a lattice
point, as total of all region volumes divided by total number
of lattice points */
{
    double vol = 1.0;
    struct q3region *r;
    int i, nr, npts = 0;

for (nr = 0; nr < Q3D -> nregions; nr++) {
    r = Q3D -> reg_ptr + nr;
    for (i = 0; i < 3; i++) vol *= (r -> step_size [i])
        * (double) (r -> nsteps [i] - 1);
    npts += q3$eva_npts (r);
    }
    if (Q3D->nregions > 1) dab$dut_shomsg ("Average Region size used");
    return (vol ./ (double) npts);
}
```

Functional Description of All Subroutines called by the Four Core Program Segments The purpose of this listing is to facilitate the implementation of the CoMFA technique, by describing the purpose of all subroutines whose source code is not actually provided. Either functionally equivalent routines will have to be written or otherwise acquired, or in some instances it may be preferable to modify the provided code so that a subroutine is not actually needed. Routines whose names begin with q3$eva_, q3$ff_, or q3$map_ are excluded, since complete source code is provided for these. Also excluded are subroutines such as "fprintf" which are part of any C language implementation.

When in the description of a subroutine's purpose it is necessary to distinguish its arguments, the arguments are labelled (A1),(A2)...(An).

The routines are divided into four groups, as follows:
1) General input/output and memory management routines
2) Input/output utilities associated directly with CoMFA.
3) Routines which access molecular data or display facilities provided by the molecular modeling software support system, in this case SYBYL.
4) Routines which manipulate tables of numbers or bitsets, which for simplicity in some other implementation might instead be conventional arrays.

Within each group the listing is alphabetical.

1) General input/output and memory management routines dab$dut_sho_err - prints error message to console dab$dut_shomsg - writes any message to console dab$lis_line - moves the writing position to the next line, and takes any appropriate action if that movement fills a page. Returns false if user aborts listing.

dab$lis_nline - moves the writing position to the current line plus (A1), and takes any appropriate action if that movement fills a page Returns false if the user aborts the listing.

dab$lis_openwf - requires the user to designate where (screen, printer, disk file) a listing is to go (A1). Returns false if user aborts.

dab$mat_spdbl - puts storage for requested number of "double"s (A2) at (A1). Prints (A3) and returns fail if request fails.

dab$mat_spint - puts storage for requested number of integers (A2) at (A1). Prints (A3) and returns fail if request fails.

dab$dut_mem_err - prints "out of memory" error to console.

dab$stmp_list - writes to (A1) the time-date stamp info referenced by (A2).

dab$usr_cmgetbint - Requests user to enter an integer (A4) whose value is between (A2) and (a3) in response to a question (A1 is its label). Returns false if user interrupts action.

dab$usr_cmgetreal - Requests user to enter a floating point number (A2) in response to a question (A1 is its label). Returns false if user interrupts action.

dab$usr_cmtext - Requests user to enter some text (A2) in response to a question (A1 is its label). Returns false if user interrupts action.

dab$usr_getcase - Requests user to select one item (A2) from a list of items (A1 is label for list). Returns false if user interrupts action.

dab$usr_getstring - Requests user to enter some text (A2) in response to a question (A1). Returns false if user interrupts action.

dab$usr_ynans - Requests user to answer (A4) yes or no to a question (A1). Returns false if user interrupts action.

dab$wri4_int - write a message containing an integer to the console

UTL$STR_SAVE - returns a C copy of a C string

UTL$VMSSTR_CARVE - returns a VMS string copy of a C string.

UTL$VMSSTR_DISPOSE - releases storage used by a VMS string copy to the operating system.

UTL_MEM_CALLOC - requests storage for (A1) items each (A2) bytes long.

UTL_MEM_FREE - releases storage to the operating system for an item no longer needed by the program.

2) Input/output routines associated directly with CoMFA.

q3$add_ok - checks for presence of a Plan q3$cmpr_read - attempts to read a field from a separate file, whose name the user will supply.

q3$cnf_select - requires user to select a conformer (A2) from among those referenced by Plan, from molecule (A1). Returns false if he aborts.

q3$ff_getors - requires user to specify a torsional angle (to be varied as part of a Field Fit operation.)

q3$lis_aname - writes a text description corresponding to the numerical atom type.

q3$lis_region - writes a text description of a region or lattice (A1).

q3$mol_select - requires user to select a molecule (A1) from among those referenced by Plan. Returns false if he aborts.

q3$reg_select - requires user to select a region or lattice (A1) from among those referenced by Plan. Returns false if he aborts.

3) Routines which access the molecular modeling support software.

aatom - adds an atom of name (A1) and type name (A2) and coordinates (A3,A4,A5) to the currently designated molecule.

bestfit - rotate and translate molecule (A1) so that the coordinates of the (A2) atoms whose identifiers are in (A3) will have the smallest possible least squares distances from the corresponding atoms (also in A3) in the molecule in location 2.

change - apply an incremental torsional rotation (A2) about bond (A3,A4,A5,A6) in molecule (A7).

dbget0 - retrieves molecule (A2) from a data abse into an area (A1), setting (A3) to not-zero if an error.

dab$bkg_label - add to the current "background" display a text string (A1) at the location whose coordinates are (A2,A3,A4).

dab$dsp_ofname - returns the name of a new "background" file, for accumulating text, lines, and points, to be displayed on the screen.

dab$dsp_post - display the named (A2) background in the (A1) display area.

dbmol - writes a description of the molecule (A1) to a disk file (name = A3).

dbput - adds the molecule (A1) to a data base as item (A2).

display - display the designated molecule on the screen edit - make the designated molecule the default molecule (the one operated on by commands which do not ask the user for a designated molecule).

fdab$anginit - opens an "angle" file (A1), containing results from a search of torsional space, and obtain various descriptions of its contents.

fndchg - initializes access to atomic charges.

getconf - retrieve the next sequential torsional angle settings (A1) from an "angle" file.

gtconeng - retrieve the energy content of the most recently retrieved torsional angle setting from an "angle" file.

orient - rotate/translate molecule (A1) so that atom (A2) is at the origin, atom (A2) on the X-axis, and atom (A3) is in the XZ plane.

par$close_minvdw - close a data base of vdw (steric size) parameters whose entries are keyed by atom type par$minvdw - obtains vdw epsilon corresponding to an atom type par$open_minvdw - open a data base of vdw (steric size) parameters whose entries are keyed by atom type q3f$echarge - places product of (A4) and charge on atom (A2) of molecule (A3) in element (A5) of array.

q3f$syb_aprop_dbl - obtains (A3) the "double" property of type (A2) for atom of type (A1).

q3f$syb_aprop_int - obtains (A3) the integer property of type (A2) for atom of type (A1).

q3f$syb_atype - obtains (A3) the atom type of atom (A1) of molecule (A2).

q3f$syb_getcoords - obtains atomic coordinates (A1) to a designated molecule (A2) having (A3) atoms.

q3f$syb_gnatoms - gets # of atoms (A2) in designated molecule (A1)

q3f$syb_putcoords - supplies atomic coordinates (A1) to a designated molecule (A2) having (A3) atoms.

q3f$tau - obtain the absolute torsional angle (A6) current for bond (A1,A2,A3,A4) in molecule (A5).

q3$mol_dbaseopen - opens a molecule data base whose description is referenced by (A1).

q3user_contour - begins interactive contouring of data in a file (A1), returning the highest low and lowest high contour levels chosen by the user.

SBL$WDSP_CLOSE - close a display "background" file.

SYB_MATH_SIMPLEX - performs a Simplex minimization. The code Tripos used is taken from a standard book "Numerical Recipes".

UTL_GEOM_IDENTITY - loads the identity (null operation) matrix.

UTL_GEOM_MAKE_ROT-(X,Y,Z) - calculates matrix (A2) for rotation by (A1) about named axis.

UTL_GEOM_MFORM - calculates matrix operation (A4) equivalent to rotating an object by (A3) around a line connecting (A1) and (A2)
(bond rotation).

UTL_GEOM_MMULT - calculates matrix (A1) of multiplying (A2) by (A3).

UTL_GEOM_MROTATE - performs a matrix rotation (A2) about (A1) on (A3).

UTL_GEOM_ROTATE - performs an angle rotation (A2) about (A1) on (A3).

UTL_GEOM_VDIST(_SQ) - returns distance (square of distance) between two coordinates.

zap - deletes the designated molecule

4) Routines which manipulate tables of numerical data or bitests.

dab$arr_gdbl - returns a value from the (A4,A5,A6) location of a three-dimensional array (A1) with (A2) columns and (A3) rows.

dab$bigger - expand a table of data (A1) by inserting (A3) rows or columns (depends on A2) after row or column (A4).

dab$bit_init - set all members of set (A1) to false.

dab$bit_isiton - true if item (A2) is a member of a set (A1)

dab$bit_on - make item (A2) a member of (A1).

dab$dut_colid_ok - checks that column (A2) is a legal entity of table (A1).

dab$dut_g2df - returns a value from the (A3,A4) location of a two-dimensional array (A1) with (A2) columns.

dab$dut_dbl_maxmin - obtains the maximum (A3) and minimum (A4) of (A2) "double"s at location (A1).

dab$dut_not_tbl - returns true if (A1) is not currently a valid table reference.

dab$dut_p2df - adds a value (A5) to a two-dimensional array (A1) with (A2) columns at the (A3,A4) location.

dab$dut_rowid_ok - checks that row (A2) is a legal entity of table (A1).

dab$fil_setrange - calculates univariate statistics (mean, st.devn) of column (A2) in table (A1).

dab$ini_free_all - releases storage used by a table, no longer needed, to the operating system.

dab$ini_tblid - provides a reference for a new empty table dab$ini_table - obtains storage for a new empty table (A1) with (A2) rows and (A3) columns.

dab$mat_spbit - puts storage for a bitset of requested size (A2) at (A1). Prints (A3) and returns fail if request fails.

dab$pls4_getint - retrieves a pointer (A1) to a particular type (A3) of results from PLS analysis (A2).

dab$sca_show - constructs and displays a scatter plot from designated columns of data in a designated table. Text and axes are displayed in separate operations.

MATRIX - save regression coefficients from PLS

QQ - calculates quantiles for a set of numbers (values that would be found if the set of numbers had some prescribed distribution, such as "normal").

RANUMS - put (A1) random numbers in (A2).

RESID - save residuals (differences between actual and predicted values, obtained by cross-validation).

SORT - put the sorted order of (A3) numbers in (A1) into (A2).

We claim:

1. A molecule having an overall structure substantially similar to those of other molecules in a series of molecules known to interact with a common molecule, and having shape determinants which are designed to increase or decrease said molecule's reactivity with said common molecule where a 3-D QSAR indicates that changes in shape determinants are strongly correlated with an increase or decrease in reactivity of the molecules of said series of molecules with said common molecule, said 3-D QSAR being derived by a computer-based method comprising the steps of:
   a. aligning each molecule in said series with the common shape elements of all the molecules in said series;
   b. defining molecular shape discriptors for each molecule in said series of molecules wherein each molecule is associated with a unique parameter value;
   c. correlating the molecular shape descriptors and unique parameter value of each molecule with all the other molecules in said series;
   d. visually displaying using computer graphics the correlation among the molecules in said series.

2. The molecule of claim 1 wherein in the 3-D QSAR derivation in Step (a) each molecule is aligned by minimizing the root mean squared difference in the sum of steric and electrostatic interaction energies (calculated between a mathematical representation of a probe and the molecule at every intersection point of a lattice surrounding the molecule) averaged across all lattice points between the molecule and another molecule in the series.

3. The molecule of claim 1 wherein in the 3-D QSAR derivation the shape of each molecule in Step (b) is defined by the steric and electrostatic interaction energies calculated between a mathematical representation of a probe and the molecule at every intersection point of a lattice surrounding the molecule.

4. The molecule of claim 1 wherein in the 3-D QSAR derivation the correlation in Step (c) is performed by partial least squares analysis using cross-validation after each component extraction.

5. The molecule of claim 1 wherein in the 3-D QSAR derivation the correlation among the molecules is visualized in Step (d) by displaying in three dimensions the correlation solution values corresponding to each point in lattice space.

6. A molecule having an overall structure substantially similar to those of other molecules in a series of molecules known to interact with a common molecule, and having shape determinants which are designed to increase or decrease said molecule's reactivity with said common molecule where a 3-D QSAR indicates that changes in shape determinants are strongly correlated with an increase or decrease in reactivity of the molecules of said series of molecules with said common molecule, said 3-D QSAR being derived among said series of molecules, each of which is associated with a particular property and whose basic structure, including conformers, have been modeled in a three dimensional lattice, by a computer-based method comprising the steps of:
   a. aligning all conformers of all molecules in said series of molecules;

b. selecting a conformer of a molecule;

c. successively placing a mathematical representation of a probe of user specified size and charge at each lattice intersection;

d. calculating the steric and electrostatic energies of interaction between the probe and the conformer at each lattice intersection;

e. entering the steric and electrostatic interaction energies calculated in step (d) in a row of a data table identified with the conformer;

f. selecting a next conformer of the molecule and repeating steps (c) through (e);

g. repeating step (f) for all conformers of the molecule to be considered;

h. weighting and then averaging the interaction energies across all conformers of the molecule and placing the averaged interaction energies in a row of a 3-D QSAR data table along with the value of the particular property associated with the molecule;

i. repeating steps (b) through (h) for all molecules to be considered;

j. extracting a component by applying the partial least squares statistical methodology to said 3-D QSAR data table;

k. performing a cross validation cycle on said 3-D QSAR data table using solution coefficients resulting from the component extraction;

l. adding the extracted components;

m. repeating steps (j) through (l) until all desired components have been extracted;

n. rotating the partial least squares solution consisting of the sum of the extracted components back into the original metric space deriving the solution coefficients; and o. displaying the solution.

7. The molecule of claim 6 further comprising in the 3-D QSAR derivation the additional step of varying the size and charge of the probe by varying its mathematical representation in accordance with user specified criteria as it is placed successively at each lattice intersection.

8. The molecule of claim 6 further comprising in the 3-D QSAR derivation the additional step of varying the spacing of the lattice intersections in accordance with user specified criteria as the mathematical representation of the probe is placed successively at each lattice intersection.

9. The molecule of claim 6 in which in the 3-D QSAR derivation the alignment of the conformers is performed by the FIT method.

10. The molecule of claim 6 in which in the 3-D QSAR derivation the alignment of the conformers is performed by the ORIENT method.

11. The molecule of claim 6 in which in the 3-D QSAR derivation the alignment of the conformers is performed by the FIELD FIT method.

12. The molecule of claim 6 in which in the 3-D QSAR derivation the interaction energies of the conformers are weighted before averaging in accordance with a Boltzman distribution over the energies of the conformers.

13. The molecule of claim 6 further comprising in the 3-D QSAR derivation the additional step, before performing the partial least squares analysis, of placing in the columns of each row a 3-D QSAR data table in addition to the interaction energies additional molecular parameters associated with the molecule represented by the row.

14. The molecule of claim 6 in which in the 3-D QSAR derivation the solution terms are displayed in three dimensional scatter plots corresponding to points in lattice space.

15. The molecule of claim 14 further comprising in the 3-D QSAR derivation the additional step of displaying a molecular model superimposed on the scatter plots.

16. The molecule of claim 6 in which in the 3-D QSAR derivation the solution terms are displayed in three dimensional contour plots defining volumes in lattice space.

17. The molecule of claim 16 further comprising in the 3-D QSAR derivation the additional step of displaying a molecular model superimposed on the contour plots.

18. A molecule synthesized after determining its likely biological or chemical activity by a computer implemented method of determining the likely biological or chemical activity of a test molecule whose basic structure has been modeled in a three dimensional lattice by comparing its three dimensional shape to the shape of other molecules of known biological or chemical reactivity whose 3-D QSAR has previously been determined by the COMFA methodology, comprising the following steps:

a. aligning said molecule to the molecules in the molecular series used to derive the 3-D QSAR solution coefficients;

b. successively placing a mathematical representation of a probe of user specified size and charge at each lattice intersection;

c. calculating the steric and electrostatic energies of interaction between the mathematical representation of the probe and said molecule at each lattice intersection; and d. applying the solution coefficients derived in the 3-D QSAR COMFA analysis of the molecular series to the interaction energies of said molecule to predict the biological or chemical parameter value which said molecule should possess.

19. The molecule of claim 18 further comprising in the computer implemented method the additional step of displaying the calculated interaction energies for the test molecule with the previously derived 3-D QSAR solution coefficient in order to visualize for comparison areas of similarity or difference.

20. The molecule of claim 18 which in the computer implemented method the test molecule has not be synthesized and whose structure and that of its conformers is determined for purposes of placement in the three dimensional lattice from molecular modeling considerations or by molecular modeling techniques.

21. A molecule having an overall structure substantially similar to those of other molecules in a series of molecules known to interact with a common molecule, and having shape determinants which are designed to increase or decrease said molecule's reactivity with said common molecule where a correlation between molecular descriptors and properties of said series of molecules indicates that changes in shape determinants are strongly correlated with an increase or decrease in reactivity of the molecules of said series of molecules with said common molecule, said correlation being derived by a computer implemented method for deriving the correlation between molecular descriptors and properties of a group of molecules where there are many more molecular descriptors for each molecule in the group than there are number of molecules in the group comprising the following steps:

a. generating a data table each row of which contains in its columns the molecular descriptors associated with a single molecule of the group as well as the value of a property in that molecule;

b. extracting a component by applying the partial least squares statistical methodology to the rows of the data table;

c. performing a cross validation cycle on the data table using solution coefficients resulting from the component extraction;

d. adding the extracted components;

e. repeating steps (b) through (d) until all desired components have been extracted;

f. rotating the partial least squares solution consisting of the sum of the exracted components back into the original metric space deriving the solution coefficients; and g. displaying the solution.

22. A molecule having an overall structure substantially similar to those of other molecules in a series of molecules known to interact with a common molecule, and having shape determinants which are designed to increase or decrease said molecule's reactivity with said common molecule where a 3-D QSAR indicates that changes in shape determinants are strongly correlated with an increase or decrease in reactivity of the molecules of said series of molecules with said common molecule, said 3-D QSAR being derived by a system comprising:

a. means for aligning each molecule in said series with the common shape elements of all the molecules in said series;

b. means for defining molecular shape descriptors for each molecule in said series of molecules wherein each molecule is associated with a unique parameter value;

c. means for correlating the molecular shape descriptors and unique parameter value of each molecule with all the other molecules in said series; and d. means for visually displaying using computer graphics the correlation among the molecules in said series.

23. The molecule of claim 22 wherein in the 3-D QSAR derivation the means for aligning each molecule further comprises means for minimizing the root mean squared difference in the sum of steric and electrostatic interaction energies, said energies being calculated between a mathematical representation of a probe and the molecule at every intersection point of a lattice surrounding the molecule, averaged across all lattice points between the molecule and another molecule in the series.

24. The molecule of claim 22 wherein in the 3-D QSAR derivation the means for defining the shapes further comprises means for calculating the steric and electrostatic interaction energies between a mathematical representation of a probe and the molecule at every intersection point of a lattice surrounding the molecule.

25. The molecule of claim 22 wherein in the 3-D QSAR derivation the means for correlating the shape and unique parameter value further comprises means for performing partial least squares analysis using cross validation after each component extraction.

26. The molecule of claim 22 wherein in the 3-D QSAR derivation the means for visually displaying the correlation further comprises means for displaying in three dimensions the correlation solution values corresponding to each point in lattice space.

27. A molecule having an overall structure substantially similar to those of other molecules in a series of molecules known to interact with a common molecule, and having shape determinants which are designed to increase or decrease said molecule's reactivity with said common molecule where a 3-D QSAR indicates that changes in shape determinants are strongly correlated with an increase or decrease in reactivity of the molecules of said series of molecules with said common molecule, said 3-D QSAR being derived among said series of molecules, each of which is associated with a particular property and whose basic structure, including conformers, have been modeled in a three dimensional lattice, by a system comprising:

a. means for aligning all conformers of all molecules;

b. means for selecting a conformer of a molecule;

c. means for successively placing a mathematical representation of a probe of user specified size and charge at each lattice intersection;

d. means for calculating the steric and electrostatic energies of interaction between the probe and the conformer at each lattice intersection;

e. means for entering the steric and electrostatic interaction energies calculated by means (d) in a row of a data table identified with the conformer;

f. means for selecting a next conformer of the molecule and invoking said means (c) through said means (e);

g. means for invoking means (f) for all conformers of the molecule to be considered;

h. means for weighting and then averaging the interaction energies across all conformers of the molecule and placing the averaged interaction energies in a row of a 3-D QSAR data table along with the value of the particular property associated with the molecule;

i. means for invoking means (b) through (h) for all molecules to be considered;

j. means for extracting a component by applying the partial least squares statistical methodology to said 3-D QSAR data table;

h. means for performing a cross validation cycle on said 3-D QSAR data table using solution coefficients resulting from the component extraction;

l. means for adding the extracted components;

m. means for invoking means (j) through (l) until all desired components have been extracted;

n. mean for rotating the partial least squares solution consisting of the sum of the extracted components back into the original metric space deriving the solution coefficients; and o. means for displaying the solution.

28. The method of claim 27 further comprising in the 3-D QSAR derivation additional means for varying the size and charge of the probe by means for varying its mathematical representation in accordance with user specified criteria as it is placed successively at each lattice intersection.

29. The molecule of claim 27 further comprising in the 3-D QSAR derivation additional means for varying the spacing of the lattice intersections in accordance with user specified criteria as the mathematical representation of the probe is placed successively at each lattice intersection.

30. The molecule of claim 27 in which in the 3-D QSAR derivation the means for aligning the conformers utilizes the FIT method.

31. The molecule of claim 27 in which in the 3-D QSAR derivation the means for aligning the conformers utilizes the ORIENT method.

32. The molecule of claim 27 in which in the 3-D QSAR derivation the means for aligning the conformers utilizes the FIELD FIT method.

33. The molecule of claim 27 further comprising in the 3-D QSAR derivation means for weighting the interaction energies of the conformers before averaging in accordance with a Boltzman distribution over the energies of the conformers.

34. The molecule of claim 27 further comprising in the 3-D QSAR derivation, before invoking the means for applying the partial least squares analysis, additional means for placing in the columns of each row of a 3-D QSAR data table, in addition to the interaction energies, additional molecular parameters associated with the molecule represented by the row.

35. The molecule of claim 27 in which in the 3-D QSAR derivation the means for displaying the solution further comprises means for displaying the solution terms in three dimensional scatter plots corresponding to points in lattice space.

36. The means for displaying the solution of claim 35 further comprising additional means for displaying a molecular model superimposed on the scatter plots.

37. The molecule of claim 27 in which in the 3-D QSAR derivation means for displaying the solution further comprises means for displaying the solution terms in three dimensional contour plots defining volumes in lattice space.

38. The means for displaying the solution of claim 37 further comprising additional means for displaying a molecular model superimposed on the contour plots.

39. A molecule synthesized after determining its likely biological or chemical activity by a system of determining the likely biological or chemical activity of a test molecule whose basic structure has been modeled in a three dimensional lattice by comparing its three dimensional shape to the shape of other molecules of known biological or chemical reactivity whose 3-D QSAR has previously been determined by the COMFA methodology, comprising:
  a. means for aligning the test molecule to the molecules in the molecular series used to derive the 3-D QSAR solution coefficients;
  b. means for successively placing a mathematical representation of a probe of user specified size and charge at each lattice intersection;
  c. means for calculating the steric and electrostatic energies of interaction between the mathematical representation of the probe and the test molecule at each lattice intersection; and
  d. means for applying the solution coefficients derived in the 3-D QSAR COMFA analysis of the molecular series to the interaction energies of the test molecule to predict the biological or chemical parameter value which the test molecule should possess.

40. The molecule of claim 39 further comprising in the system additional means for displaying the calculated interaction energies for the test molecule with the previously derived 3-D QSAR solution coefficients in order to visualize for comparison areas of similarity or difference.

41. The molecule of claim 39 in which the test molecule has not been synthesized further comprising in the system additional means for determining the structure of a molecule and of its conformers for purposes of placement in the three dimensional lattice from molecular modeling considerations or by molecular modeling techniques.

42. A molecule having an overall structure substantially similar to those of other molecules in a series of molecules known to interact with a common molecule, and having shape determinants which are designed to increase or decrease said molecule's reactivity with said common molecule where a correlation between molecular descriptors and properties of said series of molecules indicates that changes in shape determinants are strongly correlated with an increase or decrease in reactivity of the molecules of said series of molecules with said common molecule, said correlation being derived by a system for deriving the correlation between molecular descriptors and properties of a group of molecules where there are many more molecular descriptors for each molecule in the group than there are number of molecules in the group comprising:
  a. means for generating a data table, each row of which contains in its columns the molecular descriptors associated with a single molecule of the group as well as the value of a property of the molecule;
  b. means for extracting a component by applying the partial least squares statistical methodology to the rows of the data table;
  c. means for performing a cross validation cycle on the data table using solution coefficients resulting from the component extraction;
  d. means for adding the extracted components;
  e. means for invoking means (b) and (d) until all desired components have been extracted;
  f. means for rotating the partial least squares solution consisting of the sum of the extracted components back into the original metric space deriving the solution coefficients; and
  g. means for displaying the solution.

43. A molecule having an overall structure substantially similar to those of other molecules in a series of molecules known to interact with a common molecule, and having shape determinants which are designed to increase or decrease said molecule's reactivity with said common molecule where a 3-D QSAR indicates that changes in shape determinants are strongly correlated with an increase or decrease in reactivity of the molecules of said series of molecules with said common molecule, said 3-D QSAR being derived by a computer-based method comprising the steps of:
  a. generating for each molecule in the group a row in a data table consisting of molecular parameters uniquely associated with each individual molecule;

b. performing a correlation of all the rows of data in the data table using the partial least squares statistical methodology including cross validation;
c. rotating the solution back into the original metric space; and
d. displaying the correlations among the molecules in the group.

44. A molecule having an overall structure substantially similar to those of other molecules in a series of molecules known to interact with a common molecule, and having shape determinants which are designed to increase or decrease said molecule's reactivity with said common molecule where a 3-D QSAR indicates that changes in shape determinants are strongly correlated with an increase or decrease in reactivity of the molecules of said series of molecules with said common molecule, said 3-D QSAR being derived by a system comprising:
 a. means for generating for each molecule in the group a row in a data table consisting of molecular parameters uniquely associated with each individual molecule;
 b. means for performing a correlation of all the rows of data in the data table using the partial least squares statistical methodology including cross validation;
 c. means for rotating the solution back into the original metric space; and
 d. means for displaying the correlations among the molecules in the group.

45. A computer-based method of generating and visualizing a three-dimensional quantitative structure activity relationship of a series of molecules comprising the steps of:
 a. aligning each molecule in said series with the common shape elements of all the molecules in said series;
 b. defining molecular shape descriptors for each molecule in said series of molecules wherein each molecule is associated with a unique parameter value;
 c. correlating the molecular shape descriptors and unique parameter value of each molecule with all the other molecules in said series;
 d. visually displaying using computer graphics the correlation among the molecules in said series.

46. The computer-based method of claim 45 wherein in Step (a) each molecule is aligned by minimizing the root mean squared difference in the sum of steric and electrostatic interaction energies (calculated between a mathematical representation of a probe and the molecule at every intersection point of a lattice surrounding the molecule) averaged across all lattice points between the molecule and another molecule in the series.

47. The computer-based method of claim 45 wherein the shape of each molecule in Step (b) is defined by the steric and electrostatic interaction energies calculated between a mathematical representation of a probe and the molecule at every intersection point of a lattice surrounding the molecule.

48. The computer-based method of claim 45 wherein the correlation in Step (c) is performed by partial least squares analysis using cross-validation after each component extraction.

49. The computer-based method of claim 45 wherein the correlation among the molecules is visualized in Step (d) by displaying in three dimensions the correlation solution values corresponding to each point in lattice space.

50. A computer implemented methodology for deriving a three dimensional quantitative structure activity relationship (3-D QSAR) among molecules each of which is associated with a particular property and whose basic structures, including conformers, have been modeled in a three dimensional lattice comprising the following steps:
 a. aligning all conformers of all molecules;
 b. selecting a conformer of a molecule;
 c. successively placing a mathematical representation of a probe of user specified size and charge at each lattice intersection;
 d. calculating the steric and electrostatic energies of interaction between the probe and the conformer at each lattice intersection;
 e. entering the steric and electrostatic interaction energies calculated in step (d) in a row of a data table identified with the conformer;
 f. selecting a next conformer of the molecule and repeating steps (c) through (e);
 g. repeating step (f) for all conformers of the molecule to be considered;
 h. weighting and then averaging the interaction energies across all conformers of the molecule and placing the averaged interaction energies in a row of a 3-D QSAR data table along with the value of the particular property associated with the molecule;
 i. repeating steps (b) through (h) for all molecules to be considered;
 j. extracting a component by applying the partial least squares statistical methodology to said 3-D QSAR data table;
 k. performing a cross validation cycle on said 3-D QSAR data table using solution coefficients resulting from the component extraction;
 l. adding the extracted components;
 m. repeating steps (j) through (l) until all desired components have been extracted;
 n. rotating the partial least squares solution consisting of the sum of the extracted components back into the original metric space deriving the solution coefficients; and
 o. displaying the solution.

51. The method of claim 50 further comprising the additional step of varying the size and charge of the probe by varying its mathematical representation in accordance with user specified criteria as it is placed successively at each lattice intersection.

52. The method of claim 50 further comprising the additional step of varying the spacing of the lattice intersections in accordance with user specified criteria as the mathematical representation of the probe is placed successively at each lattice intersection.

53. The method of claim 50 in which the alignment of the conformers is performed by the FIT method.

54. The method of claim 50 in which the alignment of the conformers is performed by the ORIENT method.

55. The method of claim 50 in which the alignment of the conformers is performed by the FIELD FIT method.

56. The method of claim 50 in which the interaction energies of the conformers are weighted before averaging in accordance with a Boltzman distribution over the energies of the conformers.

57. The method of claim 50 further comprising the additional step, before performing the partial least squares analysis, of placing in the columns of each row of a 3-D QSAR data table in addition to the interaction energies additional molecular parameters associated with the molecule represented by the row.

58. The method of claim 50 in which the solution terms are displayed in three dimensional scatter plots corresponding to points in lattice space.

59. The method of claim 58 further comprising the additional step of displaying a molecular model superimposed on the scatter plots.

60. The method of claim 50 in which the solution terms are displayed in three dimensional contour plots defining volumes in lattice space.

61. The method of claim 60 further comprising the additional step of displaying a molecular model superimposed on the contour plots.

62. The computer implemented method of determining the likely biological or chemical activity of a test molecule whose basic structure has been modeled in a three dimensional lattice by comparing its three dimensional shape to the shape of other molecules of known biological or chemical reactivity whose 3-D QSAR has previously been determined by the COMFA methodology, comprising the following steps:
   a. aligning the test molecule to the molecules in the molecular series used to derive the 3-D QSAR solution coefficients;
   b. successively placing a mathematical representation of a probe of user specified size and charge at each lattice intersection;
   c. calculating the steric and electrostatic energies of interaction between the mathematical representation of the probe and the test molecule at each lattice intersection; and
   d. applying the solution coefficients derived in the 3-D QSAR COMFA analysis of the molecular series to the interaction energies of the test molecule to predict the biological or chemical parameter value which the test molecule should possess.

63. The method of claim 62 further comprising the additional step of displaying the calculated interaction energies for the test molecule with the previously derived 3-D QSAR solution coefficients in order to visualize for comparison areas of similarity or difference.

64. The method of claim 62 in which the test molecule has not been synthesized and whose structure and that of its conformers is determined for purposes of placement in the three dimensional lattice from molecular modeling considerations or by molecular modeling techniques.

65. A computer implemented method for deriving the correlation between molecular descriptors and particular values of properties of a group of molecules where there are many more molecular descriptors for each molecule in the group than there are number of molecules in the group comprising the following steps:
   a. generating a data table each row of which contains in its columns the molecular descriptors associated with a single molecule of the group as well as the value of the particular property of that molecule;
   b. extracting a component by applying the partial least squares statistical methodology to the rows of the data table;
   c. performing a cross validation cycle on the data table using solution coefficients resulting from the component extraction;
   d. adding the extracted components;
   e. repeating steps (b) through (d) until all desired components have been extracted;
   f. rotating the partial least squares solution consisting of the sum of the extracted components back into the original metric space deriving the solution coefficients; and
   g. displaying the solution.

66. A system for generating and visualizing a three dimensional quantitative structure activity relationship of a series of molecules comprising:
   a. means for aligning each molecule in said series with the common shape elements of all the molecules in said series;
   b. means for defining molecular shape descriptors for each molecule in said series of molecules wherein each molecule is associated with a unique parameter value;
   c. means for correlating the molecular shape descriptors and unique parameter value of each molecule with all the other molecules in said series; and
   d. means for visually displaying using computer graphics the correlation among the molecules in said series.

67. The system of claim 66 wherein the means for aligning each molecule further comprises means for minimizing the root mean squared difference in the sum of steric and electrostatic interaction energies, said energies being calculated between a mathematical representation of a probe and the molecule at every intersection point of a lattice surrounding the molecule, averaged across all lattice points between the molecule and another molecule in the series.

68. The system of claim 66 wherein the means for defining the shapes further comprises means for calculating the steric and electrostatic interaction energies between a mathematical representation of a probe and the molecule at every intersection point of a lattice surrounding the molecule.

69. The system of claim 66 wherein the means for correlating the shape and unique parameter value further comprises means for performing partial least squares analysis using cross validation after each component extraction.

70. The system of claim 66 wherein the means for visually displaying the correlation further comprises means for displaying in three dimensions the correlation solution values corresponding to each point in lattice space.

71. A system for deriving a three dimensional quantitative structure activity relationship (3-D QSAR) among molecules each of which is associated with a particular property and whose basic structures, including conformers, each have modeled in a three dimensional lattice comprising:
   a. means for aligning all conformers of all molecules;
   b. means for selecting a conformer of a molecule;
   c. means for successively placing a mathematical representation of a probe of user specified size and charge at each lattice intersection;
   d. means for calculating the steric and electrostatic energies of interaction between the probe and the conformer at each lattice intersection;
   e. means for entering the steric and electrostatic interaction energies calculated by means (d) in a row of a data table identified with the conformer;
   f. means for selecting a next conformer of the molecule and invoking said means (c) through said means (e);
   g. means for invoking means (f) for all conformers of the molecule to be considered;

h. means for weighting and then averaging the interaction energies across all conformers of the molecule and placing the averaged interaction energies in a row of a 3-D QSAR data table along with the value of the particular property associated with the molecule;
i. means for invoking means (b) through (h) for all molecules to be considered;
j. means for extracting a component by applying the partial least squares statistical methodology to said 3-D QSAR data table;
k. means for performing a cross validation cycle on said 3-D QSAR data table using solution coefficients resulting from the component extraction;
l. means for adding the extracted components;
m. means for invoking means (j) through (l) until all desired components have been extracted;
n. mean for rotating the partial least squares solution consisting of the sum of the extracted components back into the original metric space deriving the solution coefficients; and
o. means for displaying the solution.

72. The system of claim 71 further comprising additional means for varying the size and charge of the probe by means for varying its mathematical representation in accordance with user specified criteria as it is placed successively at each lattice intersection.

73. The system of claim 71 further comprising additional means for varying the spacing of the lattice intersections in accordance with user specified criteria as the mathematical representation of the probe is placed successively at each lattice intersection.

74. The system of claim 71 in which the means for aligning the conformers utilizes the FIT method.

75. The system of claim 71 in which the means for aligning the conformers utilizes the ORIENT method.

76. The system of claim 71 in which the means for aligning the conformers utilizes the FIELD FIT system.

77. The system of claim 71 further comprising means for weighting the interaction energies of the conformers before averaging in accordance with a Boltzman distribution over the energies of the conformers.

78. The system of claim 71 further comprising, before invoking the means for applying the partial least squares analysis, additional means for placing in the columns of each row of a 3-D QSAR data table, in addition to the interaction energies, additional molecular parameters associated with the molecule represented by the row.

79. The system of claim 71 in which the means for displaying the solution further comprises means for displaying the solution terms in three dimensional scatter plots corresponding to points in lattice space.

80. The means for displaying the solution of claim 79 further comprising additional means for displaying a molecular model superimposed on the scatter plots.

81. The system of claim 71 in which means for displaying the solution further comprises means for displaying the solution terms in three dimensional contour plots defining volumes in lattice space.

82. The means for displaying the solution of claim 81 further comprising additional means for displaying a molecular model superimposed on the contour plots.

83. The system for determining the likely biological or chemical activity of a test molecule whose basic structure has been modeled in a three dimensional lattice by comparing its three dimensional shape to the shape of other molecules of known biological or chemical reactivity whose 3-D QSAR has previously been determined by the COMFA methodology, comprising:
a. means for aligning the test molecule to the molecules in the molecular series used to derive the 3-D QSAR solution coefficients;
b. means for successively placing a mathematical representation of a probe of user specified size and charge at each lattice intersection;
c. means for calculating the steric and electrostatic energies of interaction between the mathematical representation of the probe and the test molecule at each lattice intersection; and
d. means for applying the solution coefficients derived in the 3-D QSAR COMFA analysis of the molecular series to the interaction energies of the test molecule to predict the biological or chemical parameter value which the test molecule should possess.

84. The system of claim 83 further comprising additional means for displaying the calculated interaction energies for the test molecule with the previously derived 3-D QSAR solution coefficients in order to visualize for comparison areas of similarity or difference.

85. The system of claim 83 in which the test molecule has not been synthesized further comprising additional means for determining the structure of a molecule and of its conformers for purposes of placement in the three dimensional lattice from molecular modeling considerations or by molecular modeling techniques.

86. A system for deriving the correlation between molecular descriptors and particular values of properties of a group of molecules where there are many more molecular descriptors for each molecule in the group than there are number of molecules in the group comprising:
a. means for generating a data table, each row of which contains in its columns the molecular descriptors associated with a single molecule of the group as well as the value of the particular property of the molecule;
b. means for extracting a component by applying the partial least squares statistical methodology to the rows of the data table;
c. means for performing a cross validation cycle on the data table using solution coefficients resulting from the component extraction;
d. means for adding the extracted components;
e. means for invoking means (b) and (d) until all desired components have been extracted;
f. means for rotating the partial least squares solution consisting of the sum of the extracted components back into the original metric space deriving the solution coefficients; and
g. means for displaying the solution.

87. A computer based method of designing a molecule which will bind to a larger molecule which is known to bind other molecules with measured affinities comprising the following steps:
a. modeling in a three dimensional lattice the basic structures, including conformers, of molecules known to bind with measured affinities to the larger molecule;
b. aligning all conformers of all molecules;
c. selecting a conformer of a molecule;
d. successively placing a mathematical representation of a probe of user specified size and charge at each lattice intersection;

e. calculating the steric and electrostatic energies of interaction between the probe and the conformer at each lattice intersection;

f. entering the steric and electrostatic interaction energies calculated in step (e) in a row of a data table identified with the conformer;

g. selecting a next conformer of the molecule and repeating steps (d) and (f);

h. repeating step (g) for all conformers of the molecule to be considered;

i. weighting and then averaging the interaction energies across all conformers of the molecule and placing the averaged interaction energies in a row of a 3-D QSAR data table along with a value of a particularly property associated with the molecule;

j. repeating steps (c) through (i) for all molecules to be considered;

k. extracting a component by applying the partial least squares statistical methodology to said 3-D QSAR data table;

l. performing a cross validation cycle on said 3-D QSAR data table using solution coefficients resulting from the component extraction;

m. adding the extracted components;

n. repeating steps (k) through (m) until all desired components have been extracted;

o. rotating the partial least squares solution consisting of the sum of the extracted components back into the original metric space deriving the solution coefficients;

p. displaying the solution; and q. synthesizing a molecule with atoms arranged to occupy or not occupy, as is required, the three dimensional spaces/volumes indicated in the display as being critical to binding of the molecule to the larger molecule.

88. A system for designing a molecule which will bind to a larger molecular which is known to bind other molecules with measured affinities comprising:

a. means for modeling in a three dimensional lattice the basic structures, including conformers, of molecules known to bind with measured affinities to the larger molecule;

b. means for aligning all conformers of all molecules;

c. means for selecting a conformer of a molecule;

d. means for successively placing a mathematical representation of a probe of user specified size and charge at each lattice intersection;

e. means for calculating the steric and electrostatic energies of interaction between the probe and the conformer at each lattice intersection;

f. means for entering the steric and electrostatic interaction energies calculated by means (e) in a row of a data table identified with the conformer;

g. means for selecting a next conformer of the molecule and invoking means (d) through (f);

h. means for invoking means (g) for all conformers of the molecule to be considered;

i. means for weighting and then averaging the interaction energies across all conformers of the molecule and placing the averaged interaction energies in a row of a 3D-QSAR data table along with a value of particular property associated with the molecule;

j. means for invoking means (c) through (i) for all molecules to be considered;

k. means for extracting a component by applying the partial least squares statistical methodology to said 3-D QSAR data table;

l. means for performing a cross validation cycle on said 3-D QSAR data table using solution coefficients resulting from the component extraction;

m. means for adding the extracted components;

n. means for invoking means (k) through (m) until all desired components have been extracted;

o. mean for rotating the partial least squares solution consisting of the sum of the extracted components back into the original metric space deriving the solution coefficients;

p. means for displaying the solution; and q. means for synthesizing a molecule with atoms arranged to occupy or not occupy, as is required, the three dimensional spaces/volumes indicated in the display as being critical to binding of the molecule to the larger molecule.

89. A computer-based method of designing a molecule by generating and visualizing a three-dimensional quantitative structure activity relationship of a series of molecules comprising the steps of:

a. aligning each molecule in said series with the common shape elements of all the molecules in said series;

b. defining molecular shape descriptors for each molecule in said series of molecules wherein each molecule is associated with a unique parameter value;

c. correlating the molecular shape descriptors and unique parameter value of each molecule with all the other molecules in said series;

d. visually displaying using computer graphics the correlation among the molecules in said series;

e. displaying the calculated interaction energies for the test molecule with the previously derived 3-D QSAR solution coefficients in order to visualize for comparison areas of similarity or difference.

90. A system for designing a molecule by generating and visualizing a three-dimensional quantitative structure activity relationship of a series of molecules comprising the steps of:

a. aligning each molecule in said series with the common shape elements of all the molecules in said series;

b. defining molecular shape descriptors for each molecule in said series of molecules wherein each molecule is associated with a unique parameter value;

c. correlating the molecular shape descriptors and unique parameter value of each molecule with all the other molecules in said series;

d. visually displaying using computer graphics the correlation among the molecules in said series;

e. displaying the calculated interaction energies for the test molecule with the previously derived 3-D QSAR solution coefficients in order to visualize for comparison areas of similarity or difference.

* * * * *

UNITED STATES PATENT AND TRADEMARK OFFICE
CERTIFICATE OF CORRECTION

PATENT NO. : 5,307,287
DATED : April 26, 1994
INVENTOR(S) : Ricard D. Cramer, III and Svante B. Wold It is certified that error appears in the above-indentified patent and that said Letters Patent is hereby corrected as shown below:

Column 178, line 4, the phrase "each row a" should be replaced with the phrase --each row of--.

Column 180, line 56, the letter "h." should be replaced with the letter --k.--.

Column 180, line 67, the word "method" should be replaced with the word --molecule--.

Column 186, line 51, the phrase "each have modeled" should be replaced with the phrase ---each have been modeled---.

Column 187, line 38, the word "system" should be replaced with the word ---method---.

Column 189, line 15, the phrase "particularly property" should be replaced with the phrase ---particular property---.

Signed and Sealed this

Twenty-first Day of February, 1995

Attest:

BRUCE LEHMAN

*Attesting Officer*   *Commissioner of Patents and Trademarks*